United States Patent
Buggy et al.

(10) Patent No.: US 9,795,605 B2
(45) Date of Patent: *Oct. 24, 2017

(54) INHIBITORS OF BRUTON'S TYROSINE KINASE FOR THE TREATMENT OF SOLID TUMORS

(71) Applicant: Pharmacyclics LLC, Sunnyvale, CA (US)

(72) Inventors: Joseph J. Buggy, Mountain View, CA (US); Laurence Elias, Berkeley, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,366

(22) Filed: Jul. 7, 2015

(65) Prior Publication Data

US 2016/0000792 A1    Jan. 7, 2016

Related U.S. Application Data

(63) Continuation of application No. 13/965,135, filed on Aug. 12, 2013, now Pat. No. 9,107,924, which is a
(Continued)

(51) Int. Cl.
*A61K 31/519* (2006.01)
*A61P 35/00* (2006.01)
(Continued)

(52) U.S. Cl.
CPC .......... *A61K 31/519* (2013.01); *A61K 31/00* (2013.01); *A61K 31/337* (2013.01); *A61K 31/52* (2013.01);
(Continued)

(58) Field of Classification Search
CPC .. A61K 31/195; A61K 31/436; A61K 31/454; A61K 31/475; A61K 31/519; A61K 31/573; A61K 31/606; A61K 31/675; A61K 31/69; A61K 31/704; A61K 31/7076; A61K 31/337; A61K 31/4184; A61K 39/395;
(Continued)

(56) References Cited

U.S. PATENT DOCUMENTS 5,397,787 A    3/1995    Buzzetti et al.
5,593,997 A    1/1997    Dow et al.
(Continued)

FOREIGN PATENT DOCUMENTS

CA    2847852 A1    4/2008
CN    103923084 A    7/2014
(Continued)

OTHER PUBLICATIONS

Anderson (Chem and Biol 10:787-797, 2003.*
(Continued)

*Primary Examiner* — Savitha Rao
(74) *Attorney, Agent, or Firm* — Foley Hoag LLP

(57) ABSTRACT

Described herein are irreversible Btk inhibitor compounds, and methods for using such irreversible inhibitors in the treatment of diseases and disorders characterized by the presence or development of solid tumors.

22 Claims, 24 Drawing Sheets

Related U.S. Application Data continuation-in-part of application No. 13/341,708, filed on Dec. 30, 2011, now Pat. No. 8,883,803, and a continuation-in-part of application No. 13/341,695, filed on Dec. 30, 2011, now Pat. No. 9,278,100, said application No. 13/341,708 is a continuation of application No. 13/003,811, filed on May 25, 2011, said application No. 13/341,695 is a continuation of application No. 13/003,811, filed as application No. PCT/US2009/050897 on Jul. 16, 2009.

(60) Provisional application No. 61/081,344, filed on Jul. 16, 2008.

(51) Int. Cl.

| | | |
|---|---|---|
| *A61P 29/00* | (2006.01) | |
| *A61P 35/02* | (2006.01) | |
| *C07D 487/04* | (2006.01) | |
| *A61K 31/00* | (2006.01) | |
| *A61K 31/52* | (2006.01) | |
| *A61K 31/337* | (2006.01) | |
| *A61K 31/675* | (2006.01) | |
| *A61K 31/704* | (2006.01) | |
| *A61K 33/24* | (2006.01) | |
| *A61K 39/395* | (2006.01) | |
| *A61K 45/06* | (2006.01) | |

(52) U.S. Cl.
CPC .......... *A61K 31/675* (2013.01); *A61K 31/704* (2013.01); *A61K 33/24* (2013.01); *A61K 39/3955* (2013.01); *A61K 39/39558* (2013.01); *A61K 45/06* (2013.01)

(58) Field of Classification Search
CPC ... A61K 39/3955; A61K 45/06; C07D 487/04
See application file for complete search history.

(56) References Cited

U.S. PATENT DOCUMENTS

| | | | |
|---|---|---|---|
| 6,160,010 | A | 12/2000 | Uckun et al. |
| 6,221,900 | B1 | 4/2001 | Uckun et al. |
| 6,306,897 | B1 | 10/2001 | Uckun et al. |
| 6,326,469 | B1 | 12/2001 | Ullrich et al. |
| 6,506,769 | B2 | 1/2003 | Snow et al. |
| 6,660,744 | B1 | 12/2003 | Hirst et al. |
| 6,753,348 | B2 | 6/2004 | Uckun et al. |
| 6,770,639 | B2 | 8/2004 | Snow et al. |
| 6,921,763 | B2 | 7/2005 | Hirst et al. |
| 7,138,420 | B2 | 11/2006 | Bentzien et al. |
| 7,332,497 | B2 | 2/2008 | Hirst et al. |
| 7,514,444 | B2 | 4/2009 | Honigberg et al. |
| 7,718,662 | B1 | 5/2010 | Chen et al. |
| 7,732,454 | B2 | 6/2010 | Verner |
| 7,741,330 | B1 | 6/2010 | Chen et al. |
| 7,825,118 | B2 | 11/2010 | Honigberg et al. |
| 7,960,396 | B2 | 6/2011 | Honigberg et al. |
| 8,008,309 | B2 | 8/2011 | Honigberg et al. |
| 8,088,781 | B2 | 1/2012 | Honigberg et al. |
| 8,158,786 | B2 | 4/2012 | Honigberg et al. |
| 8,232,280 | B2 | 7/2012 | Honigberg et al. |
| 8,236,812 | B2 | 8/2012 | Honigberg et al. |
| 8,306,897 | B2 | 11/2012 | Yolles |
| 8,399,470 | B2 | 3/2013 | Honigberg et al. |
| 8,476,284 | B2 | 7/2013 | Honigberg et al. |
| 8,497,277 | B2 | 7/2013 | Honigberg et al. |
| 8,501,724 | B1 | 8/2013 | Chen et al. |
| 8,501,751 | B2 | 8/2013 | Honigberg et al. |
| 8,552,010 | B2 | 10/2013 | Honigberg et al. |
| 8,563,563 | B2 | 10/2013 | Honigberg et al. |
| 8,633,311 | B2 | 1/2014 | Bommer et al. |
| 8,642,604 | B2 | 2/2014 | Knight et al. |
| 8,658,653 | B2 | 2/2014 | Honigberg et al. |
| 8,691,546 | B2 | 4/2014 | Honigberg et al. |
| 8,697,711 | B2 | 4/2014 | Honigberg et al. |
| 8,703,780 | B2 | 4/2014 | Honigberg et al. |
| 8,735,403 | B2 | 5/2014 | Honigberg et al. |
| 8,735,404 | B2 | 5/2014 | Honigberg et al. |
| 8,741,908 | B2 | 6/2014 | Honigberg et al. |
| 8,748,438 | B2 | 6/2014 | Honigberg et al. |
| 8,748,439 | B2 | 6/2014 | Honigberg et al. |
| 8,754,090 | B2 | 6/2014 | Buggy et al. |
| 8,754,091 | B2 | 6/2014 | Honigberg et al. |
| 8,759,516 | B2 | 6/2014 | Honigberg et al. |
| 8,809,273 | B2 | 8/2014 | Honigberg et al. |
| 8,883,435 | B2 | 11/2014 | Honigberg et al. |
| 8,883,803 | B2 | 11/2014 | Honigberg et al. |
| 8,940,750 | B2 | 1/2015 | Honigberg et al. |
| 8,952,015 | B2 | 2/2015 | Honigberg et al. |
| 8,957,079 | B2 | 2/2015 | Honigberg et al. |
| 8,975,266 | B2 | 3/2015 | Honigberg et al. |
| 8,987,233 | B2 | 3/2015 | Pan et al. |
| 8,999,999 | B2 | 4/2015 | Buggy et al. |
| 9,012,463 | B2 | 4/2015 | Chen et al. |
| 9,079,908 | B2 | 7/2015 | Honigberg et al. |
| 9,107,924 | B2 | 8/2015 | Buggy et al. |
| 9,117,924 | B2 | 8/2015 | Kitagawa et al. |
| 9,125,889 | B2 | 9/2015 | Buggy |
| 9,127,012 | B2 | 9/2015 | Honigberg et al. |
| 9,133,198 | B2 | 9/2015 | Honigberg et al. |
| 9,133,201 | B2 | 9/2015 | Honigberg et al. |
| 9,133,202 | B2 | 9/2015 | Honigberg et al. |
| 9,139,591 | B2 | 9/2015 | Honigberg et al. |
| 9,181,257 | B2 | 11/2015 | Honigberg et al. |
| 9,181,263 | B2 | 11/2015 | Honigberg et al. |
| 9,193,735 | B2 | 11/2015 | Honigberg et al. |
| 9,206,189 | B2 | 12/2015 | Honigberg et al. |
| 9,212,185 | B2 | 12/2015 | Honigberg et al. |
| 9,266,893 | B2 | 2/2016 | Honigberg et al. |
| 9,278,100 | B2 | 3/2016 | Honigberg et al. |
| 9,296,753 | B2 | 3/2016 | Smyth et al. |
| 9,409,911 | B2 | 8/2016 | Honigberg et al. |
| 9,421,208 | B2 | 8/2016 | Balasubramanian |
| 9,540,382 | B2 | 1/2017 | Purro et al. |
| 2002/0016460 | A1 | 2/2002 | Snow et al. |
| 2002/0155505 | A1 | 10/2002 | Wells et al. |
| 2003/0013125 | A1 | 1/2003 | Braisted et al. |
| 2003/0035833 | A1 | 2/2003 | He |
| 2003/0040461 | A1 | 2/2003 | McAtee |
| 2003/0125235 | A1 | 7/2003 | Foxwell |
| 2004/0006083 | A1 | 1/2004 | Hirst et al. |
| 2005/0008640 | A1 | 1/2005 | Waegell et al. |
| 2005/0084905 | A1 | 4/2005 | Prescott et al. |
| 2005/0090499 | A1 | 4/2005 | Currie et al. |
| 2005/0101604 | A1 | 5/2005 | Currie et al. |
| 2005/0196851 | A1 | 9/2005 | Uckun |
| 2005/0209255 | A1 | 9/2005 | Jimenez et al. |
| 2006/0079494 | A1 | 4/2006 | Santi et al. |
| 2006/0167090 | A1 | 7/2006 | Uckun et al. |
| 2006/0178367 | A1 | 8/2006 | Currie et al. |
| 2007/0065449 | A1 | 3/2007 | Verschraegen |
| 2007/0105136 | A1 | 5/2007 | Staudt et al. |
| 2007/0281907 | A1 | 12/2007 | Watkins |
| 2008/0108636 | A1 | 5/2008 | Honigberg et al. |
| 2008/0214501 | A1 | 9/2008 | Pan et al. |
| 2009/0098137 | A1 | 4/2009 | Burke et al. |
| 2009/0105209 | A1 | 4/2009 | Dewdney et al. |
| 2009/0186898 | A1 | 7/2009 | Dewdney et al. |
| 2009/0317836 | A1 | 12/2009 | Kuhn et al. |
| 2010/0016296 | A1 | 1/2010 | Singh et al. |
| 2010/0022561 | A1 | 1/2010 | Honigberg et al. |
| 2010/0041677 | A1 | 2/2010 | Honigberg et al. |
| 2010/0087482 | A1 | 4/2010 | Haber et al. |
| 2010/0222325 | A1 | 9/2010 | Berthel et al. |
| 2010/0254905 | A1 | 10/2010 | Honigberg et al. |
| 2010/0324050 | A1 | 12/2010 | Honigberg et al. |
| 2011/0039868 | A1 | 2/2011 | Honigberg et al. |
| 2011/0086866 | A1 | 4/2011 | Chen et al. |
| 2011/0177011 | A1 | 7/2011 | Currie et al. |
| 2011/0224235 | A1 | 9/2011 | Honigberg et al. |
| 2011/0244465 | A1 | 10/2011 | Harvey et al. |

(56) References Cited

U.S. PATENT DOCUMENTS

| | | |
|---|---|---|
| 2011/0281322 A1 | 11/2011 | Honigberg et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0219522 A1 | 8/2012 | Xi |
| 2012/0252821 A1 | 10/2012 | Honigberg et al. |
| 2012/0252822 A1 | 10/2012 | Honigberg et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0018060 A1 | 1/2013 | Honigberg et al. |
| 2013/0035334 A1 | 2/2013 | Honigberg et al. |
| 2013/0041014 A1 | 2/2013 | Lavitrano et al. |
| 2013/0195852 A1 | 8/2013 | Buggy et al. |
| 2013/0202611 A1 | 8/2013 | Buggy et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0057907 A1 | 2/2014 | Honigberg et al. |
| 2014/0128413 A1 | 5/2014 | Honigberg et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194446 A1 | 7/2014 | Buggy et al. |
| 2014/0212485 A1 | 7/2014 | Honigberg et al. |
| 2014/0243355 A1 | 8/2014 | Honigberg et al. |
| 2014/0303191 A1 | 10/2014 | Buggy et al. |
| 2014/0336206 A1 | 11/2014 | Honigberg et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0118222 A1 | 4/2015 | Levy et al. |
| 2015/0133661 A1 | 5/2015 | Honigberg et al. |
| 2015/0140036 A1 | 5/2015 | Mannick et al. |
| 2015/0152115 A1 | 6/2015 | Honigberg et al. |
| 2015/0158871 A1 | 6/2015 | Purro et al. |
| 2015/0238490 A1 | 8/2015 | Burger |
| 2015/0239897 A1 | 8/2015 | Chen et al. |
| 2016/0243033 A1 | 8/2016 | Buggy et al. |

FOREIGN PATENT DOCUMENTS

| | | |
|---|---|---|
| EP | 1473039 A1 | 11/2004 |
| WO | WO-9728161 A1 | 8/1997 |
| WO | WO-9954286 A2 | 10/1999 |
| WO | WO-0000823 A1 | 1/2000 |
| WO | WO-0056737 A2 | 9/2000 |
| WO | WO-0119829 A2 | 3/2001 |
| WO | WO-0125238 A2 | 4/2001 |
| WO | WO-0141754 A2 | 6/2001 |
| WO | WO-0144258 A1 | 6/2001 |
| WO | WO-0119829 A3 | 9/2001 |
| WO | WO-0238797 A2 | 5/2002 |
| WO | WO-02076986 A1 | 10/2002 |
| WO | WO-02080926 A1 | 10/2002 |
| WO | WO-03000187 A2 | 1/2003 |
| WO | WO-03013540 A1 | 2/2003 |
| WO | WO-03046200 A2 | 6/2003 |
| WO | WO-03097645 A1 | 11/2003 |
| WO | WO-2004074290 A1 | 9/2004 |
| WO | WO-2004096253 A1 | 11/2004 |
| WO | WO-2004100868 A2 | 11/2004 |
| WO | WO-2005000197 A2 | 1/2005 |
| WO | WO-2005005429 A1 | 1/2005 |
| WO | WO-2005014599 A1 | 2/2005 |
| WO | WO-2005037843 A1 | 4/2005 |
| WO | WO-2004100868 A3 | 7/2005 |
| WO | WO-2005060956 A1 | 7/2005 |
| WO | WO-2005074603 A2 | 8/2005 |
| WO | WO-2006/036788 A2 | 4/2006 |
| WO | WO-2006/036941 A2 | 4/2006 |
| WO | WO-2006036527 A1 | 4/2006 |
| WO | WO-2006050946 A1 | 5/2006 |
| WO | WO-2006053121 A2 | 5/2006 |
| WO | WO-2006099075 A2 | 9/2006 |
| WO | WO-2006124462 A2 | 11/2006 |
| WO | WO-2007002325 A1 | 1/2007 |
| WO | WO-2007058832 A2 | 5/2007 |
| WO | WO-2007087068 A2 | 8/2007 |
| WO | WO-2007136790 A2 | 11/2007 |
| WO | WO-2008039218 A2 | 4/2008 |
| WO | WO-2008054827 A2 | 5/2008 |
| WO | WO-2008/108636 A1 | 9/2008 |
| WO | WO-2008/124138 A1 | 10/2008 |
| WO | WO-2008121742 A2 | 10/2008 |
| WO | WO-2009051822 A1 | 4/2009 |
| WO | WO-2009158571 A1 | 12/2009 |
| WO | WO-2010009342 A3 | 5/2010 |
| WO | WO-2010/065898 A2 | 6/2010 |
| WO | WO-2010126960 A1 | 11/2010 |
| WO | WO-2011034907 A2 | 3/2011 |
| WO | WO-2011153514 A2 | 12/2011 |
| WO | WO-2011162515 A2 | 12/2011 |
| WO | WO-2012021444 A1 | 2/2012 |
| WO | WO-2012/158764 A1 | 11/2012 |
| WO | WO-2013/059738 A2 | 4/2013 |
| WO | WO-2014/004707 A1 | 1/2014 |
| WO | WO-2014/018567 A1 | 1/2014 |
| WO | WO-2014/135669 A1 | 9/2014 |
| WO | WO-2014/168975 A1 | 10/2014 |
| WO | WO-2015/127234 A1 | 8/2015 |

OTHER PUBLICATIONS

Thiel (Nature Biotechnol 2:513-519, 2004).*
Baselga (Science 26, May 2006, vol. 312. No. 5777, pp. 1175-1178.*
Iqbal et al. on pp. 2-4 (Molecular biology international, 2014, Article ID 852748, 9 pages.*
Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
ACS 2015 (http://www.cancer.org/cancer/non-hodgkinlymphoma/detailedguide/non-hodgkin-lymphoma-types-of-non-hodgkinlymphoma).
Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).

(56) References Cited

OTHER PUBLICATIONS

Advani et al. The BTK inhibitor PCI-32765 is highly active and well tolerated in patients (PTS) with relapsed/refractory B cell malignancies: final results from a phase I study, Ann. Oncol. 22(suppl 4): abstract 153 (2011).
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Ahn et al. Michael acceptors as a tool for anticancer drug design. Current Pharmaceutical Design 2(3):247-262 (1996).
American Cancer Society Melanoma Guidelines (Last Revised Sep. 5, 2014), p. 37.
Anderson. The process of structure-based drug design. Chem and Biol 10:787-797 (2003).
Apsel et al. Targeted Polypharmacology: Discovery of Dual Inhibitors of Tyrosine and Phosphoinositide Kinases. Nature Chem. Bio., 4(11):691-699 (2008).
Banker et al. Modern Pharmaceutics, 3ed., Marcel Dekker, New York 1996, p. 596.
Baselga. Targeting tyrosine kinases in cancer: the second wave. Science 312(5777):1175-1178 (2006).
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl):abstract 8032 (2012); [online][retrieved on Oct. 4, 2012] Retrieved from the Internet: < http://www.asco.org/ASCOv2/Meetings/Abstracts?&vmview=abst_detail_view&confID=114&abstractID=98841>.
Browning. B cells move to centre stage: novel opportunities for autoimmune disease treatment. Nature Reviews/Drug Discovery 5:564-576 (Jul. 2006).
Burger. Targeting the microenvironment in chronic lymphocytic leukemia is changing the therapeutic landscape. Curr. Opin. Oncol. 24(6):643-649 (Epub Sep. 6, 2012/Nov. 2012).
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Chang et al. The Bruton tyrosine kinase inhibitor PCI-32765 ameliorates autoimmune arthritis by inhibition of multiple effector cells. Arthritis Research & Therapy, 13:R115 (2011).
Chang et al. PCI-45292, a Novel Btk Inhibitor with Optimized Pharmaceutical Properties, Demonstrates Potent Activities in Rodent Models of Arthritis. ACR/ARHP Scientific Meeting, Nov. 6-11, 2010, Poster #286.
Chen et al. SYK-dependent tonic B-cell receptor signaling is a rational treatment target in diffuse large B-cell lymphoma. Blood 111(4):2230-2237 (2008) [E-pub Nov. 15, 2007].
Cohen et al. Structural Bioinformatics-Based Design of Selective, Irreversible Kinase Inhibitors. Science 308:1318-1321 (May 27, 2005).
Co-pending U.S. Appl. No. 14/605,857, filed Jan. 26, 2015.
Co-pending U.S. Appl. No. 14/613,309, filed Feb. 3, 2015.
Co-pending U.S. Appl. No. 14/703,750, filed May 4, 2015.
Co-pending U.S. Appl. No. 14/794,685, filed Jul. 8, 2015.
Czuczman et al. Rituximab in combination with fludarabine chemotherapy in low-grade or follicular lymphoma. J. Clin. Oncol. 23(4):694-704 (Feb. 1, 2005).
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al. Chronic active B-cell receptor signalling in diffuse large B-cell lymphoma. Nature 463(7277):88-94 (2010).
D'Cruz et al. Novel Bruton's tyrosine kinase inhibitors currently in development. OncoTargets and Therapy 6:161-176 (2013).
Desiderio. Role of Btk in B cell development and signaling. Curr. Op. in Immunology 1997, 9:534-540.
Dorwald. A. Side Reactions in Organic Synthesis, Wiley:VCH, Weinheim p. IX of Preface, Wiley-VCH Verlag GmbH & Co. KGaA (2005).
Edwards. BTK inhibition in myeloma: targeting the seed and the soil. Blood 120(9):1757-1759 (Aug. 2012).
Expert Scientific Group on Phase One Clinical Trials. Final Report. Nov. 2006, pp. C1, C35-C38.
Fabian et al. A small molecule-kinase interaction map for clinical kinase inhibitors. Nature Biotechnology, 23(3): 329-336 (2005).
Fisher et al. Prolonged disease-free survival in Hodgkin's disease with MOPP reinduction after first relapse. Ann. Intern. Med., 90(5):761-763 (1979).
Fowler et al. The Bruton's tyrosine kinase inhibitor ibrutinib (PCI-32765) is active and tolerated in relapsed follicular lymphoma. 54th American Society of Hematology Annual Meeting and Exposition, Atlanta, GA, Abstract 156 (Dec. 8-11, 2012).
Friedberg et al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].
Fruman. Xid-like Phenotypes: A B Cell Signalosome Takes Shape. Immunity 13:1-3 (Jul. 2000).
Giuliani. Multiple myeloma bone disease: pathophysiology of osteoblast inhibition. Blood (Epub Aug. 17, 2006) 108(13):3992-3996 (2006).
Glassman et al. The value of fluorescence in situ hybridization in the diagnosis and prognosis of chronic lymphocytic leukemia, Cancer Genetics and Cytogenetics 158:88-91 (2005).
Gold. To make antibodies or not:signaling by the B-cell antigen receptor. Trends in Pharmacological Sciences, 23(7):316-324 (Jul. 2002).
Gordon et al. Somatic hypermutation of the B cell receptor genes B29 (Igb, CD79b) and mb1 (Iga, CD79a). PNAS 100(7):4126-4131 (2003).
Gura. Systems for Identifiiying New Drugs Are Often Faulty. Science 278(5340):1041-1042 (1997).
Hagemeister. Rituximab for the treatment of non-Hodgkin's lymphoma and chronic lymphocytic leukaemia. Drugs 70(3):261-272 (2010).
Hantschel et al. The Btk Tyrosine Kinase is a Major Target of the Bcr-Ab1 Inhibitor Dasatinib. PNAS 104(33):13283-13288 (2007).
Hata et al. Bruton's tyrosine kinase-mediated Interleukin-2 gene activation in mast cells. J. Biol. Chem. 273(18): 10979-10987 (1998).
Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group. Blood (Epub Aug. 25, 2005) 106(12):3725-3732 (Dec. 2005).
Hiddeman et al. Rituximab Plus Chemotherapy in Follicular and Mantle Cell Lymphomas, Seminars in Oncology 30(1)Suppl.2:16-20 (Feb. 2003).
Horwood et al. Bruton's Tyrosin Kinase Is Required for Lipopolysaccharide-induced Tumor Necrosis Factor α Production. J. Exp. Med. 197(12):1603-1611 (Jun. 2003).
http://www.uspto.gov/web/offices/pac/dapp/1pecba.htm#7, Last accessed Feb. 16, 2011.
Huhn et al. Rituximab therapy of patients with B-cell chronic lymphocytic leukemia. Blood 98(5):1326-1331 (Sep. 1, 2001).
Iwaki et al. Btk Plays a Crucial Role in the Amplification of FceRI-mediated Mast Cell Activation by Kit. J. Biol. Chem. 280(48):40261-40270 (Dec. 2, 2005).
Jefferies et al. Bruton's Tyrosine Kinase Is a Toll/Interleukin-1 Receptor Domain-binding Protein That Participates in Nuclear Factor κB Activation by Toll-like Receptor 4. J. Biol. Chem. 278:26258-26264 (2003).

(56) References Cited

OTHER PUBLICATIONS

Kamb. What's wrong with our cancer models? Nature Reviews Drug Discovery 4:161-165 (2005).
Kawakami et al. Terreic acid, a quinone epoxide inhibitor of Bruton's tyrosine kinase. PNAS USA 96:2227-2232 (1999).
Kola et al. Can the pharmaceutical industry reduce attrition rates? Nature Reviews Drug Discover 3:711-715 (2004).
Korade-Mirnics et al. Src kinase-mediated signaling in leukocytes. J. Leukoc. Bio., 68(5):603-613 (Nov. 2000).
Kozaki et al. Development of a Bruton's tyrosine kinase (Btk) inhibitor—ONO-WG-307, a potential treatment for B-cell malignancies. 53rd American Society of Hematology Annual Meeting and Exposition, San Diego, CA, Poster #857 (Dec. 10-13, 2011).
Kuglstatter et al. Insights into the conformational flexibility of Bruton's tyrosine kinase from multiple ligand complex structures. Protein Science 20(2):428-436 (2011) [E-pub Dec. 17, 2010].
Kuppers. Mechanisms of B-cell lymphoma pathogenesis. Nature Reviews/Cancer 5:251-262 (2005).
Kurosaki. Functional dissection of BCR signaling pathways. Curr. Op. Imm. 12:276-281 (2000).
Leaf. Why Are We Losing the War on Cancer (And How to Win It). Health Admin. V. XVII, No. 1, pp. 172-183 (2005).
Li et al. Activation of Bruton's Tyrosine Kinase (BTK) by a Point Mutation in its Pleckstrin Homology (PH) domain. Immunity 2:451-460 (1995).
Lichtman. Battling the hematological malignancies: The 200 years' war. The Oncologist 13:126-138 (2008).
Liu et al. Structural Basis for selective inhibition of Src family kinases by PPI. Chemistry and Biology 6:671-678, in particular table 1, p. 671 (1999).
Lossos. Molecular Pathogenesis of Diffuse Large B-Cell Lymphoma. J. Clin. Oncol. 23(26):6351-6357 (Sep. 10, 2005).
Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.
Luskova et al. Modulation of the Fcε Receptor I Signaling by Tyrosin Kinase Inhibitors: Search for Therapeutic Targets of Inflammatory and Allergy Diseases. Curr. Pharmaceutical Design 10:1727-1737 (2004).
Mahajan et al. Rational Design and Synthesis of a Novel Anti-leukemic Agent Targeting Bruton's Tyrosine Kinase (BTK), LFM-A13 [α-Cyano-β-Methyl-N-(2,5-Dibromophenyl)Propenamide]. J. of Biol. Chem. 274(14):9587-9599 (1999).
Mallis et al. Structural characterization of a proline-driven conformational switch within the Itk SH2 domain. Nat. Struct. Biol., 9(12):900-905 (2002).
Mangla et al. Pleiotropic consequences of Bruton tyrosin kinase deficiency in myeloid lineages lead to poor inflammatory responses. Blood 104(4):1191-1197 (2004).
Marina et al. Biology and Therapeutic Advances for Pediatric Osteosarcoma. The Oncologist 9:422-441 (2004).
Mendel et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9(1):327-337 (2003).
Merged Markush Service Search, Jun. 27, 2005.
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Mukoyama et al. Preparation of imidazol [1,5-a]pyrazine derivatives, pharmaceutical compositions containing them, and their uses for prevention or treatment of protein tyrosine kinase-related diseases, retrieved from STN Database Accession No. 2005:299462 Patent No. JP2005089352, Apr. 7, 2005, *abstract*.
Neidle. Cancer Drug Design and Discovery. Elsevier/Academic Press. pp. 427-431 (2008).
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Oligino et al. Targeting B cells for the treatment of rheumatoid arthritis. Arthritis Res. Ther., 5(Suppl.4):S7-S11 (2002).
Pagel et al. Induction of apoptosis using inhibitors of lysophosphatidic acid acyltransferase-beta and anti-CD20 monoclonal antibodies for treatment of human non-Hodgkin's lymphomas. Clin. Cancer Res. (Epub Jul. 6, 2005), 11(13):4857-4866 (2005).
Pan et al. Discovery of Selective Irreversible Inhibitors for Bruton's Tyrosine Kinase, ChemMedChem. 2:58-61 (2007).
PCT/US2006/49626 International Preliminary Report on Patentability Search Report dated Mar. 24, 2009.
PCT/US2006/49626 International Search Report dated Apr. 9, 2008.
PCT/US2008/058528 International Search Report and Written Opinion dated Sep. 30, 2008.
PCT/US2009/50897 International Preliminary Examination Report and Written Opinion dated Jan. 27, 2011.
PCT/US2009/50897 International Search Report dated Mar. 15, 2010.
PCT/US2010/52377 International Search Report and Written Opinion dated Jun. 29, 2011.
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Picci. Osteosarcoma (Osteogenic Sarcoma). Orphanet J. Rare Diseases 2(6):1-4 (2007).
Pollyea et al. A Phase I Dose Escalation Study of the Btk Inhibitor PCI-32765 in Relapsed and Refractory B Cell Non-Hodgkin Lymphoma and Use of a Novel Fluorescent Probe Pharmacodynamic Assay, Poster Abstract #3713, 51st ASH Annual Meeting and Exposition (Dec. 3, 2009).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Powers et al. Irreversible Inhibitors of Serine, Cysteine, and Threonine Proteases. Chem. Rev., 102(12):4639-4750 (2002).
Prakash et al. Chicken sarcoma to human cancers: a lesson in molecular therapeutics. The Ochsner Journal, 7(2):61-64 (Jan. 1, 2007).
PRNewswire. Pharmacyclics, Inc. Announces Presentation of Interim Results from Phase I Trial of its First-in-Human Btk Inhibitor PCI-32765. Dec. 7, 2009.
PRNewswire. Update on Preclinical Finding and Development Timeline for PCI-45292. Mar. 2, 2011.
Quek et al. A role for Bruton's tyrosine kinase (Btk) in platelet activation by collagen. Curr. Biol. 8(20):1137-1140 (1998).
Rao et al. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408 (2005).
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Roberts, Jr. et al. Trends in the Risks and Benefits to Patients With Cancer Participating in Phase 1 Clinical Trials. JAMA 292(17):2130-2140 (2004).
Rushworth et al. BTK inhibitor ibrutinib is cytotoxic to myeloma and potently enhances bortezomib and lenalidomide activities through NF-κB. Cell Signal. Sep. 11, 2012. pii: S0898-6568(12)00250-1. doi: 10.1016/j.cellsig.2012.09.008. [Epub ahead of print].

(56) References Cited

OTHER PUBLICATIONS

Rushworth et al. BTK inhibitor ibrutinib is cytotoxic to myeloma and potently enhances bortezomib and lenalidomide activities through NF-κB. Cell Signal (Epub Sep. 11, 2012), 25(1):106-112 (Jan. 2013).
Sada et al. Protein-Tyrosine Kinases and Adaptor Proteins in FceRI-Mediated Signaling in Mast Cells. Curr. Mol. Med. 3(1):85-94 (2003).
Schaeffer et al. Tec family kinases in lymphocyte signaling and function. Curr. Op. Imm. 12:282-288 (2000).
Schnute et al. Bruton's tyrosine kinase (Btk). Anti-Inflammatory Drug Discovery. Ed. J.I. Levin and S. Laufer. (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).
Science Daily. Counting tumor cells in blood predicts treatment benefit in prostate cancer. (Jul. 7, 2008), http://www.sciencedaily.com/releases/2008/07/080706083142.htm. last accessed Jul. 23, 2013.
Science Daily. Drug shows surprising efficacy as treatment for chronic leukemia, mantle cell lymphoma. (Jun. 19, 2013), http://www.sciencedaily.com/releases/2013/06/130619195217.htm, last accessed Jan. 30, 2014.
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Smaill et al. Tyrosine Kinase Inhibitors. 15. 4-(Phenylamino)quinazoline and 4-(Phenylamino)prido[d]pyrimidine Acrylamides as Irreversible Inhibitors of the ATP Binding Site of the Epidermal Growth Factor Receptor. J. Med. Chem. 42(10):1803-1815 (1999).
Smith et al. The Tec family of cytoplasmic tyrosine kinases: mammalian Btk, Bmx, Itk, Tec, Txk and homologs in other species. BioEssays 23:436-446 (2001).
Smolen et al. Therapeutic Strategies for Rheumatoid Arthritis. Nature Reviews 2:473-488 (2003).
STN Registry No. 936563-96-1. Ibrutinib. Retrieved from STN Registry Jul. 27, 2015. 1 pg.
Strimbu et al. What are biomarkers? Curr Opin HIV AIDS 5(6):463-466 (2010.
Theil. Structure-aided drug design's next generation. Nature Biotechnol 2:513-519 (2004).
Tinmouth et al. Fludarabine in alkylator-resistant follicular non-Hodgkin's lymphoma. Leuk. Lymphoma 41(1-2):137-145 (2001).
Traxler et al. Use of a Pharmacophore Model for the Design of EGR-R Tyrosine Kinase Inhibitors: 4-(Phenylamino)pyrazolo[3,4-d]pyrimidines. J. Med Chem 40(22):3601-3616 (1997).
Uckun et al. Bruton's tyrosine kinase as a molecular target in treatment of leukemias and lymphomas as well as inflammatory disorders and autoimmunity. Expert Opinion Ther. Patents 20(11):4157-1470 (2010).
Uckun et al. Bruton's Tyrosine Kinase (BTK) as a Dual-Function Regulator of Apoptosis. Biochem. Pharmacology 56:683-691 (1998).
Uckun et al. BTK as a Mediator of Radiation-Induced Apoptosis in DT-40 Lymphoma B Cells. Science 273(5278):1096-1100 (1996).
Uckun et al. In Vivo Pharmacokinetic Features, Toxicity Profile, and Chemosensitizing Activity of α-Cyano-β-hydroxy-β-methyl-N-(2,5-dibromophenyl)propenamide (LFM-A13), a Novel Antileukemic Agent Targeting Bruton's Tyrosine Kinase. Clin. Cancer Res. 8:1224-1233 (2002).
Uckun et al. The Anti-leukemic Bruton's Tyrosin Kinase Inhibitor α-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
U.S. Appl. No. 11/617,645 Final Office Action dated Oct. 16, 2008.
U.S. Appl. No. 11/617,645 Notice of Allowance dated Feb. 9, 2009.
U.S. Appl. No. 11/617,645 Office Action dated Jan. 24, 2008.
U.S. Appl. No. 11/617,645 Office Action dated May 13, 2008.
U.S. Appl. No. 11/692,870 Final Office Action dated Aug. 19, 2009.
U.S. Appl. No. 11/692,870 Office Action dated Jan. 26, 2009.
U.S. Appl. No. 12/356,498 Final Office Action dated Jul. 8, 2011.
U.S. Appl. No. 12/356,498 Office Action dated Apr. 14, 2011.
U.S. Appl. No. 12/499,002 Final Office Action dated Dec. 14, 2012.
U.S. Appl. No. 12/499,002 Final Office Action dated Oct. 25, 2011.
U.S. Appl. No. 12/499,002 Office Action dated Mar. 3, 2011.
U.S. Appl. No. 12/499,002 Office Action dated Jun. 5, 2012.
U.S. Appl. No. 12/499,005 Office Action dated Feb. 17, 2011.
U.S. Appl. No. 12/499,008 Office Action dated Jul. 19, 2011.
U.S. Appl. No. 12/499,008 Office Action dated Mar. 9, 2011.
U.S. Appl. No. 12/594,805 Final Office Action dated Jun. 27, 2013.
U.S. Appl. No. 12/594,805 Office Action dated Oct. 15, 2012.
U.S. Appl. No. 12/727,703 Final Office Action dated Jul. 19, 2011.
U.S. Appl. No. 12/727,703 Office Action dated Mar. 3, 2011.
U.S. Appl. No. 12/887,428 Office Action dated Apr. 20, 2011.
U.S. Appl. No. 12/907,759 Final Office Action dated Nov. 8, 2013.
U.S. Appl. No. 12/907,759 Office Action dated Aug. 13, 2013.
U.S. Appl. No. 12/907,759 Office Action dated Dec. 31, 2013.
U.S. Appl. No. 12/907,759 Office Action dated Jul. 10, 2014.
U.S. Appl. No. 13/003,811 Final Office Action dated Oct. 11, 2013.
U.S. Appl. No. 13/003,811 Non-Final Office Action dated Aug. 3, 2015.
U.S. Appl. No. 13/003,811 Office Action dated Feb. 25, 2013.
U.S. Appl. No. 13/011,258 Office Action dated Nov. 22, 2011.
U.S. Appl. No. 13/153,291 Final Office Action dated Mar. 26, 2015.
U.S. Appl. No. 13/153,291 Final Office Action dated Jan. 3, 2014.
U.S. Appl. No. 13/153,291 Office Action dated Jul. 18, 2014.
U.S. Appl. No. 13/153,291 Office Action dated Jul. 5, 2013.
U.S. Appl. No. 13/153,317 Final Office Action dated Jan. 23, 2014.
U.S. Appl. No. 13/153,317 Non-Final Office Action dated Jul. 23, 2015.
U.S. Appl. No. 13/153,317 Office Action dated Jul. 29, 2013.
U.S. Appl. No. 13/162,449 Office Action dated Feb. 9, 2012.
U.S. Appl. No. 13/232,784 Office Action dated Mar. 6, 2014.
U.S. Appl. No. 13/232,784 Office Action dated Sep. 15, 2014.
U.S. Appl. No. 13/249,066 Final Office Action dated May 15, 2013.
U.S. Appl. No. 13/249,066 Office Action dated Dec. 11, 2013.
U.S. Appl. No. 13/249,066 Office Action dated Nov. 27, 2012.
U.S. Appl. No. 13/312,606 Final Office Action dated Apr. 5, 2013.
U.S. Appl. No. 13/312,606 Office Action dated Sep. 19, 2012.
U.S. Appl. No. 13/328,718 Final Office Action dated Dec. 27, 2012.
U.S. Appl. No. 13/328,718 Office Action dated Jul. 3, 2012.
U.S. Appl. No. 13/335,719 Final Office Action dated Nov. 8, 2013.
U.S. Appl. No. 13/335,719 Office Action dated Jul. 31, 2013.
U.S. Appl. No. 13/340,276 Final Office Action dated Apr. 4, 2013.
U.S. Appl. No. 13/340,276 Office Action dated Sep. 10, 2013.
U.S. Appl. No. 13/340,276 Office Action dated Sep. 26, 2012.
U.S. Appl. No. 13/340,409 Final Office Action dated Nov. 12, 2013.
U.S. Appl. No. 13/340,409 Office Action dated Jul. 19, 2013.
U.S. Appl. No. 13/340,522 Final Office Action dated Nov. 1, 2013.
U.S. Appl. No. 13/340,522 Office Action dated Mar. 13, 2013.
U.S. Appl. No. 13/340,522 Response to Final Office Action, dated Dec. 17, 2013.
U.S. Appl. No. 13/340,533 Final Office Action dated Feb. 25, 2013.
U.S. Appl. No. 13/340,556 Office Action dated Jul. 31, 2013.
U.S. Appl. No. 13/340,559 Office Action dated Mar. 17, 2014.
U.S. Appl. No. 13/340,559 Office Action dated Sep. 26, 2014.
U.S. Appl. No. 13/340,621 Office Action dated Mar. 6, 2014.
U.S. Appl. No. 13/340,621 Office Action dated Sep. 26, 2014.
U.S. Appl. No. 13/341,695 Final Office Action dated Jun. 7, 2013.
U.S. Appl. No. 13/341,695 office Action dated Jun. 11, 2015.
U.S. Appl. No. 13/341,695 Office Action dated Feb. 1, 2013.
U.S. Appl. No. 13/341,695 Office Action dated Oct. 31, 2014.
U.S. Appl. No. 13/341,708 Office Action dated Jan. 22, 2014.
U.S. Appl. No. 13/361,726 Office Action dated Jul. 18, 2013.
U.S. Appl. No. 13/361,733 Notice of Allowance dated Nov. 14, 2012.
U.S. Appl. No. 13/361,733 Office Action dated Jul. 6, 2012.
U.S. Appl. No. 13/404,422 Final Office Action dated Aug. 12, 2015.
U.S. Appl. No. 13/404,422 Final Office Action dated Apr. 16, 2013.
U.S. Appl. No. 13/404,422 Non-Final Action dated Feb. 11, 2015.
U.S. Appl. No. 13/404,422 Office Action dated Feb. 21, 2014.

(56) References Cited

OTHER PUBLICATIONS

U.S. Appl. No. 13/404,422 Office Action dated Sep. 28, 2012.
U.S. Appl. No. 13/410,110 Final Office Action dated Jun. 12, 2015.
U.S. Appl. No. 13/410,110 Final Office Action dated Apr. 16, 2013.
U.S. Appl. No. 13/410,110 Non-Final Office Action dated Feb. 4, 2015.
U.S. Appl. No. 13/410,110 Office Action dated Feb. 24, 2014.
U.S. Appl. No. 13/410,110 Office Action dated Sep. 28, 2012.
U.S. Appl. No. 13/410,110 Office Action dated Sep. 29, 2014.
U.S. Appl. No. 13/430,173 Final Office Action dated Jul. 2, 2015.
U.S. Appl. No. 13/430,173 Non-Final Office Action dated Mar. 19, 2015.
U.S. Appl. No. 13/430,173 Office Action dated Feb. 25, 2014.
U.S. Appl. No. 13/430,173 Office Action dated Sep. 9, 2014.
U.S. Appl. No. 13/439,775 Final Office Action dated Jun. 4, 2015.
U.S. Appl. No. 13/439,775 Final Office Action dated Jun. 17, 2013.
U.S. Appl. No. 13/439,775 Non-Final Action dated Feb. 10, 2015.
U.S. Appl. No. 13/439,775 Office Action dated Dec. 10, 2012.
U.S. Appl. No. 13/439,775 Office Action dated Mar. 6, 2014.
U.S. Appl. No. 13/439,775 Office Action dated Sep. 26, 2014.
U.S. Appl. No. 13/450,158 Non-Final Office Action dated Oct. 31, 2013.
U.S. Appl. No. 13/472,292 Office Action dated Mar. 13, 2013.
U.S. Appl. No. 13/479,053 Office Action dated Sep. 6, 2013.
U.S. Appl. No. 13/526,161 Final Office Action dated May 15, 2013.
U.S. Appl. No. 13/526,161 Office Action dated Nov. 27, 2012.
U.S. Appl. No. 13/526,161 Office Action dated Aug. 1, 2013.
U.S. Appl. No. 13/526,163 Final Office Action dated May 15, 2013.
U.S. Appl. No. 13/526,163 Office Action dated Aug. 2, 2013.
U.S. Appl. No. 13/526,163 Office Action dated Nov. 28, 2012.
U.S. Appl. No. 13/542,440 Non-Final Office Action dated Oct. 31, 2013.
U.S. Appl. No. 13/542,440 Office Action dated Jan. 7, 2014.
U.S. Appl. No. 13/543,065 Office Action dated Feb. 26, 2015.
U.S. Appl. No. 13/543,065 Office Action dated Mar. 25, 2014.
U.S. Appl. No. 13/543,065 Office Action dated Oct. 8, 2014.
U.S. Appl. No. 13/543,394 Office Action dated Feb. 27, 2015.
U.S. Appl. No. 13/543,394 Office Action dated Mar. 25, 2014.
U.S. Appl. No. 13/543,394 Office Action dated Oct. 9, 2014.
U.S. Appl. No. 13/543,399 Final Office Action dated Jan. 26, 2015.
U.S. Appl. No. 13/543,399 Office Action dated Mar. 26, 2014.
U.S. Appl. No. 13/543,399 Office Action dated Sep. 10, 2014.
U.S. Appl. No. 13/543,399 Office Action dated Sep. 24, 2014.
U.S. Appl. No. 13/606,949 Final Office Action dated Feb. 14, 2014.
U.S. Appl. No. 13/606,949 Non-Final Office Action dated Oct. 29, 2013.
U.S. Appl. No. 13/607,036 Final Office Action dated Jun. 24, 2013.
U.S. Appl. No. 13/607,036 Non-Final Office Action dated Mar. 10, 2015.
U.S. Appl. No. 13/607,036 Office Action dated Mar. 6, 2014.
U.S. Appl. No. 13/607,036 Office Action dated Nov. 14, 2012.
U.S. Appl. No. 13/607,036 Office Action dated Sep. 26, 2014.
U.S. Appl. No. 13/612,143 Final Office Action dated Dec. 5, 2014.
U.S. Appl. No. 13/612,143 Office Action dated Jun. 23, 2014.
U.S. Appl. No. 13/654,173 Office Action dated Apr. 7, 2014.
U.S. Appl. No. 13/736,812 Non-Final Office Action dated Sep. 10, 2015.
U.S. Appl. No. 13/736,812 Office Action dated Mar. 18, 2014.
U.S. Appl. No. 13/736,812 Office Action dated Oct. 10, 2014.
U.S. Appl. No. 13/747,319 Office Action dated Mar. 20, 2014.
U.S. Appl. No. 13/747,319 Office Action dated Oct. 10, 2014.
U.S. Appl. No. 13/747,322 Office Action dated Mar. 20, 2014.
U.S. Appl. No. 13/849,399 Office Action dated Aug. 4, 2014.
U.S. Appl. No. 13/849,399 Office Action dated Jul. 23, 2014.
U.S. Appl. No. 13/869,700 Non-Final Office Action dated Sep. 10, 2015.
U.S. Appl. No. 13/869,700 Office Action dated May 16, 2014.
U.S. Appl. No. 13/869,700 Office Action dated Nov. 28, 2014.
U.S. Appl. No. 13/890,498 Non-Final Office Action dated Mar. 6, 2015.
U.S. Appl. No. 13/890,498 Office Action dated Aug. 19, 2014.
U.S. Appl. No. 13/908,949 Office Action dated Jun. 11, 2015.
U.S. Appl. No. 13/965,135 Office Action dated Dec. 22, 2014.
U.S. Appl. No. 14/033,344 Non-Final Office Action dated Dec. 10, 2014.
U.S. Appl. No. 14/069,222 Final Office Action dated Jun. 18, 2015.
U.S. Appl. No. 14/069,222 Office Action dated Oct. 9, 2014.
U.S. Appl. No. 14/073,543 Office Action dated Dec. 15, 2014.
U.S. Appl. No. 14/073,594 Final Office Action dated Jul. 1, 2015.
U.S. Appl. No. 14/073,594 Office Action dated Dec. 15, 2014.
U.S. Appl. No. 14/079,508 Office Action dated Dec. 15, 2014.
U.S. Appl. No. 14/080,640 Final Office Action dated May 13, 2015.
U.S. Appl. No. 14/080,640 Non-Final Office Action dated Feb. 24, 2015.
U.S. Appl. No. 14/080,640 Office Action dated Dec. 31, 2014.
U.S. Appl. No. 14/080,649 Final Office Action dated May 21, 2015.
U.S. Appl. No. 14/080,649 Office Action dated Feb. 5, 2015.
U.S. Appl. No. 14/091,196 Office Action dated May 19, 2015.
U.S. Appl. No. 14/152,886 Non-Final Office Action dated Apr. 23, 2015.
U.S. Appl. No. 14/156,247 Non-Final Office Action dated May 1, 2015.
U.S. Appl. No. 14/179,457 Final Office Action dated Dec. 22, 2014.
U.S. Appl. No. 14/179,457 Office Action dated Aug. 4, 2014.
U.S. Appl. No. 14/339,363 Office Action dated Jan. 12, 2015.
U.S. Appl. No. 14/340,483 Office Action dated May 5, 2015.
U.S. Appl. No. 14/448,963 Office Action dated Nov. 12, 2014.
U.S. Appl. No. 14/605,854 Non-Final Office Action dated May 27, 2015.
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Vose. Mantle cell lymphoma: 2012 update on diagnosis, risk-stratification, and clinical management. Am. J. Hematol. 87(6):604-609 (Jun. 2012).
Wang et al. Targeting BTK with ibrutinib in relapsed or refractory mantel-cell lymphoma. N Engl J Med 369(6):507-516 (Aug. 8, 2013).
Wilkinson et al. Selective tyrosine kinase inhibitors. Expert Opin. Emerging Drugs 5(3):287-297 (2000).
Witzens-Harig et al. Current treatment of mantle cell lymphoma: results of a national survey and consensus meeting. Ann Hematol. (Epub Aug. 29, 2012), 91(11):1765-1772 (Nov. 2012).
Witzig et al. Detection of myeloma cells in the peripheral blood by flow cytometry. Cytometry (Communications in Clinical Cytometry), 26:113-120 (1996).
Witzig et al. Lenalidomide oral monotherapy produces durable responses in relapsed or refractory indolent non-Hodgkin's lymphoma. J. Clin. Oncol. 27:5404-5409 (Epub Oct. 5, 2009).
Wolff. Burger's Medicinal Chemistry and Drug Discovery. 5th Ed. Part 1, pp. 975-977 (1995).
Woyach et al. Resistance mechanisms for the Bruton's tyrosine kinase inhibitor ibrutinib. N Engl J Med 370(24):2286-2294 (2014).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. and Exp. Therapeutics 306(3):1174-1181 (2003).
Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].
Yasuhiro et al. ONO-WG-307, a Novel, Potent and Selective Inhibitor of Bruton's Tyrosine Kinase, in sustained inhibition of the Erk, Akt and PKD signaling pathways. 53rd American Society of Hematology Annual Meeting and Exposition, San Diego, CA, Poster #2021 (Dec. 10-13, 2011).
Zent et al. The Treatment of Recurrent/Refractory chronic Lymphocytic Leukemia/Small Lymphocytic Lymphoma (CLL)

(56) References Cited

OTHER PUBLICATIONS

With Everolimus Results in Clinical Responses and Mobilization of CLL Cells Into the Circulation. Cancer 116(9):2201-2207 (2010).
Zhu et al. Calpain Inhibitor II Induces Caspase-dependent Apoptosis in Human Acute Lymphoblastic Leukemia and Non-Hodgkin's Lymphoma Cells as well as Some Solid Tumor Cells. Clin. Cancer Res. 6:2456-2463 (2000).
Adimoolam et al. HDAC inhibitor PCI-24781 decreases RAD51 expression and inhibits homologous recombination. PNAS 104 (49):19482-19487 (2007).
Advani, R.H., et al., 2013, "Bruton tyrosine kinase inhibitor Ibrutinib (PCI-32765) has significant activity in patients with relapsed/refractory B-cell malignancies", J. Clin. Oncol., vol. 31, No. 1 ,pp. 88-94.
Arkin et al. HER-2-directed, small-molecule antagonists. Curr Opin. Investig Drugs. 2008;9(12):1264-1276.
Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).
Asrani et al. The HER2- and heregulin β1 (HRG)-inducible Tnfr superfamily member Fn14 promotes HRG-driven breast cancer cell migration, invasion, and MMP9 expression. Mol Cancer Res. Apr. 2013;11(4):393-404. doi: 10.1158/1541-7786.MCR-12-0542. Epub Feb. 1, 2013.
Bhalla et al. PCI-24781 induces caspase and reactive oxygen species-dependent apoptosis through NF-kappaB mechanisms and is synergistic with bortezomib in lymphoma cells. Clin Cancer Res 15:3354-3365 (2009).
Biospace, Dec. 8, 2009, Pharmacyclics, Inc. (PCYC) announces presentation of interim results from phase I trial of its first-in-human btk inhibitor PCI-32765.
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger et al. The Btk Inhibitor Ibrutinib (PCI-32765) in Combination with Rituximab Is Well Tolerated and Displays Profound Activity in High-Risk Chronic Lymphocytic Leukemia (CLL) Patients. Blood (ASH Annual Meeting Abstracts).120:Abstract 187 (2012).
Byrd et al. Targeting BTK with Ibrutinib in relapsed chronic lymphocytic leukemia, NEJM 369(1):32-42 (Jul. 4, 2013).
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Chang et al. Egress of CD19+CD5+ cells into peripheral blood following treatment with the Bruton tyrosine kinase inhibitor ibrutinib in mantel cell lymphoma patients. Blood, 122:2412-2424 (2013).
Clinical Trial Report: NCT01105247 (NIH, USA), "Safety of PCI-32765 in Chronic Lymphocytic Leukemia."
Co-pending U.S. Appl. No. 14/856,217, filed Sep. 16, 2015.
Combination treatment of the Bruton's tyrosine kinase inhibitor ibrutinib and carfilzomib in patients with relapsed or relapsed and refractory multiple myeloma: initial results from a multicenter phase 1/2b study. NCT01962792 (2015).
Dana-Farber Cancer Institute. A Phase II Study of Ibrutinib Plus FCR in Previously Untreated, Younger Patients with Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/show/NCT02251548?term=NCT02251548 NLM Identifier: NCT02251548.
Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012—[cited Nov. 22, 2013]. Available from: http://clinicaltrials.gov/ct2/show/NCT01614821 NLM Identifier: NCT01614821.
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Dy et al., "Understanding, recognizing, and managing toxicities of targeted anticancer therapies," CA: A Cancer Journal for Clinicians, 63(4): 249-279 (2013).
Elias et al. BTK Inhibitor Ibrutinib Inhibits Breast Cancer Growth by Inhibiting ErbB Kinases. Mol Cancer Ther. 2013;12:C258. (not available on pubmed).
Eurasian Search Report for Eurasian Application No. EA201000599 dated Nov. 15, 2010.
European Examination Report for European Application No. EP 08744513.6 dated Jan. 16, 2013.
European Examination Report for European Application No. EP 12151943.3 dated Feb. 5, 2013.
European Examination Report for European Application No. EP 12166305.8 dated Dec. 3, 2013.
Extended European Search Report for European Application No. EP 12166301.7 dated Nov. 6, 2012.
Extended European Search Report for European Application No. EP 06850039.6 dated Feb. 15, 2010.
Extended European Search Report for European Application No. EP 06850386.1 dated Sep. 10, 2010.
Extended European Search Report for European Application No. EP 08744513.6 dated Mar. 18, 2010.
Extended European Search Report for European Application No. EP 09798770.5 dated Oct. 28, 2011.
Extended European Search Report for European Application No. EP 10155834.4 dated May 27, 2010.
Extended European Search Report for European Application No. EP 10823966.6 dated Oct. 17, 2011.
Extended European Search Report for European Application No. EP 12151943.3 dated Mar. 13, 2012.
Extended European Search Report for European Application No. EP 12166295.1 dated Nov. 6, 2012.
Extended European Search Report for European Application No. EP 12166296.9 dated Nov. 8, 2012.
Extended European Search Report for European Application No. EP 12166298.5 dated Nov. 7, 2012.
Extended European Search Report for European Application No. EP 12166300.9 dated Oct. 31, 2012.
Extended European Search Report for European Application No. EP 12166302.5 dated Nov. 6, 2012.
Extended European Search Report for European Application No. EP 12166305.8 dated Nov. 6, 2012.
Extended European Search Report for European Application No. EP 12166306.6 dated Nov. 8, 2012.
Extended European Search Report for European Application No. EP 12172840.6 dated Dec. 12, 2012.
Extended European Search Report for European Application No. EP 12172841.4 dated Jan. 2, 2013.
Extended European Search Report for European Application No. EP 12172842.2 dated May 14, 2013.
Extended European Search Report for European Application No. EP 12172843.0 dated Jan. 18, 2013.
Ezell S.A., et al., "Synergistic Induction of Apoptosis by Combination of BTK and Dual mTORC1/2 Inhibitors in Diffuse Large B Cell Lymphoma," Oncotarget, 2014, vol. 5 (13), pp. 4990-5001.
Fowler et al. The Btk Inhibitor, PCI-32765, Induces Durable Responses with Minimal Toxicity in Patients with Relapsed/Refractory B-Cell Malignancies: Results from a Phase 1 Study. Blood (ASH Annual Meeting) 116 (21), p. 425:Abstract 964 (2010).
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Ghia. Ibrutinib: better combined with other drugs? Lancet 15:1043-1044 (2014).

(56) References Cited

OTHER PUBLICATIONS

Grabinski et al., "Ibrutinib (Imbruvica™) Potently Inhibits ErbB Receptor Phosphorylation and Cell Viability of ErbB2-Positive Breast Cancer Cells," Invest New Drug, 32(6): 1096-1104 (Aug. 1, 2014).
Honigberg et al. The Bruton tyrosine kinase inhibitor Pci-32765 blocks B-cell activation and is efficacious in models of autoimmune disease and B-cell malignancy. PNAS USA 107:13075-13080 (2010).
Honigberg et al., Targeting Btk in Lymphoma: PCT-32765 Inhibits Tumor Growth in Mouse Lymphoma Models and a Fluorescent Analog of PCT-32765 Is an Active-Site Probe that Enables Assessment of Btk Inhibition in Vivo. Blood (Ash Annual Meeting Abstracts). 2007. 110: Abstract 1592.
Hurrell et al. The in vitro influences of epidermal growth factor and heregulin-β1 on the efficacy of trastuzumab used in Her-2 positive breast adenocarcinoma. Cancer Cell Int. Oct. 11, 2013;13(1):97. doi: 10.1186/1475-2867-13-97.
Inhibitory effects of the BTK inhibitor, ibrutinib, on HER2-amplified breast cancer growth, cell cycle progression, and clonogenicity—Poster.
International Preliminary Report on Patentability for International Application No. PCT/US2014/050783 dated Feb. 16, 2016.
International Search Report and Written Opinion for International Application No. PCT/US2014/050783 dated Nov. 18, 2014.
International Search Report for International Application No. PCT/US16/44916 dated Dec. 16, 2016.
International Search Report for International Application No. PCT/US2015/046401 dated Nov. 25, 2015.
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Available from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2013]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants with Relapsed or Refractory Mantle Cell Lymphoma. In: ClinicalTrials.gov [Internet]. Bethesda (MD): National Library of Medicine (US). Jun. 19, 2014—[cited Feb. 5, 2015] Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.
Janssen Research & Development, LLC. Pharmacokinetic and Pharmacodynamic Study to Evaluate Safety and Efficacy of the Combination of Ibrutinib with Nivolumab in Participants with Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.
Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.
Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013—[cited Nov. 22, 2013]. Available from: http://clinicaltrials.gov/ct2/show/NCT01969266 NLM Identifier: NCT01969266.
Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012—[cited Nov. 22, 2013]. Available from: http://clinicaltrials.gov/ct2/show/NCT01569750 NLM Identifier: NCT01569750.
Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.
Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCT01974440 NLM Identifier: NCT01974440.
Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.
Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013]. Available from: http://clinicaltrials.gov/ct2/show/NCT01776840 NLM Identifier: NCT01776840.
Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.
Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013—[cited Nov. 22, 2013]. Available from: http://clinicaltrials.gov/ct2/show/NCT01855750 NLM Identifier: NCT01855750.
Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National Library of Medicine (US). May 28, 2013—[cited Nov. 22, 2013]. Available from: http://clinicaltrials.gov/ct2/show/study/NCT01866033 NLM Identifier: NCT01866033.
Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012—[cited Nov. 22, 2013]. Available from: http://clinicaltrials.gov/ct2/show/NCT01626651 NLM Identifier: NCT01626651.
Janssen Research and Development, LLC. A study to assess the effect of rifampin on the pharmacokinetics of PCI-32765 in healthy participants. In: ClinicalTrials.gov [Internet]. Bethesda (MD):

(56) References Cited

OTHER PUBLICATIONS

National Library of Medicine (US). Jan. 4, 2013—[cited Nov. 22, 2013]. Available from: http://clinicaltrials.gov/ct2/show/NCT01763021 NLM Identifier: NCT01763021.

Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012—[cited Nov. 22, 2012]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012—[cited Nov. 22, 2013]. Available from: http://clinicaltrials.gov/ct2/show/NCT01646021 NLM Identifier: NCT01646021.

Kim et al. HRG-β1-driven ErbB3 signaling induces epithelial-mesenchymal transition in breast cancer cells. BMC Cancer. Aug. 12, 2013;13:383. doi: 10.1186/1471-2407-13-383.

Kushner et al. Pharmacological uses and perspective of heavy water and deuterated compounds. Canadian Journal of Physiology and Pharmacology 77(2):79-88 (1999).

Lopez et al. Combining PCI-24781, a Novel Histone Deacetylase Inhibitor, with Chemotherapy for the Treatment of Soft Tissue Sarcoma. Clin Cancer Res 15:1774-1775, 3472-3483 (2009).

M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.

M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.

M.D. Anderson Cancer Center. Ibrutinib Post Stem Cell Transplantation (SCR) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272686?term=NCT02272686 NLM Identifier: NCT02272686.

M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.

M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.

M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012—[cited Nov. 22, 2013]. Available from: http://clinicaltrials.govict2/show/NCT01520519 NLM Identifier: NCT01520519.

M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012—[cited Nov. 22, 2013]. Available from: http://clinicaltrials.gov/ct2/show/NCT01752426 NLM Identifier: NCT01752426.

Maddocks et al. Ibrutinib in B-cell lymphomas. Current Treatment Options in Oncology 15:226-237 (2014) (Epub: Feb. 1, 2014).

Memorial Sloan-Kettering Cancer Center. Bruton's Tyrosine Kinase (BTK) Inhibitor, Ibrutinib, in Patients with Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.

Montero et al. Neuregulins and cancer Clin Cancer Res. Jun. 1, 2008;14(11):3237-41. doi: 10.1158/1078-0432.CCR-07-5133.

National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov. 2, 2013—[cited Nov. 22, 2013]. Available from: http://clinicaltrials.gov/ct2/show/NCT01981512 NLM Identifier: NCT01981512.

National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr. 15, 2014]. Available from: http://clinicaltrials.gov/ct2/show/NCT02048813 NLM Identifier: NCT02048813.

National Cancer Institute (NCI). Ibrutinib in treating patients with relapsed hairy cell leukemia. In: ClinicalTrials.gov [Internet]. Bethesda (MD): National Library of Medicine (US). Apr. 24, 2013—[cited Nov. 22, 2013]. Available from: http://clinicaltrials.gov/ct2/show/NCT01841723 NLM Identifier: NCT01841723.

National Cancer Institute (NCI). Ibrutinib in treating patients with relapsed or refractory follicular lymphoma. In: ClinicalTrials.gov [Internet]. Bethesda (MD): National Library of Medicine (US). May 6, 2013—[cited Nov. 22, 2013]. Available from: http://clinicaltrials.gov/ct2/show/NCT01849263 NLM Identifier: NCT01849263.

National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01955499 NLM Identifier: NCT01955499.

National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.

National Cancer Institute (NCI). Rituximab, lenalidomide, and ibrutinib in treating patients with previously untreated stage II-IV

(56) References Cited

OTHER PUBLICATIONS follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829568.
National Cancer Institute. Ibrutinib and Combination Chemotherapy in Treating Patients with Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients with Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755.
National Cancer Institute. Ibrutinib in Treating Patients with Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients with HIV infection. In: ClinicalTrials.gov [Internet]. Bethesda (MD): National Library of Medicine (US). Apr. 7, 2014 [ cited Feb. 5, 2015]. Available from: https://clinicaltrials.gov/ct2/show/NCT02109224?term=NCT02109224. NLM Identifier: NCT02109224.
National Cancer Institute. Lenalidomide, Ibrutinib, and Rituximab in Treating Patients with Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886859 NLM Identifier: NCT01886859.
National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.
Nogrady (1985) Medicinal Chemistry A Biochemical Approach, Oxford University Press, New York, pp. 388-394.
Non-Final Office Action for U.S. Appl. No. 14/793,366, dated Nov. 1, 2016.
Non-Final Office Action for U.S. Appl. No. 15/054,952 dated Dec. 12, 2016, 25 pages.
Northwestern University. Ibrutinib After Intensive Induction in Treating Patients with Previously Untreated Mantle Cell Lymphoma. In: ClinicalTrials.gov [Internet]. Bethesda (MD): National Library of Medicine (US). Sep. 12, 2014 [cited Feb. 5, 2-15] Available from: https://clinicaltrial.gov/ct2/show/NCT02242097?term=NCT02242097 NLM Identifier: NCT02242097.
Notification of Office Action for Eurasian Application No. EA200901313 dated Oct. 31, 2011.
O'Brien et al. Combination of the Bruton's tyrosine kinase (BTK) inhibitor PCI-32765 with bendamustine (B)/rituximan® (BR) in patients (pts) with relapsed/refractory (R/R) chronic lymphocytic leukemia (CLL): Interm results of phase Ib/II study. J Clin Onc. 2012. Supp. Abstract 6515.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012—[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011—[cited Feb. 6, 2014]. Available from: http://clinicaltrials.gov/ct2/show/NCT01479842 NLM Identifier: NCT01479842.
Ou. Second-generation irreversible epidermal growth factor receptor (EGFR) tyrosine kinase inhibitors (TKIs): A better mousetrap? A review of the clinical evidence. Crit Rev Onc/Hemat. 2012;83(3):407-421.
Partial European Search Report for European Application No. EP 12172842.2 dated Jan. 24, 2013.
Pharmacyclics, Inc. A Multi-Center Study of Ibrutinib in Combination with Obinutuzumab Versus Chlorambucil in Combination with Obinutuzumab in Patients With Treatment naïve CLL or SLL. In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://clinicaltrials.gov/ct2/show/NCT01744691 NLM Identifier: NCT01744691.
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (RESONATE-2). In: ClinicalTrials.gov [Internet]. Bethesda (MD): National Library of Medicine (US). Oct. 29, 2012—[cited Nov. 22, 2013]. Available from: http://clinicaltrials.gov/ct2/show/NCT01722487 NLM Identifier: NCT01722487.
Pharmacyclics, Inc. A phase 3 study of ibrutinib (PCI-32765) versus ofatumumab in patients with relapsed or refractory chronic lymphocytic leukemia (RESONATE). In: ClinicalTrials.gov [Internet]. Bethesda (MD): National Library of Medicine (US). Apr. 11, 2012—[cited Nov. 22, 2013]. Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010—[cited Nov. 22, 2013]. Available from: http://clinicaltrials.gov/ct2/show/NCT01217749 NLM Identifier: NCT01217749.

(56) References Cited

OTHER PUBLICATIONS

Pharmacyclics, Inc. Ibrutinib and Lenalidomide with Dose Adjusted EPOCH-R in Subjects with Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.

Pharmacyclics, Inc. Ibrutinib in combination with lenalidomide, with and without rituximab in participants with relapsed or refractory diffuse large B-cell lymphoma. In: ClinicalTrials.gov [Internet]. Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.

Pharmacyclics, Inc. Ibrutinib with Rituximab in Previously Treated Adults with Waldenstrom's Macroglobulinemia. In: ClinicalTrials.gov [Internet]. Bethesda (MD): National Library of Medicine (US). Jun. 9, 2014 [cited Feb. 5, 2015] Available from: https://clinicaltrial.gov/ct2/show/NCT02165397?term=NCT02165397 NLM Identifier: NCT02165397.

Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://clinicaltrials.gov/ct2/show/NCT01236391 NLM Identifier: NCT01236391.

Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.

Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.

Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCT01109069 NLM Identifier: NCT01109069.

Pharmacyclics, Inc. Safety of PCI-32765 in chronic lymphocytic leukemia. In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.

Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.

Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier: NCT01980654.

Pharmacyclics, Inc. Study of the Bruton's Tyrosine Kinase Inhibitor in Subjects with Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.

Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier: NCT01478581.

Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013—[cited Nov. 22, 2013]. Available from: http://clinicaltrials.gov/ct2/show/NCT01980628 NLM Identifier: NCT01980628.

Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.

PRNewsire "U.S. FDA grants regular (full) approval for IMBRUVICA for two indications," Jul. 28, 2014.

Saulnier et al., "An efficient method for the synthesis of guanidine prodrugs," Bioorg. Medi. Chem. Lett., vol. 4, p. 1985-90 (1994).

Shah et al. Ibrutinib for the treatment of mantle cell lymphoma. Expert Rev. Hematol. 7(5):521-531 (2014) (Epub Aug. 27, 2014).

Silverman. The Organic Chemistry of Drug Design and Drug Action, Academic Press, Inc., San Diego, pp. 352-401 (1992).

Supplemental European Search Report for European Application No. EP 06850039 dated Feb. 15, 2010.

Supplementary European Search Report for European Application No. EP 14835935 dated Mar. 6, 2017.

TG Therapeutics, Inc. Ublituximab + ibrutinib in select B-cell malignancies. in: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.

The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 31, 2014—[cited Apr. 15, 2014]. Available from: http://clinicaltrails.gov/ct2/show/NCT02055924 NLM Identifier: NCT02055924.

Thurn et al. (Future Oncol. Feb. 2011; 7(2): 263-2830.

U.S. Appl. No. 14/091,196 Final Office Action dated Jan. 29, 2016.

U.S. Appl. No. 14/458,157 Non-Final Office Action dated Apr. 10, 2015.

U.S. Appl. No. 14/458,157 Non-Final Office Action dated Jul. 9, 2015.

University of California, San Diego. A Phase Ib/II Study of Ibrutinib in Combination with GA101-Obinutuzumab in Previously Untreated Chronic Lymphocytic Leukemia (CLL) Patients Over 65 Years of Age or with Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: https://clinicaltrial.gov/ct2/show/NCT02315768?term=NCT02315768 NLM Identifier: NCT02315768.

Wanner et al., "Mammalian Target of Rapamycin Inhibition Induces Cell Cycle Arrest in Diffuse Large B Cell Lymphoma (DLBCL) Cells and Sensitises DLBCL Cells to Rituximab," Brit J Haematol, 134: 475-484 (2006).

Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120:Abstract 686 (2012).

Written Opinion for European Application No. EP 10823966.6 dated Dec. 6, 2011.

\* cited by examiner

FIG. 1 A
| Cell line | Cmpd 1 GI50 (uM) |
|---|---|
| LY10 | 0.1 |
| WSU-NHL | 0.12 |
| DOHH2 | 0.12 |
| Mino | 0.15 |
| DHL6 | 0.18 |
| WSU-DLCL2 | 0.5 |
| DHL4 | 0.53 |
| DHL10 | 3.69 |
| Ramos | 5.5 |
| HF1 | >10 |
| LY19 | >10 |
| LY3 | >10 |
| DB | >10 |
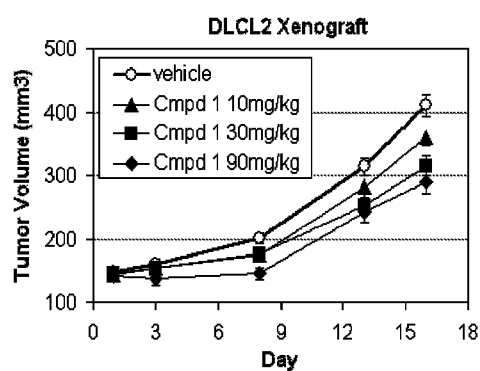
FIG. 1 B
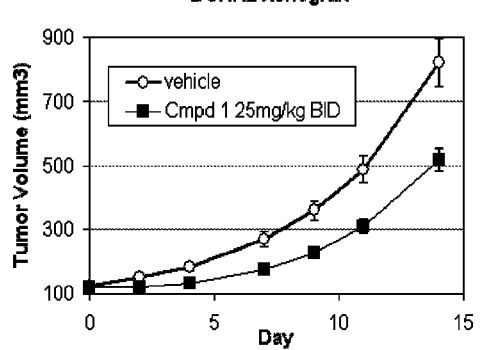
FIG. 1 C

FIG. 7

| #     | 473 | 474 | 475 | 476 | 477 | 478 | 479 | 480 | 481 | 482 | 483 |
|-------|-----|-----|-----|-----|-----|-----|-----|-----|---------|-----|-----|
| BTK   | I   | T   | E   | Y   | M   | A   | N   | G   | C       | L   | L   |
| BMX   | V   | T   | E   | Y   | M   | A   | R   | G   | C       | L   | L   |
| TEC   | V   | T   | E   | F   | M   | E   | R   | G   | C       | L   | L   |
| TXK   | V   | T   | E   | F   | M   | E   | N   | G   | C       | L   | L   |
| ITK   | V   | F   | E   | F   | M   | E   | H   | G   | C       | L   | S   |
| EGFR  | I   | T   | Q   | L   | M   | P   | F   | G   | C       | L   | L   |
| ErbB2 | V   | T   | Q   | L   | M   | P   | Y   | G   | C       | L   | L   |
| ErbB4 | V   | T   | Q   | L   | M   | P   | H   | G   | C       | L   | L   |
| JAK3  | V   | M   | E   | Y   | L   | P   | S   | G   | C       | L   | R   |
| BLK   | V   | T   | E   | Y   | L   | P   | S   | G   | C       | L   | L   |
| LCK   | I   | T   | E   | Y   | M   | E   | N   | G   | S       | L   | V   |
| LYN   | I   | T   | E   | Y   | M   | A   | K   | G   | S       | L   | L   |
| SYK   | V   | M   | E   | M   | A   | E   | L   | G   | P       | L   | N   |

MDA-MB-453,
xenograft in vivo 1h treatment

INHIBITORS OF BRUTON'S TYROSINE KINASE FOR THE TREATMENT OF SOLID TUMORS

RELATED APPLICATIONS

This application is a continuation of U.S. application Ser. No. 13/965,135, filed Aug. 12, 2013; which is a continuation-in-part of U.S. application Ser. No. 13/341,708, filed on Dec. 30, 2011, now U.S. Pat. No. 8,883,803, issued Nov. 11, 2014; and U.S. application Ser. No. 13/341,695, filed on Dec. 30, 2011, which are both continuations of U.S. application Ser. No. 13/003,811, filed on May 25, 2011; which is a U.S. National Stage Entry of PCT/US2009/050897, filed Jul. 16, 2009; which claims the benefit of U.S. Provisional Application No. 61/081,344, filed on Jul. 16, 2008; all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 23, 2015, is named 25922-782-303SEQ.txt and is 2,917 bytes in size.

BACKGROUND OF THE INVENTION

A kinase, alternatively known as a phosphotransferase, is a type of enzyme that transfers phosphate groups from high-energy donor molecules, such as ATP, to specific target molecules; the process is termed phosphorylation. Protein kinases, which act on and modify the activity of specific proteins, are used to transmit signals and control complex processes in cells. Up to 518 different kinases have been identified in humans. Their enormous diversity and role in signaling makes them attractive targets for drug design.

SUMMARY OF THE INVENTION

Disclosed herein, in certain embodiments, are methods for treating HER2 amplified breast cancer in an individual in need thereof comprising administering to an individual in need thereof a composition comprising a therapeutically-effective amount of a compound of Formula (C1) having the structure:

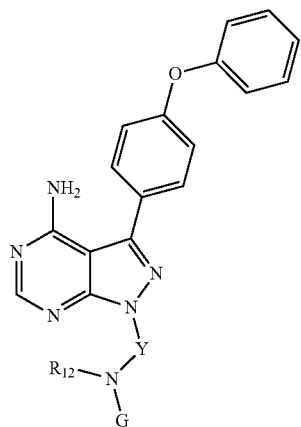

Formula (C1)

wherein:

Y is an optionally substituted group selected from among alkyl, heteroalkyl, aryl, heteroaryl, alkylaryl, alkylheteroaryl, and alkylheterocycloalkyl;

$R_{12}$ is H or lower alkyl; or

Y and $R_{12}$ taken together form a 4-, 5-, or 6-membered heterocyclic ring;

G is

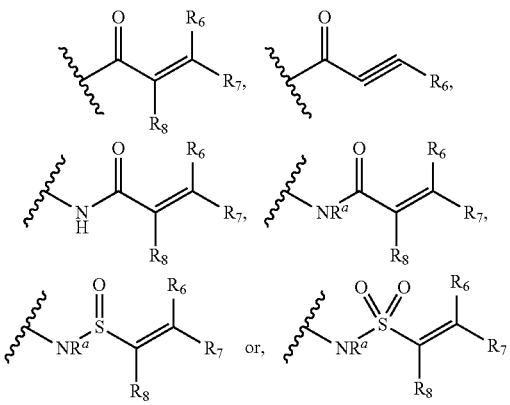

where $R^a$ is H, substituted or unsubstituted alkyl, substituted or unsubstituted cycloalkyl; and either $R_7$ and $R_8$ are H;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

$R_6$ and $R_8$ are H;

$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In some embodiments,
Y and R$_{12}$ taken together form a 4-, 5-, or 6-membered heterocyclic ring; and
Z is C(=O).

In some embodiments,
R$_6$ and R$_8$ are H; and
R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl).

In some embodiments,
Y and R$_{12}$ taken together form a 6-membered heterocyclic ring; and
R$_6$ and R$_8$ are H; and
R$_7$ is substituted or unsubstituted H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl).

In some embodiments, the compound of Formula (I) is (R)-1-(3-(4-amino-3-(4-phenoxyphenyl)-1H-pyrazolo[3,4-d]pyrimidin-1-yl)piperidin-1-yl)prop-2-en-1-one

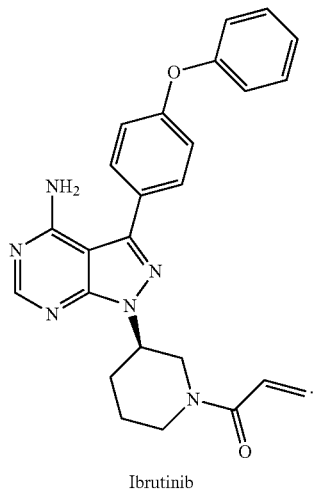

Ibrutinib

In some embodiments, the method further comprises administering an additional therapeutic agent selected from: trastuzumab, paclitaxel, doxorubicin, cyclophosphamide, and cisplatin. In some embodiments, the method further comprises administering trastuzumab.

Disclosed herein, in certain embodiment, are methods for treating HER2 amplified cancer in an individual in need thereof comprising administering to an individual in need thereof a composition comprising a therapeutically-effective amount of a compound of Formula (C1) having the structure:

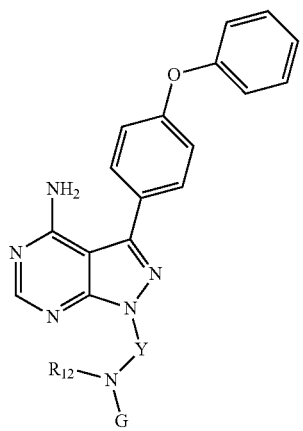

Formula (C1)

wherein:
Y is an optionally substituted group selected from among alkyl, heteroalkyl, aryl, heteroaryl, alkylaryl, alkylheteroaryl, and alkylheterocycloalkyl;
R$_{12}$ is H or lower alkyl; or
Y and R$_{12}$ taken together form a 4-, 5-, or 6-membered heterocyclic ring;
G is

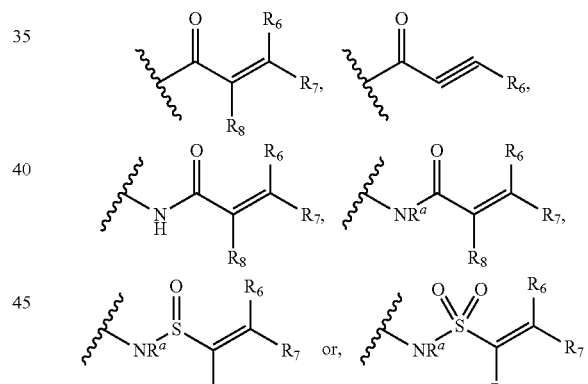

where R$^a$ is H, substituted or unsubstituted alkyl, substituted or unsubstituted cycloalkyl; and either
R$_7$ and R$_8$ are H;
R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);
R$_6$ and R$_8$ are H;
R$_7$ is H, substituted or unsubstituted C$_1$-C$_4$alkyl, substituted or unsubstituted C$_1$-C$_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In some embodiments,

Y and $R_{12}$ taken together form a 4-, 5-, or 6-membered heterocyclic ring; and Z is C(=O).

In some embodiments, $R_6$ and $R_8$ are H; and $R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In some embodiments,

Y and $R_{12}$ taken together form a 6-membered heterocyclic ring;

$R_6$ and $R_8$ are H; and $R_7$ is substituted or unsubstituted H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In some embodiments, the compound of Formula (I) is (R)-1-(3-(4-amino-3-(4-phenoxyphenyl)-1H-pyrazolo[3,4-d]pyrimidin-1-yl)piperidin-1-yl)prop-2-en-1-one

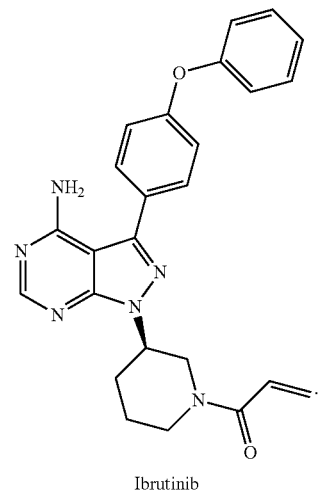 [SMILES: C=CC(=O)N1CCC[C@@H](n2nc(-c3ccc(Oc4ccccc4)cc3)c3c(N)ncnc32)C1]

Ibrutinib

In some embodiments, the method further comprises administering an additional therapeutic agent selected from: trastuzumab, paclitaxel, doxorubicin, cyclophosphamide, and cisplatin. In some embodiments, the method further comprises administering trastuzumab.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —$CH_2$— group; and an ethylene is a diradical of an ethyl group, i.e., —$CH_2CH_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ . . . $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=$CH_2$, —C($CH_3$)=$CH_2$, —CH=$CHCH_3$, —C($CH_3$)=$CHCH_3$. Alkenylene groups include, but are not limited to, —CH=CH—, —C($CH_3$)=CH—, —CH=$CHCH_2$—, —CH=$CHCH_2CH_2$— and —C($CH_3$)=$CHCH_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡$CCH_3$, —C≡$CCH_2CH_3$, —C≡C—, and —C≡$CCH_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkylhydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)2-, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

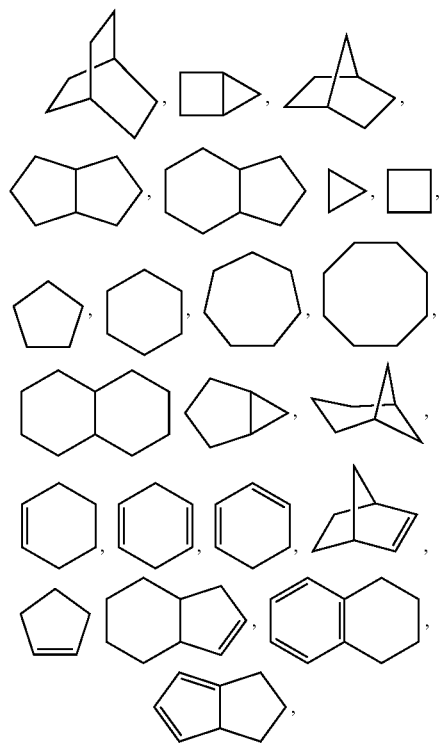

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

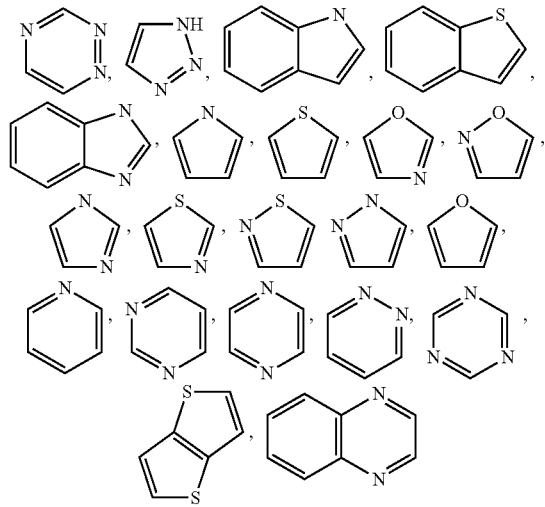

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

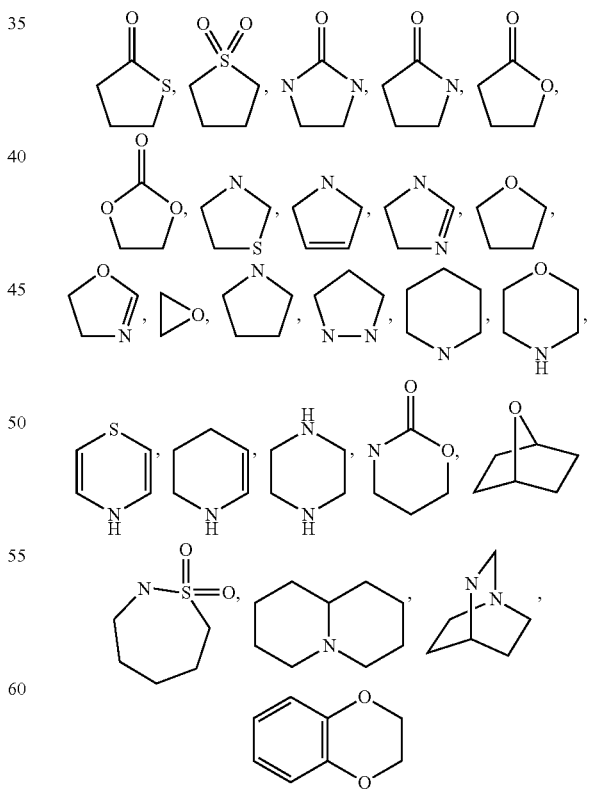

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —CF$_3$, —CH$_2$CF$_3$, —CF$_2$CF$_3$, —CH$_2$CH$_2$CF$_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In addition, in some embodiments, up to two heteroatoms are consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be L$_s$R$_s$, wherein each L$_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R$_s$ is independently selected from H, (substituted or unsubstituted C$_1$-C$_4$alkyl), (substituted or unsubstituted C$_3$-C$_6$cycloalkyl), heteroaryl, or heteroalkyl. The protecting groups that forms the protective derivatives of the above substituents include those found in sources such as Greene and Wuts, above.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The "G" groups presented in any of Formula (A1-A6), Formula (B1-B6), Formula (C1-C6), Formula (D1-D6), Formula (I), or Formula (VII) are non-limiting examples of Michael acceptor moieties.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Michael acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, "ACK" and "Accessible Cysteine Kinase" are synonyms. They mean a kinase with an accessible cysteine residue. ACKS include, but are not limited to, BTK, ITK, Bmx/ETK, TEC, EFGR, HER4, HER4, LCK, BLK, C-src, FGR, Fyn, HCK, Lyn, YES, ABL, Brk, CSK, FER, JAK3, SYK. In some embodiments, the ACK is HER4.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (A1-A6), Formula (B1-B6), Formula (C1-C6), Formula (D1-D6), Formula (I), or Formula (VII), dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of any of Formula (A1-A6), Formula (B1-B6), Formula (C1-C6), Formula (D1-D6), Formula (I), or Formula (VII), are absorbed into the general circulation when the pharmaceutical composition is taken orally as compared to intravenous injection.

The term "biophysical probe," as used herein, refers to probes which detect or monitor structural changes in molecules (including biomolecules) in biological systems or in the presence of other biomolecules (e.g., ex vivo, in vivo or in vitro). In some embodiments, such molecules include, but are not limited to, proteins and the "biophysical probe" is used to detect or monitor interaction of proteins with other macromolecules. In other embodiments, examples of biophysical probes include, but are not limited to, spin-labels, fluorophores, and photoactivatable groups.

"Blood plasma concentration" refers to the concentration of compounds disclosed herein, such as, compounds of any of Formula (A1-A6), Formula (B1-B6), Formula (C1-C6), Formula (D1-D6), Formula (I), or Formula (VII), in the plasma component of blood of an individual. It is understood that the plasma concentration of compounds of any of Formula (A1-A6), Formula (B1-B6), Formula (C1-C6), Formula (D1-D6), Formula (I), or Formula (VII), may vary significantly between subjects, due to variability with respect to metabolism and/or possible interactions with other therapeutic agents. In accordance with one embodiment disclosed herein, the blood plasma concentration of the compounds of any of Formula (A1-A6), Formula (B1-B6), Formula (C1-C6), Formula (D1-D6), Formula (I), or Formula (VII), does vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any of Formula (A1-A6), Formula (B1-B6), Formula (C1-C6), Formula (D1-D6), Formula (I), or Formula (VII), is expected to vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ" (SEQ ID NO: 1)).

The term "HER4", also known as ERBB4, also known as "V-erb-a erythroblastic leukemia viral oncogene homolog 4" means either (a) the nucleic acid sequence encoding a receptor tyrosine kinase that is a member of the epidermal growth factor receptor subfamily, or (b) the protein thereof. For the nucleic acid sequence that comprises the human HER4 gene see GenBank Accession No. NM_001042599. For the amino acid sequence that comprises the human HER4 protein see GenBank Accession No. NP_001036064.

The term "chemiluminescent group," as used herein, refers to a group which emits light as a result of a chemical reaction without the addition of heat. By way of example only, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The terms "co-administration" or the like, as used herein, are meant to encompass administration of the selected therapeutic agents to a single patient, and are intended to include treatment regimens in which the agents are administered by the same or different route of administration or at the same or different time.

In other embodiments, the term "detectable label," as used herein, refers to a label which is observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The term "dye," as used herein, refers to a soluble, coloring substance which contains a chromophore.

The terms "effective amount" or "therapeutically effective amount," as used herein, refer to a sufficient amount of an agent or a compound being administered which will relieve to some extent one or more of the symptoms of the disorder being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case is optionally determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (A1-A6), Formula (B1-B6), Formula (C1-C6), Formula (D1-D6), Formula (I), or Formula (VII), age, weight, general condition of the subject, the condition being treated, the severity of the condition being treated, and the judgment of the prescribing physician.

The term "electron dense group," as used herein, refers to a group which scatters electrons when irradiated with an electron beam. Such groups include, but are not limited to, ammonium molybdate, bismuth subnitrate cadmium iodide, 99%, carbohydrazide, ferric chloride hexahydrate, hexamethylene tetramine, 98.5%, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

In other embodiments, the term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disorder. An "enhancing-effective amount," as used herein, refers to an amount adequate to enhance the effect of a therapeutic agent in the treatment of a disorder. When used in an individual, amounts effective for this use will depend on the severity and course of the disorder, previous therapy, the individual's health status and response to the drugs, and the judgment of the treating physician.

The term "fluorophore," as used herein, refers to a molecule which upon excitation emits photons and is thereby fluorescent.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. Other examples of kinases having homologous cysteines are shown in FIG. 7. See also the sequence alignments of tyrosine kinases (TK) published on the world wide web at kinase.com/human/kinome/phylogeny.html.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences are "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in FIG. 7.

The term "isolated," as used herein, refers to separating and removing a component of interest from at least some portion of components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

In some embodiments, the term "label," as used herein, refers to a substance which is incorporated into a compound and is readily detected, whereby its physical distribution is detected and/or monitored.

The term "linkage," as used herein to refer to bonds or a chemical moiety formed from a chemical reaction between the functional group of a linker and another molecule. In some embodiments, such bonds include, but are not limited to, covalent linkages and non-covalent bonds, while such chemical moieties include, but are not limited to, esters, carbonates, imines, phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. In other embodiments, enzymatically unstable or degradable linkages means that the linkage is degraded by one or more enzymes. By way of example only, PEG and related polymers include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The phrase "measuring the activity of the reporter moiety" (or a similarly worded phrase) refers to methods for quantifying (in absolute, approximate or relative terms) the reporter moiety in a system under study. In some embodiments, such methods include any methods that quantify a reporter moiety that is a dye; a photocrosslinker; a cytotoxic compound; a drug; an affinity label; a photoaffinity label; a reactive compound; an antibody or antibody fragment; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; a redox-active agent; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; and any combination of the above.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism is obtained from The Pharmacological Basis of Therapeutics, 9th Edition, McGraw-Hill (1996). Metabolites of the compounds disclosed herein are optionally identified either by administration of compounds to a host and analysis of tissue samples from the host, or by incubation of compounds with hepatic cells in vitro and analysis of the resulting compounds. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "nanoparticle," as used herein, refers to a particle which has a particle size between about 500 nm to about 1 nm.

As used herein, the term "pERK" refers to phosphorylated ERK1 and ERK2 at Thr202/Tyr 204 as detected by commercially available phospho-specific antibodies (e.g. Cell Signaling Technologies #4377).

The term "photoaffinity label," as used herein, refers to a label with a group, which, upon exposure to light, forms a linkage with a molecule for which the label has an affinity. By way of example only, in some embodiments, such a linkage is covalent or non-covalent.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "plasma half life," as used herein refers to half-life in rat, dog or human as determined by measure drug concentration over time in plasma following a single dose and fitting data to standard pharmacokinetic models using software such as WinNonLin to determine the time at which drug has been 50% eliminated from plasma.

The term "prophylactically effective amount," as used herein, refers that amount of a composition applied to an individual which will relieve to some extent one or more of the symptoms of a disease, disorder being treated. In such prophylactic applications, such amounts may depend on the patient's state of health, weight, and the like.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "individual" as used herein, refers to a mammal which is the object of treatment, observation or experiment. The term is not to be construed as requiring the supervision of a medical practicioner (e.g., a physician, physician's assistant, nurse, orderly, hospice care worker).

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disorder.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a symptom of a disorder, preventing additional symptoms, ameliorating or preventing the underlying metabolic causes of symptoms, inhibiting the disorder, e.g., arresting the development of the disorder, relieving the disorder, causing regression of the disorder, relieving a condition caused by the disorder, or stopping the symptoms of the disorder. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

BRIEF DESCRIPTION OF THE FIGURES

FIG. 1A presents an illustrative table of $GI_{50}$ concentrations of Compound 1 that results in 50% decrease in cell proliferation. A variety of lymphoma cell lines incubated with a range of concentrations of Compound 1. FIG. 1B presents an illustrative line graph showing inhibition of tumor growth in DLCL2 xenograft models. FIG. 1C presents an illustrative line graph showing inhibition of tumor growth in DOHH2 xenograft models. For in vivo lymphoma xenograft studies, 5E6 DOHH2 or DLCL2 cells in 50% matrigel were implanted subcutaneously in SCID mice and dosed orally with Compound 1 beginning when tumor size reached 100 mm2.

FIG. 7 presents illustrative ACKs, including Btk and Btk cysteine homologs. FIG. 7 discloses SEQ ID NOS: 2-14, respectively, in order of appearance.

(FIG. 9B) SK-BR3 cells—ibrutinib, AVL-292 and PCI-4546; (FIG. 9C) UACC-893 cells—ibrutinib; and (FIG. 9D) MDA-MB-453 cells—ibrutinib, AVL-292 and PCI-4546.

(FIG. 10B) 3-day treatment: PI.

DETAILED DESCRIPTION OF THE INVENTION

Solid Tumors

Figure 2:
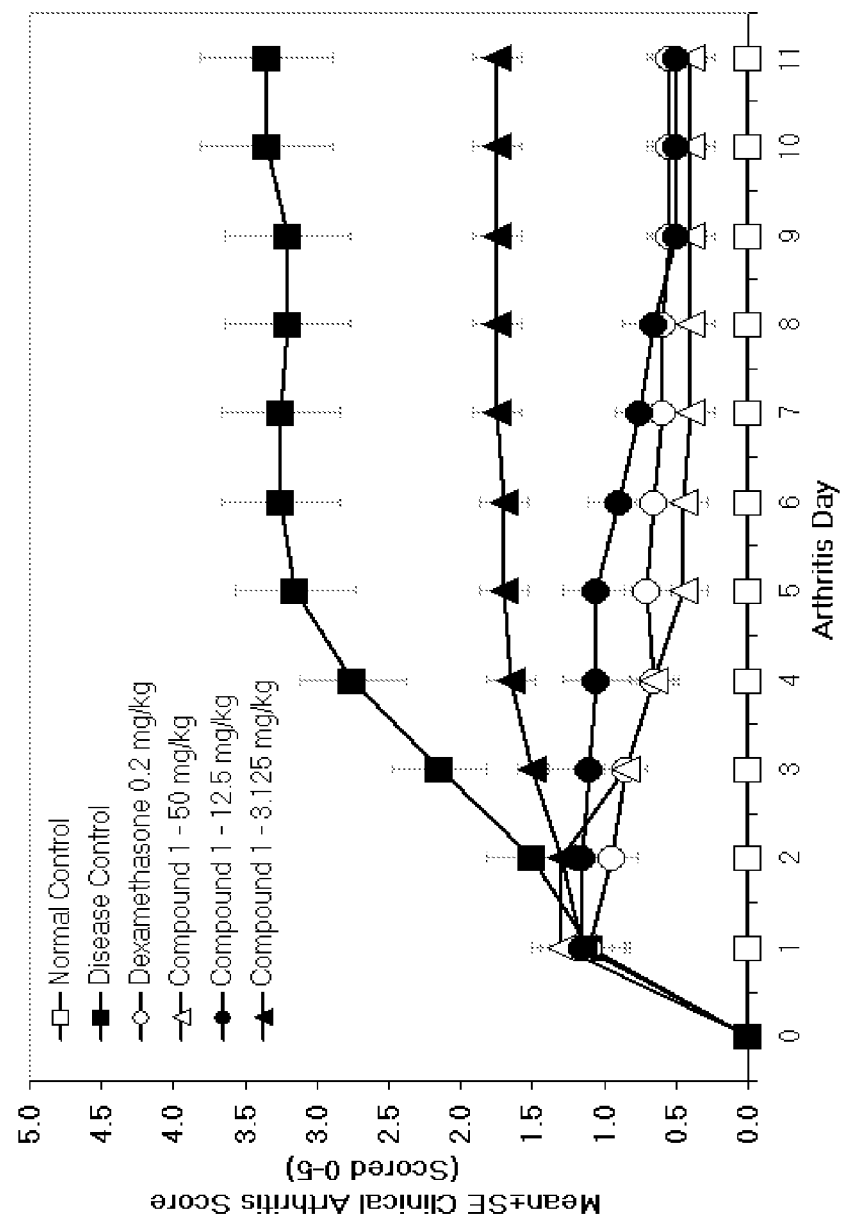
FIG. 2 presents an illustrative line graph showing inhibition of collagen-induced arthritis in male DBA/1OlaHsd mice. Compound 1 or vehicle was dosed orally once per day starting at day 1. Dexamethasone was included as a positive control. Paw inflammation was scored from 0-5 and averaged across all paws from all animals for each group in the study. Compound 1 at 12.5 mg/kg and 50 mg/kg regressed inflammation through the end of the study (day 11) while 3.125 mg/kg significantly reduced the increase in paw inflammation.

In some embodiments, the compounds and formulations described herein are utilized to treat one or more disorders characterized by the presence or development of a solid tumor. As used herein, "solid tumors" are neoplasms characterized by an absence of liquid areas. In some embodiments, the solid tumor is benign. In some embodiments, the solid tumor is malignant. In some embodiments, the cancer is characterized by the presence of one or more solid tumor is a sarcoma, carcinoma, and/or lymphoma.

In some embodiments, the disorder characterized by the presence or development of one or more solid tumors is a sarcoma. Sarcomas are cancers of the bone, cartilage, fat, muscle, blood vessels, or other connective or supportive tissue. Sarcomas include, but are not limited to, chondrosarcoma, Ewing's sarcoma, malignant hemangioendothelioma, malignant schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

In some embodiments, the disorder characterized by the presence or development of one or more solid tumors is a lymphoma. Lymphomas are solid neoplasms that originate in lymphocytes. Hodgkin lymphoma is marked by the presence of the Reed-Sternberg cell. Non-Hodgkin lymphomas are all lymphomas which are not Hodgkin's lymphoma. Non-Hodgkin lymphomas are further divided into indolent lymphomas and aggressive lymphomas. Non-Hodgkin's lymphomas include, but are not limited to, diffuse large B cell lymphoma; follicular lymphoma, Mucosa-Associated Lymphatic Tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and Lymphomatoid granulomatosis.

In some embodiments, the disorder characterized by the presence or development of one or more solid tumors is a carcinoma. Carcinomas are cancers that begin in the epithelial cells. By way of non-limiting example, carcinomas include most breast cancers (e.g. mammary ductal carcinoma and lobular carcinoma), most pancreatic cancers, most lung cancers (e.g. small cell lung carcinoma, and non-small cell lung carcinoma), most colon cancers, most kidney cancers, and melanomas. In some embodiments, the disease is mammary ductal carcinoma, lobular carcinoma, an adenocarcinoma (e.g. pancreatic cancer and colon cancer), small cell lung carcinoma, non-small cell lung carcinoma, and melanomas. In some embodiments, the disease is breast cancer. In some embodiments, the disease is mammary ductal carcinoma, lobular carcinoma, or a combination thereof. In some embodiments, the breast cancer is ER positive. In some embodiments, the breast cancer is ER negative. In some embodiments, the breast cancer is progesterone receptor (PgR)-positive. In some embodiments, the breast cancer is PgR-negative. In some embodiments, the disease is pancreatic cancer.

Pancreatic cancer is defined as the presence of malignant tumors of the pancreas. The prognosis for individuals with pancreatic cancer is generally regarded as poor. In general only about 10 to 15% of patients diagnosed with the disorder will survive for 1 year or more; only about 3% live for 5 years or more; and only about 2% live for 10 years or more. The majority of pancreatic tumors are classified as adenocarcinomas.

Mammary ductal carcinoma is a type of breast cancer. It comes in two forms. Infiltrating ductal carcinoma (IDC) is an invasive, malignant and abnormal proliferation of neoplastic cells in the breast tissue. Ductal carcinoma in situ (DCIS), is a noninvasive, possibly malignant neoplasm that is still confined to the lactiferous ducts, where breast cancer most often originates.

Lobular carcinoma is a neoplasm primarily found in the lobules of a gland. It comes in two forms. Lobular carcinoma in situ (LCIS) is a condition caused by neoplastic (but not necessarily cancerous) cells in the lobules of a breast. Invasive lobular carcinoma (aka infiltrating lobular carcinoma) is a type of breast cancer that begins in the lobules and then invades surrounding tissues.

The growth and development (e.g. into malignant tumors) of a solid tumor requires the growth of new blood vessels (i.e. angiogenesis). The transcription factor MYC is often overexpressed in cancerous cells. In certain instances, MYC facilitates angiogenesis in tumors by recruiting mast cells to the tumor. In certain instances, tumor cells will undergo hypoxia and cell death if mast cell recruitment is inhibited. In some embodiments, mast cell recruitment is inhibited by the use of a Btk inhibitor. In some embodiments, mast cells are killed (e.g. by necrosis or apoptosis) by the use of a Btk inhibitor.

In some embodiments, the disease is HER2 amplified breast cancer. HER2 (Human Epidermal Growth Factor Receptor 2) also known as Neu, ErbB2, CD340 (cluster of differentiation 340) and p185 is an epidermal growth factor receptor found on cells. The HER2 gene is found on human chromosome 17. HER2 protein is composed of four plasma membrane-bound receptor tyrosine kinases. Signaling pathways activated by HER2 protein include: mitogen-activated protein kinase (MAPK), phosphoinositide 3-kinase (PI3K/Akt), phospholipase C γ, protein kinase C (PKC), and signal transducer and activator of transcription (STAT). As used herein, "HER2-amplified cancer" means a cancer (e.g., breast cancer) characterized by amplification (or, over-expression) of the HER2 gene. Amplification of HER2 gene expression leads to increased membrane expression of the HER2 protein. Increased expression is associated with increased dimerization of HER2 proteins with HER3 and HER4. Increased dimerization leads to increased activation of the HER2 tyrosine kinase resulting in excessive mitosis and cell replication.

Irreversible Inhibitor Compounds

In the following description of irreversible kinase inhibitor compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. In addition, nucleic acid and amino acid sequences for Btk (e.g., human Btk) are disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients The inhibitor compounds described herein are selective for kinases having an accessible cysteine residue (such kinases are also known as Accessible Cysteine Kinases, or ACKs) that is able to form a covalent bond with a Michael acceptor moiety on the inhibitor compound. In some embodiments, the cysteine residue is accessible or becomes accessible when the binding site moiety of the irreversible inhibitor binds to the kinase. That is, the binding site moiety of the irreversible inhibitor binds to an active site of the ACK and the Michael acceptor moiety of irreversible inhibitor gains access (in one embodiment the step of binding leads to a conformational change in the ACK, thus exposing the cysteine) or is otherwise exposed to the cysteine residue of the ACK; as a result a covalent bond is formed between the "S" of the cysteine residue and the Michael acceptor of the irreversible inhibitor. Consequently, the binding site moiety of the irreversible inhibitor remains bound or otherwise blocks the active site of the ACK.

In one embodiment, the ACK is Btk, a homolog of Btk or a tyrosine kinase having a cysteine residue in an amino acid sequence position that is homologous to the amino acid sequence position of cysteine 481 in Btk. See, e.g., kinases in FIG. 7. In some embodiments, the ACK is HER4. Inhibitor compounds described herein include a Michael acceptor moiety, a binding site moiety and a linker that links the binding site moiety and the Michael acceptor moiety (and in some embodiments, the structure of the linker provides a conformation, or otherwise directs the Michael acceptor moiety, so as to improve the selectivity of the irreversible inhibitor for a particular ACK).

Generally, an irreversible inhibitor compound used in the methods described herein is identified or characterized in an in vitro assay, e.g., an a cellular biochemical assay or a cellular functional assay. Such assays are useful to determine an in vitro $IC_{50}$ for an irreversible inhibitor compound.

For example, a cellular kinase assay is used to determine kinase activity after incubation of the kinase in the absence or presence of a range of concentrations of a candidate irreversible inhibitor compound. If the candidate compound is in fact an irreversible inhibitor, kinase activity will not be recovered by repeat washing with inhibitor-free medium. See, e.g., J. B. Smaill, et al. (1999), *J. Med. Chem.* 42(10): 1803-1815. Further, covalent complex formation between a Kinase and a candidate irreversible inhibitor is a useful indicator of irreversible inhibition of the Kinase that is readily determined by a number of methods (e.g., mass spectrometry). For example, some irreversible Kinase-inhibitor compounds form a covalent bond with the aforenoted cysteine residue (e.g., via a Michael reaction).

High throughput assays for many a cellular biochemical assays (e.g., kinase assays) and cellular functional assays (e.g., calcium flux) are documented methodologies. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of irreversible compounds.

In some embodiments, irreversible inhibitor compounds are used for the manufacture of a medicament for treating any of the foregoing conditions (e.g. lymphomas, carcinomas, and/or sarcomas).

In some embodiments, the irreversible inhibitor compound used for the methods described herein inhibits a Kinase activity with an in vitro $IC_{50}$ of less than 10 µM. (e.g., less than 1 µM, less than 0.5 µM, less than 0.4 µM, less than 0.3 µM, less than 0.1, less than 0.08 µM, less than 0.06 µM, less than 0.05 µM, less than 0.04 µM, less than 0.03 µM, less than less than 0.02 µM, less than 0.01, less than 0.008 µM, less than 0.006 µM, less than 0.005 µM, less than 0.004 µM, less than 0.003 µM, less than less than 0.002 µM, less than 0.001, less than 0.00099 µM, less than 0.00098 µM, less than 0.00097 µM, less than 0.00096 µM, less than 0.00095 µM, less than 0.00094 µM, less than 0.00093 µM, less than 0.00092, or less than 0.00090 µM).

In one embodiment, the irreversible inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Particular Irreversible Inhibitor Compounds for ACKs

Described herein are compounds of any of Formula (A1-A6), Formula (B1-B6), Formula (C1-C6), Formula (D1-D6), Formula (I), or Formula (VII). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom is optionally converted to an N-oxide. In certain embodiments, isomers and chemically protected forms of compounds having a structure represented by any of Formula (A1-A6), Formula (B1-B6), Formula (C1-C6), Formula (D1-D6), Formula (I), or Formula (VII), are also provided.

In one aspect are compounds (including irreversible inhibitors of ACKs, including Btk and its cysteine homologs) having the structure of Formula (I):

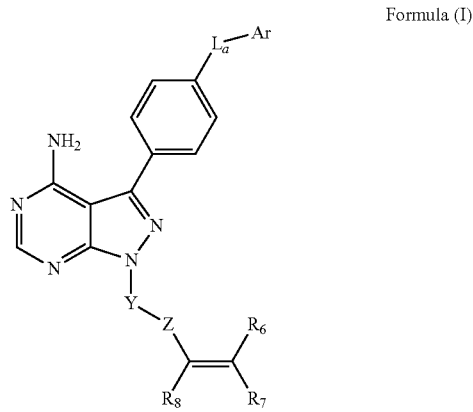

Formula (I)

wherein $L_a$ is $CH_2$, O, NH or S;

Ar is a substituted or unsubstituted aryl, or a substituted or unsubstituted heteroaryl; and either (a) Y is an optionally substituted group selected from among alkylene, heteroalkylene, arylene, heteroarylene, alkylenearylene, alkyleneheteroarylene, alkylenecycloalkylene and alkyleneheterocycloalkylene;

Z is C(=O), NHC(=O), $NR^aC(=O)$, $NR^aS(=O)_x$, where x is 1 or 2, and $R^a$ is H, substituted or unsubstituted alkyl, substituted or unsubstituted cycloalkyl; and either (i) $R_7$ and $R_8$ are H;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

(ii) $R_6$ and $R_8$ are H;

$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or (iii) $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or (b) Y is an optionally substituted group selected from cycloalkylene or heterocycloalkylene;

Z is C(=O), NHC(=O), $NR^aC(=O)$, $NR^aS(=O)_x$, where x is 1 or 2, and $R^a$ is H, substituted or unsubstituted alkyl, substituted or unsubstituted cycloalkyl; and either (i) $R_7$ and $R_8$ are H;

$R_6$ is substituted or unsubstituted $C_1$-$C_4$heteroalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

(ii) $R_6$ and $R_8$ are H;

$R_7$ is substituted or unsubstituted $C_1$-$C_4$heteroalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or (iii) $R_7$ and $R_8$ taken together form a bond;

$R_6$ is substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); and pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (I). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (I), including those in which the ester group is selected from a formate, acetate, propionate, butyrate, acrylate and ethylsuccinate.

In another embodiment are pharmaceutically acceptable carbamates of compounds of Formula (I). In another embodiment are pharmaceutically acceptable N-acyl derivatives of compounds of Formula (I). Examples of N-acyl groups include N-acetyl and N-ethoxycarbonyl groups.

For any and all of the embodiments, substituents can be selected from among from a subset of the listed alternatives. For example, in some embodiments, $L_a$ is $CH_2$, O, or NH. In other embodiments, $L_a$ is O or NH. In yet other embodiments, $L_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is C(=O), OC(=O), NHC(=O), S(=O)$_x$, OS(=O)$_x$, or NHS(=O)$_x$. In some other embodiments, Z is C(=O), NHC(=O), or NCH$_3$C(=O).

In some embodiments Y is an optionally substituted group selected from among alkylene, heteroalkylene, arylene, heteroarylene, alkylenearylene, alkyleneheteroarylene, and alkyleneheterocycloalkylene.

In some embodiments, Z is C(=O), NHC(=O), NR$^a$C(=O), NR$^a$S(=O)$_x$, where x is 1 or 2, and R$^a$ is H, substituted or unsubstituted alkyl, substituted or unsubstituted cycloalkyl.

In some embodiments, $R_7$ and $R_8$ are H; and $R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl). In other embodiments, $R_6$ and $R_8$ are H; and $R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl). In yet further embodiments, $R_7$ and $R_8$ taken together form a bond; and $R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In some embodiments, Y is an optionally substituted group selected from cycloalkylene or heterocycloalkylene.

In some embodiments, Z is C(=O), NHC(=O), NR$^a$C(=O), NR$^a$S(=O)$_x$, where x is 1 or 2, and R$^a$ is H, substituted or unsubstituted alkyl, substituted or unsubstituted cycloalkyl.

In some embodiments, $R_7$ and $R_8$ are H; and $R_6$ is substituted or unsubstituted $C_1$-$C_4$heteroalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl). In other embodiments, $R_6$ and $R_8$ are H; and $R_7$ is substituted or unsubstituted $C_1$-$C_4$heteroalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl). In further embodiments, $R_7$ and $R_8$ taken together form a bond; and $R_6$ is substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkylC$_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl).

In one aspect are compounds (including irreversible inhibitors of ACKs, including Btk and its cysteine homologs) having the structure of Formula (VII):

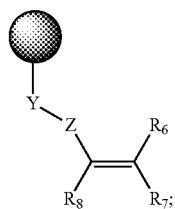

wherein

is a moiety that binds to the active site of a kinase, including a tyrosine kinase, further including a Btk kinase cysteine homolog;

Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene;

Z is C(=O), OC(=O), NHC(=O), NCH$_3$C(=O), C(=S), S(=O)$_x$, OS(=O)$_x$, NHS(=O)$_x$, where x is 1 or 2;

$R_7$ and $R_8$ are independently selected from among H, unsubstituted $C_1$-$C_4$ alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond; and $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl); and pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (VII). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (VII), including those in which the ester group is selected from a formate, acetate, propionate, butyrate, acrylate and ethylsuccinate.

In another embodiment are pharmaceutically acceptable carbamates of compounds of Formula (VII). In another embodiment are pharmaceutically acceptable N-acyl derivatives of compounds of Formula (VII). Examples of N-acyl groups include N-acetyl and N-ethoxycarbonyl groups.

In some embodiments, x is 2. In yet other embodiments, Z is C(=O), OC(=O), NHC(=O), S(=O)$_x$, OS(=O)$_x$, or NHS(=O)$_x$. In some other embodiments, Z is C(=O), NHC(=O), or S(=O)$_2$.

In some embodiments, $R_7$ and $R_8$ are independently selected from among H, unsubstituted $C_1$-$C_4$ alkyl, substituted $C_1$-$C_4$alkyl, unsubstituted $C_1$-$C_4$heteroalkyl, and substituted $C_1$-$C_4$heteroalkyl; or $R_7$ and $R_8$ taken together form a bond. In yet other embodiments, each of $R_7$ and $R_8$ is H; or $R_7$ and $R_8$ taken together form a bond.

In some embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted aryl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In some other embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, $C_1$-$C_4$alkyl (aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In yet other embodiments, $R_6$ is H, substituted or unsubstituted $C_1$-$C_4$alkyl, —CH$_2$—O—($C_1$-$C_3$alkyl), —CH$_2$—N($C_1$-$C_3$alkyl)$_2$, $C_1$-$C_4$alkyl(phenyl), or $C_1$-$C_4$alkyl(5- or 6-membered heteroaryl). In yet other embodiments, $R_6$ is H, substituted or unsubstituted $C_1$-$C_4$alkyl, —CH$_2$—O—($C_1$-$C_3$alkyl), —CH$_2$—($C_1$-$C_6$alkylamino), $C_1$-$C_4$alkyl(phenyl), or $C_1$-$C_4$alkyl(5- or 6-membered heteroaryl). In some embodiments, $R_6$ is H, substituted or unsubstituted $C_1$-$C_4$alkyl, —CH$_2$—O—($C_1$-$C_3$alkyl), —CH$_2$—N($C_1$-$C_3$alkyl)$_2$, $C_1$-$C_4$alkyl(phenyl), or $C_1$-$C_4$alkyl(5- or 6-membered heteroaryl containing 1 or 2 N atoms), or $C_1$-$C_4$alkyl (5- or 6-membered heterocycloalkyl containing 1 or 2 N atoms).

In some embodiments, Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene. In other embodiments, Y is an optionally substituted group selected from among $C_1$-$C_6$alkylene, $C_1$-$C_6$heteroalkylene, 4-, 5-, 6-, or 7-membered cycloalkylene, and 4-, 5-, 6-, or 7-membered heterocycloalkylene. In yet other embodiments, Y is an optionally substituted group selected from among $C_1$-$C_6$alkylene, $C_1$-$C_6$heteroalkylene, 5- or 6-membered cycloalkylene, and 5- or 6-membered heterocycloalkylene containing 1 or 2 N atoms. In some other embodiments, Y is a 5- or 6-membered cycloalkylene, or a 5- or 6-membered heterocycloalkylene containing 1 or 2 N atoms. In some embodiments, Y is a 4-, 5-, 6-, or 7-membered cycloalkylene ring; or Y is a 4-, 5-, 6-, or 7-membered heterocycloalkylene ring.

In one aspect are compounds (including irreversible inhibitors of ACKs, including Btk and its cysteine homologs) having the structure of Formula (A1):

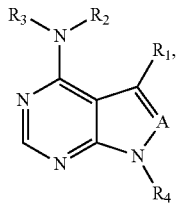

Formula (A1)

wherein
A is independently selected from N or CR$_5$;
R$_1$ is H, L$_2$-(substituted or unsubstituted alkyl), L$_2$-(substituted or unsubstituted cycloalkyl), L$_2$-(substituted or unsubstituted alkenyl), L$_2$-(substituted or unsubstituted cycloalkenyl), L$_2$-(substituted or unsubstituted heterocycle), L$_2$-(substituted or unsubstituted heteroaryl), or L$_2$-(substituted or unsubstituted aryl), where L$_2$ is a bond, O, S, —S(=O), —S(=O)$_2$, C(=O), -(substituted or unsubstituted C$_1$-C$_6$ alkyl), or -(substituted or unsubstituted C$_2$-C$_6$ alkenyl);
R$_2$ and R$_3$ are independently selected from H, lower alkyl and substituted lower alkyl;
R$_4$ is L$_3$-X-L$_4$-G, wherein,
L$_3$ is optional, and when present is a bond, or an optionally substituted group selected from alkyl, heteroalkyl, aryl, heteroaryl, alkylaryl, alkylheteroaryl, or alkylheterocycloalkyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or L$_3$, X and L$_4$ taken together form a nitrogen containing heterocyclic ring, or an optionally substituted group selected from alkyl, heteroalkyl, aryl, heteroaryl, alkylaryl, alkylheteroaryl, or alkylheterocycloalkyl;
G is

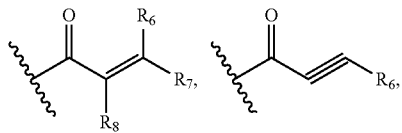

-continued

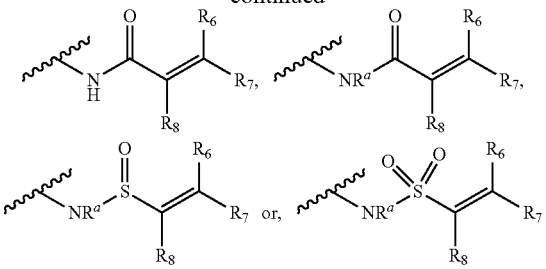

where R$^a$ is H, substituted or unsubstituted alkyl, substituted or unsubstituted cycloalkyl; and either
R$_7$ and R$_8$ are H;
R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);
R$_6$ and R$_8$ are H;
R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or
R$_7$ and R$_8$ taken together form a bond;
R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or
R$_5$ is H, halogen, -L$_6$-(substituted or unsubstituted C$_1$-C$_3$ alkyl), -L$_6$-(substituted or unsubstituted C$_2$-C$_4$ alkenyl), -L$_6$-(substituted or unsubstituted heteroaryl), or -L$_6$-(substituted or unsubstituted aryl), wherein L$_6$ is a bond, O, S, —S(=O), S(=O)$_2$, NH, C(O), —NHC(O)O, —OC(O)NH, —NHC(O), or —C(O)NH;
each R$_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_9$ and $R_{10}$ can together form a 5-, 6-, 7-, or 8-membered heterocyclic ring; or each $R_{11}$ is independently selected from H, —S(=O)$_2$R$_8$, —S(=O)$_2$NH$_2$, —C(O)R$_8$, —CN, —NO$_2$, heteroaryl, or heteroalkyl; and pharmaceutically active metabolites, pharmaceutically acceptable solvates, pharmaceutically acceptable salts, or pharmaceutically acceptable prodrugs thereof.

In another embodiment are provided pharmaceutically acceptable salts of compounds of Formula (A1). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (A1), including those in which the ester group is selected from a formate, acetate, propionate, butyrate, acrylate and ethylsuccinate.

In another embodiment are pharmaceutically acceptable carbamates of compounds of Formula (A1). In another embodiment are pharmaceutically acceptable N-acyl derivatives of compounds of Formula (A1). Examples of N-acyl groups include N-acetyl and N-ethoxycarbonyl groups.

In a further or alternative embodiment, the compound of Formula (A1) has the following structure of Formula (B1):

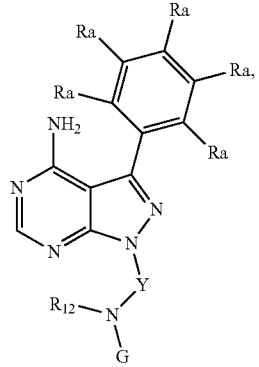

Formula (B1)

wherein:

Y is an optionally substituted group selected from among alkylene, heteroalkylene, arylene, heteroarylene, alkylenearylene, alkyleneheteroarylene, and alkyleneheterocycloalkylene;

each $R_a$ is independently H, halogen, —CF$_3$, —CN, —NO$_2$, OH, NH$_2$, -L$_a$-(substituted or unsubstituted alkyl), -L$_a$-(substituted or unsubstituted alkenyl), -L$_a$-(substituted or unsubstituted heteroaryl), or -L$_a$-(substituted or unsubstituted aryl), wherein L$_a$ is a bond, O, S, —S(=O), —S(=O)$_2$, NH, C(O), CH$_2$, —NHC(O)O, —NHC(O), or —C(O)NH;

G is

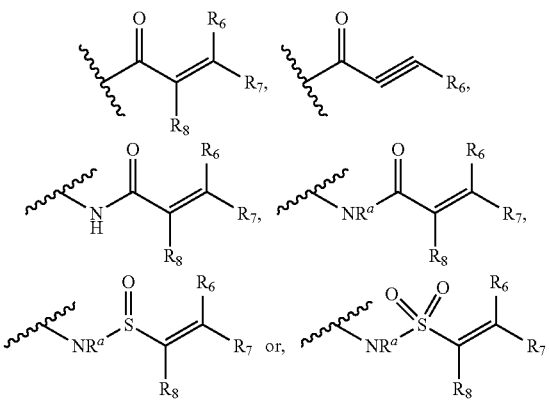

where $R^a$ is H, substituted or unsubstituted alkyl, substituted or unsubstituted cycloalkyl; and either $R_7$ and $R_8$ are H;

$R_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);

$R_6$ and $R_8$ are H;

$R_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or $R_7$ and $R_8$ taken together form a bond;

$R_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

$R_{12}$ is H or lower alkyl; or

Y and $R_{12}$ taken together form a 4-, 5-, or 6-membered heterocyclic ring; and pharmaceutically acceptable active metabolites, pharmaceutically acceptable solvates, pharmaceutically acceptable salts, or pharmaceutically acceptable prodrugs thereof.

In further or alternative embodiments, G is selected from among

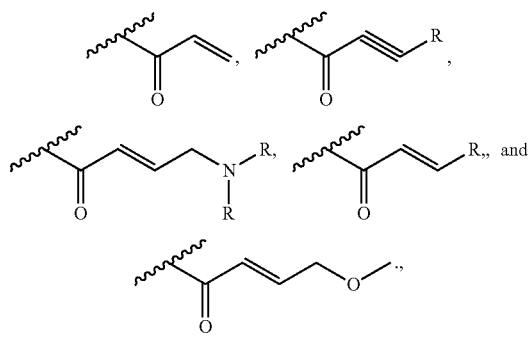

where R is H, alkyl, alkylhydroxy, heterocycloalkyl, heteroaryl, alkylalkoxy, alkylalkoxyalkyl.

In further or alternative embodiments,

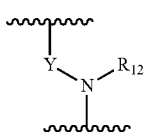

is selected from among

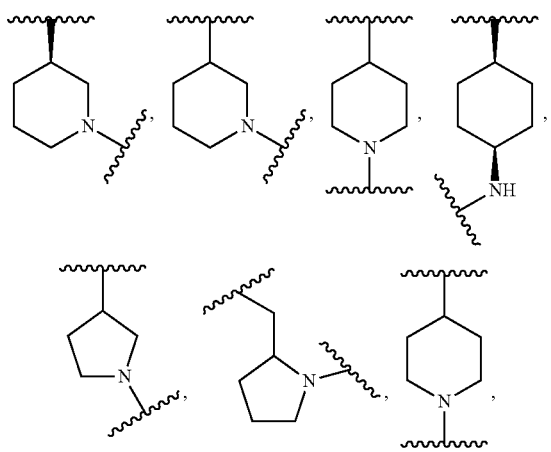

In further or alternative embodiment, the compound of Formula (B1) has the following structure of Formula (C1):

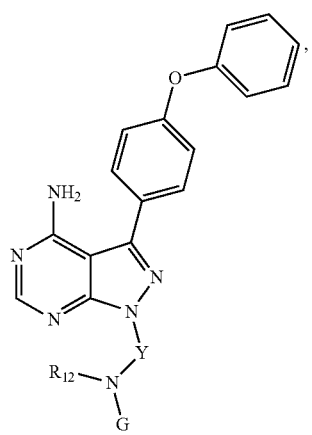

Formula (C1)

Y is an optionally substituted group selected from among alkyl, heteroalkyl, aryl, heteroaryl, alkylaryl, alkylheteroaryl, and alkylheterocycloalkyl;

$R_{12}$ is H or lower alkyl; or

Y and $R_{12}$ taken together form a 4-, 5-, or 6-membered heterocyclic ring;

G is

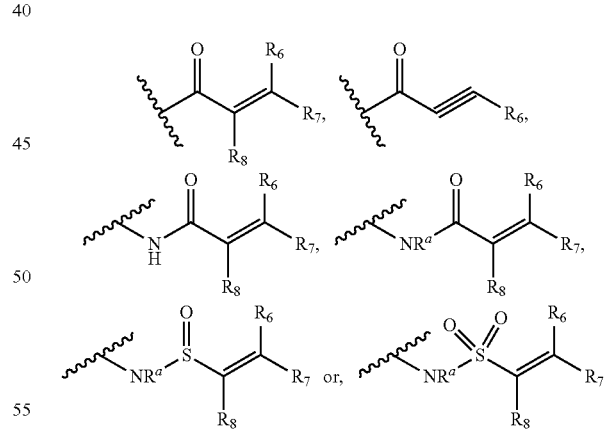

where $R^a$ is H, substituted or unsubstituted alkyl, substituted or unsubstituted cycloalkyl; and either $R_7$ and $R_8$ are H;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);

R$_6$ and R$_8$ are H;

R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or R$_7$ and R$_8$ taken together form a bond;

R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); and pharmaceutically acceptable active metabolites, pharmaceutically acceptable solvates, pharmaceutically acceptable salts, or pharmaceutically acceptable prodrugs thereof.

In a further or alternative embodiment, the "G" group of any of Formula (A1), Formula (B1), or Formula (C1) is any group that is used to tailor the physical and biological properties of the molecule. Such tailoring/modifications are achieved using groups which modulate Michael acceptor chemical reactivity, acidity, basicity, lipophilicity, solubility and other physical properties of the molecule. The physical and biological properties modulated by such modifications to G include, by way of example only, enhancing chemical reactivity of Michael acceptor group, solubility, in vivo absorption, and in vivo metabolism. In addition, in vivo metabolism includes, by way of example only, controlling in vivo PK properties, off-target activities, potential toxicities associated with cypP450 interactions, drug-drug interactions, and the like. Further, modifications to G allow for the tailoring of the in vivo efficacy of the compound through the modulation of, by way of example, specific and non-specific protein binding to plasma proteins and lipids and tissue distribution in vivo.

In one aspect are compounds (including irreversible inhibitors of ACKs, including Btk and its cysteine homologs) having the structure of Formula (D1):

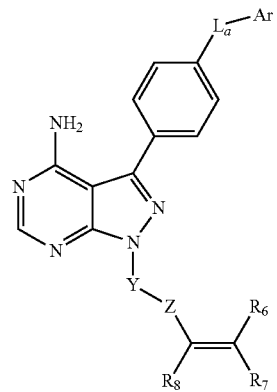

Formula (D1)

wherein

L$_a$ is CH$_2$, O, NH or S;

Ar is an optionally substituted aromatic carbocycle or an aromatic heterocycle;

Y is an optionally substituted group selected from among alkylene, heteroalkylene, arylene, heteroarylene, alkylenearylene, alkyleneheteroarylene, and alkyleneheterocycloalkylene, or combination thereof;

Z is C(=O), NHC(=O), NR$^a$C(=O), NR$^a$S(=O)$_x$, where x is 1 or 2, and R$^a$ is H, substituted or unsubstituted alkyl, substituted or unsubstituted cycloalkyl; and either R$_7$ and R$_8$ are H;

R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);

R$_6$ and R$_8$ are H;

R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or R$_7$ and R$_8$ taken together form a bond;

R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), $C_1$-$C_8$alkylethers, $C_1$-$C_8$alkylamides, or $C_1$-$C_4$alkyl($C_2$-$C_8$heterocycloalkyl);
or combinations thereof; and
pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (D1). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (D1), including those in which the ester group is selected from a formate, acetate, propionate, butyrate, acrylate and ethylsuccinate.

In another embodiment are pharmaceutically acceptable carbamates of compounds of Formula (D1). In another embodiment are pharmaceutically acceptable N-acyl derivatives of compounds of Formula (D1). Examples of N-acyl groups include N-acetyl and N-ethoxycarbonyl groups.

In a further or alternative embodiment, $L_a$ is O.
In a further or alternative embodiment, Ar is phenyl.
In a further or alternative embodiment, Z is C(=O), NHC(=O), or NCH$_3$C(=O).
In a further or alternative embodiment, each of $R_1$, $R_2$, and $R_3$ is H.

In one aspect are compounds (including irreversible inhibitors of ACKs, including Btk and its cysteine homologs) having the structure of Formula (D1):

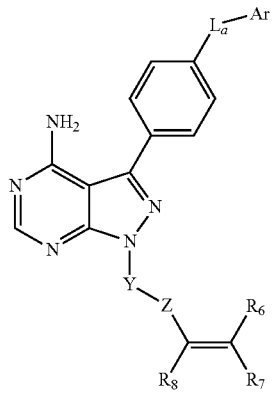

Formula (D1)

wherein:
$L_a$ is CH$_2$, O, NH or S;
Ar is a substituted or unsubstituted aryl, or a substituted or unsubstituted heteroaryl;
Y is an optionally substituted group selected from among alkylene, heteroalkylene, arylene, heteroarylene, alkylenearylene, alkyleneheteroarylene, alkylenecycloalkylene and alkyleneheterocycloalkylene;
Z is C(=O), NHC(=O), NR$^a$C(=O), NR$^a$S(=O)$_x$, where x is 1 or 2, and R$^a$ is substituted or unsubstituted alkyl, substituted or unsubstituted cycloalkyl; and
either
$R_7$ and $R_8$ are H;
$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);
$R_6$ and $R_8$ are H;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or
$R_7$ and $R_8$ taken together form a bond;
$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); and
pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (D1). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (D1), including those in which the ester group is selected from a formate, acetate, propionate, butyrate, acrylate and ethylsuccinate.

In another embodiment are pharmaceutically acceptable carbamates of compounds of Formula (D1). In another embodiment are pharmaceutically acceptable N-acyl derivatives of compounds of Formula (D1). Examples of N-acyl groups include N-acetyl and N-ethoxycarbonyl groups.

For any and all of the embodiments, substituents can be selected from among from a subset of the listed alternatives. For example, in some embodiments, $L_a$ is $CH_2$, O, or NH. In other embodiments, $L_a$ is O or NH. In yet other embodiments, $L_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is $C(=O)$, $OC(=O)$, $NHC(=O)$, $S(=O)_x$, $OS(=O)_x$, or $NHS(=O)_x$. In some other embodiments, Z is $C(=O)$, $NHC(=O)$, or $S(=O)_2$.

In some embodiments, $R_7$ and $R_8$ are independently selected from among H, unsubstituted $C_1$-$C_4$ alkyl, substituted $C_1$-$C_4$alkyl, unsubstituted $C_1$-$C_4$heteroalkyl, and substituted $C_1$-$C_4$heteroalkyl; or $R_7$ and $R_8$ taken together form a bond. In yet other embodiments, each of $R_7$ and $R_8$ is H; or $R_7$ and $R_8$ taken together form a bond.

In some embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-$N(C_1$-$C_3$alkyl$)_2$, substituted or unsubstituted aryl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In some other embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-$N(C_1$-$C_3$alkyl$)_2$, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In yet other embodiments, $R_6$ is H, substituted or unsubstituted $C_1$-$C_4$alkyl, $-CH_2-O-(C_1$-$C_3$alkyl), $-CH_2-N(C_1$-$C_3$alkyl$)_2$, $C_1$-$C_4$alkyl(phenyl), or $C_1$-$C_4$alkyl(5- or 6-membered heteroaryl). In some embodiments, $R_6$ is H, substituted or unsubstituted $C_1$-$C_4$alkyl, $-CH_2-O-(C_1$-$C_3$alkyl), $-CH_2-N(C_1$-$C_3$alkyl$)_2$, $C_1$-$C_4$alkyl(phenyl), or $C_1$-$C_4$alkyl(5- or 6-membered heteroaryl containing 1 or 2 N atoms), or $C_1$-$C_4$alkyl(5- or 6-membered heterocycloalkyl containing 1 or 2 N atoms).

In some embodiments, Y is an optionally substituted group selected from among alkylene, heteroalkylene, cycloalkylene, and heterocycloalkylene. In other embodiments, Y is an optionally substituted group selected from among $C_1$-$C_6$alkylene, $C_1$-$C_6$heteroalkylene, 4-, 5-, 6- or 7-membered cycloalkylene, and 4-, 5-, 6- or 7-membered heterocycloalkylene. In yet other embodiments, Y is an optionally substituted group selected from among $C_1$-$C_6$alkylene, $C_1$-$C_6$heteroalkylene, 5-, or 6-membered cycloalkylene, and 5-, or 6-membered heterocycloalkylene containing 1 or 2 N atoms. In some other embodiments, Y is a 5-, or 6-membered cycloalkylene, or a 5-, or 6-membered heterocycloalkylene containing 1 or 2 N atoms.

In one aspect are compounds (including irreversible inhibitors of ACKs, including Btk and its cysteine homologs) having the structure of Formula (A2-A6):

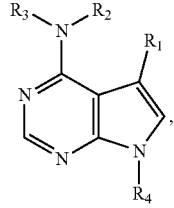

Formula (A2)

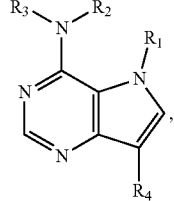

Formula (A3)

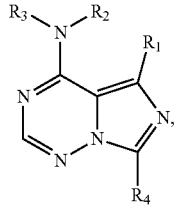

Formula (A4)

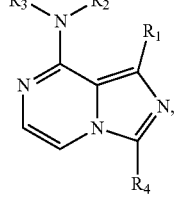

Formula (A5)

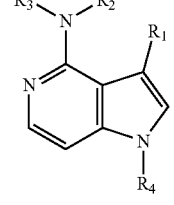

Formula (A6)

wherein
  A is independently selected from N or $CR_5$;
  $R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, $-S(=O)$, $-S(=O)_2$, $C(=O)$, -(substituted or unsubstituted $C_1$-$C_6$ alkyl), or -(substituted or unsubstituted $C_2$-$C_6$ alkenyl);
  $R_2$ and $R_3$ are independently selected from H, lower alkyl and substituted lower alkyl;

R$_4$ is L$_3$-X-L$_4$-G, wherein,
  L$_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
  X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
  L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
  or L$_3$, X and L$_4$ taken together form a nitrogen containing heterocyclic ring;
  G is

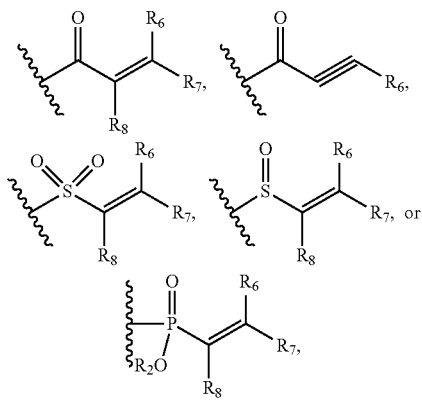

wherein, R$_6$, R$_7$ and R$_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
R$_5$ is H, halogen, -L$_6$-(substituted or unsubstituted C$_1$-C$_3$ alkyl), -L$_6$-(substituted or unsubstituted C$_2$-C$_4$ alkenyl), -L$_6$-(substituted or unsubstituted heteroaryl), or -L$_6$-(substituted or unsubstituted aryl), wherein L$_6$ is a bond, O, S, —S(=O), S(=O)$_2$, NH, C(O), —NHC(O)O, —OC(O)NH, —NHC(O), or —C(O)NH;
each R$_9$ is independently selected from among H, substituted or unsubstituted lower alkyl, and substituted or unsubstituted lower cycloalkyl;
each R$_{10}$ is independently H, substituted or unsubstituted lower alkyl, or substituted or unsubstituted lower cycloalkyl; or
two R$_{10}$ groups can together form a 5-, 6-, 7-, or 8-membered heterocyclic ring; or
R$_9$ and R$_{10}$ can together form a 5-, 6-, 7-, or 8-membered heterocyclic ring; or each R$_{11}$ is independently selected from H, —S(=O)$_2$R$_8$, —S(=O)$_2$NH$_2$, —C(O)R$_8$, —CN, —NO$_2$, heteroaryl, or heteroalkyl; and pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (A2-A6). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (A2-A6), including those in which the ester group is selected from a formate, acetate, propionate, butyrate, acrylate and ethylsuccinate.

In another embodiment are pharmaceutically acceptable carbamates of compounds of Formula (A2-A6). In another embodiment are pharmaceutically acceptable N-acyl derivatives of compounds of Formula (A2-A6). Examples of N-acyl groups include N-acetyl and N-ethoxycarbonyl groups.

In a further or alternative embodiment, the compound of Formula (A2-A6) has the following structure of Formula (B2-B6):

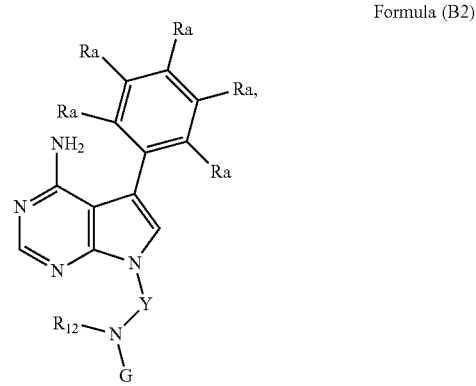

Formula (B2)

-continued

Formula (B3)

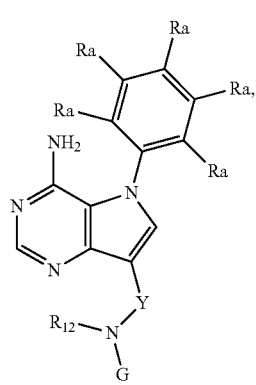

Formula (B4)

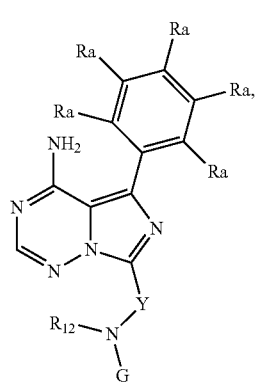

Formula (B5)

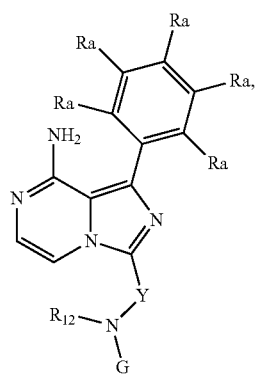

Formula (B6)

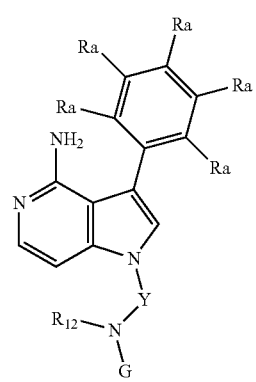

wherein:
Y is alkylene or substituted alkylene, or a 4-, 5-, or 6-membered cycloalkylene ring;
each $R_a$ is independently H, halogen, —$CF_3$, —CN, —$NO_2$, OH, $NH_2$, -$L_a$-(substituted or unsubstituted alkyl), -$L_a$-(substituted or unsubstituted alkenyl), -$L_a$-(substituted or unsubstituted heteroaryl), or -$L_a$-(substituted or unsubstituted aryl), wherein $L_a$ is a bond, O, S, —S(=O), —S(=O)$_2$, NH, C(O), $CH_2$, —NHC(O)O, —NHC(O), or —C(O)NH;

G is

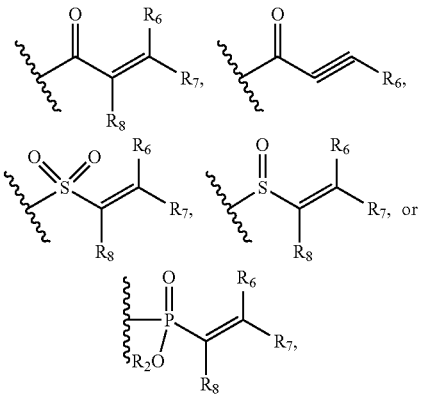

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_{12}$ is H or lower alkyl; or

Y and $R_{12}$ taken together form a 4-, 5-, or 6-membered heterocyclic ring; and pharmaceutically acceptable active metabolites, pharmaceutically acceptable solvates, pharmaceutically acceptable salts, or pharmaceutically acceptable prodrugs thereof.

In further or alternative embodiments, G is selected from among

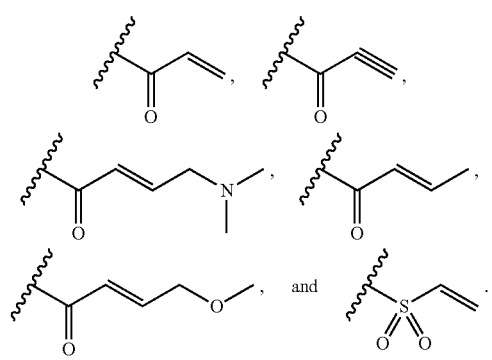

In further or alternative embodiments,

is selected from among
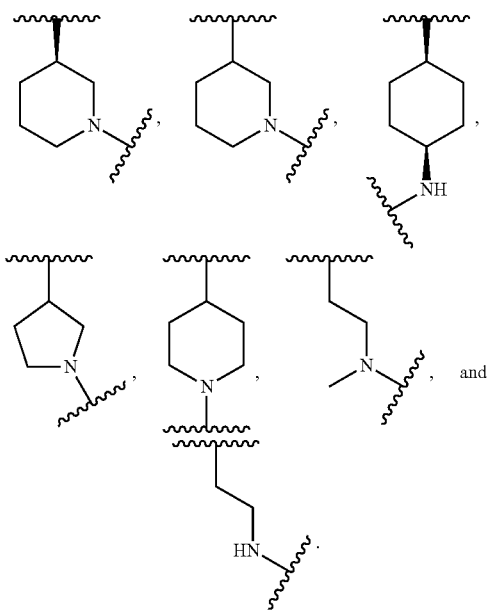
In further or alternative embodiment, the compound of Formula (B2-B6) has the following structure of Formula (C2-C6):
Formula (C2)
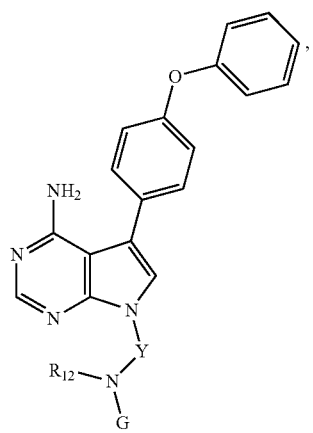
Formula (C3)
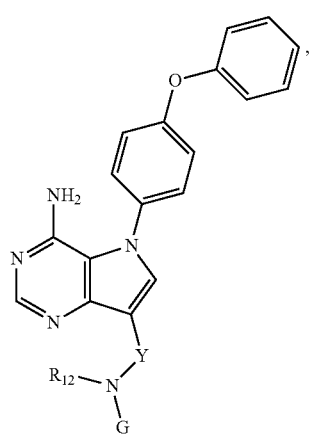
Formula (C4)
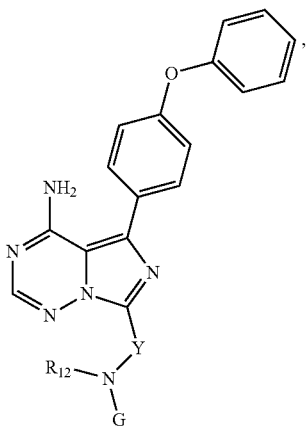
Formula (C5)
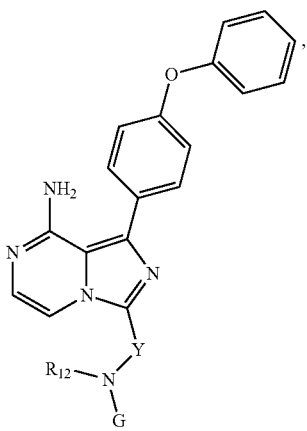
Formula (C6)
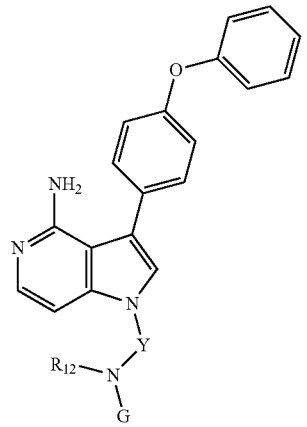
Y is alkylene or substituted alkylene, or a 4-, 5-, or 6-membered cycloalkylene ring;
$R_{12}$ is H or lower alkyl; or
Y and $R_{12}$ taken together form a 4-, 5-, or 6-membered heterocyclic ring;
G is
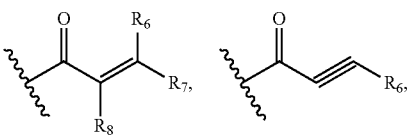

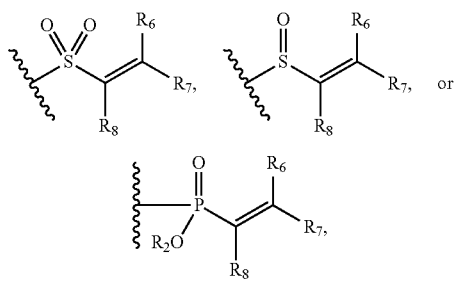

wherein,

R$_6$, R$_7$ and R$_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl; and pharmaceutically acceptable active metabolites, pharmaceutically acceptable solvates, pharmaceutically acceptable salts, or pharmaceutically acceptable prodrugs thereof.

In a further or alternative embodiment, the "G" group of any of Formula (A2-A6), Formula (B2-B6), or Formula (C2-C6) is any group that is used to tailor the physical and biological properties of the molecule. Such tailoring/modifications are achieved using groups which modulate Michael acceptor chemical reactivity, acidity, basicity, lipophilicity, solubility and other physical properties of the molecule. The physical and biological properties modulated by such modifications to G include, by way of example only, enhancing chemical reactivity of Michael acceptor group, solubility, in vivo absorption, and in vivo metabolism. In addition, in vivo metabolism includes, by way of example only, controlling in vivo PK properties, off-target activities, potential toxicities associated with cypP450 interactions, drug-drug interactions, and the like. Further, modifications to G allow for the tailoring of the in vivo efficacy of the compound through the modulation of, by way of example, specific and non-specific protein binding to plasma proteins and lipids and tissue distribution in vivo.

In one aspect are compounds (including irreversible inhibitors of ACKs, including Btk and its cysteine homologs) having the structure of Formula (D2-D6):

Formula (D2)

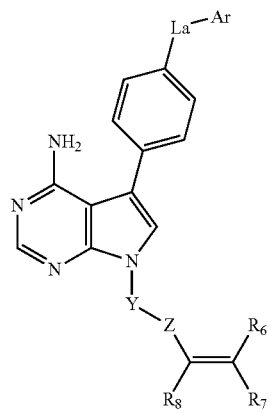

Formula (D3)

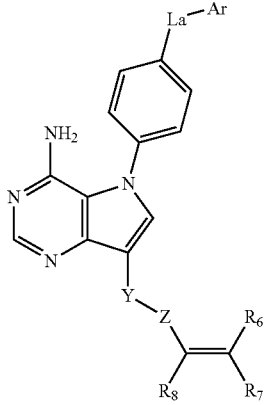

Formula (D4)

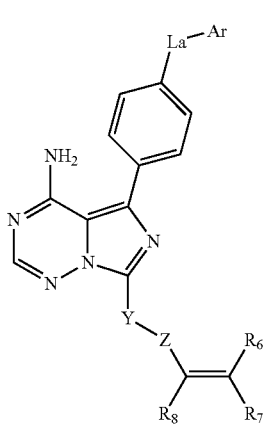

Formula (D5)

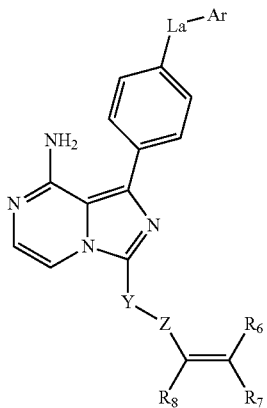

Formula (D6)

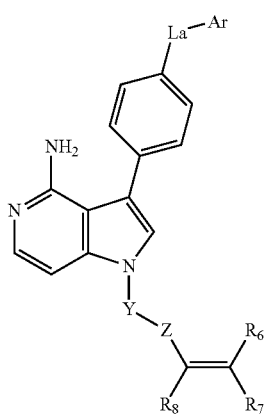

wherein
$L_a$ is $CH_2$, O, NH or S;
Ar is an optionally substituted aromatic carbocycle or an aromatic heterocycle;
Y is an optionally substituted alkylene, heteroalkylene, carbocycloalkylene, heterocycloalkylene, or combination thereof;
Z is C(O), OC(O), NHC(O), C(S), $S(O)_x$, $OS(O)_x$, $NHS(O)_x$, where x is 1 or 2; and
$R_6$, $R_7$, and $R_8$ are independently selected from H, alkyl, heteroalkyl, carbocycle, heterocycle, or combinations thereof; and pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (D2-D6). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (D2-D6), including those in which the ester group is selected from a formate, acetate, propionate, butyrate, acrylate and ethylsuccinate.

In another embodiment are pharmaceutically acceptable carbamates of compounds of Formula (D2-D6). In another embodiment are pharmaceutically acceptable N-acyl derivatives of compounds of Formula (D2-D6). Examples of N-acyl groups include N-acetyl and N-ethoxycarbonyl groups.

In a further or alternative embodiment, $L_a$ is O.
In a further or alternative embodiment, Ar is phenyl.
In a further or alternative embodiment, Z is C(O).
In a further or alternative embodiment, each of $R_1$, $R_2$, and $R_3$ is H.

In one aspect are compounds (including irreversible inhibitors of ACKs, including Btk and its cysteine homologs) having the structure of Formula (D2-D6):

Formula (D2)

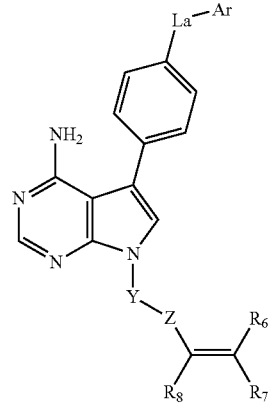

Formula (D3)

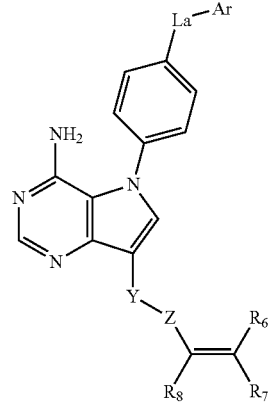

Formula (D4)

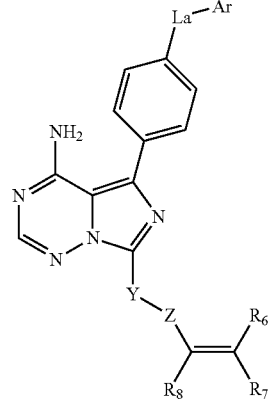

Formula (D5)

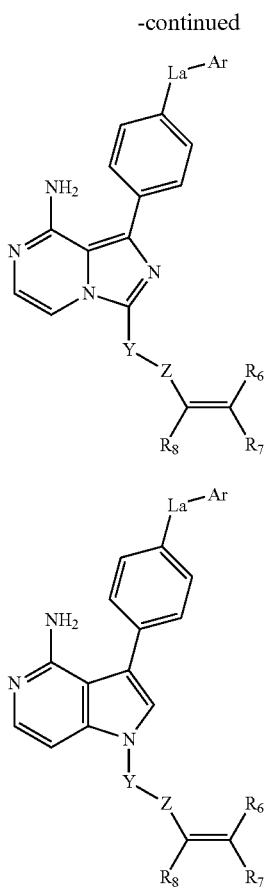

Formula (D6)

wherein:
L$_a$ is CH$_2$, O, NH or S;
Ar is a substituted or unsubstituted aryl, or a substituted or unsubstituted heteroaryl;
Y is an optionally substituted group selected from among alkylene, heteroalkylene, cycloalkylene, heterocycloalkylene, arylene, and heteroarylene;
Z is C(═O), OC(═O), NHC(═O), C(═S), S(═O)$_x$, OS(═O)$_x$, NHS(═O)$_x$, where x is 1 or 2;
R$_7$ and R$_8$ are independently selected from among H, unsubstituted C$_1$-C$_4$alkyl, substituted C$_1$-C$_4$alkyl, unsubstituted C$_1$-C$_4$heteroalkyl, substituted C$_1$-C$_4$heteroalkyl, unsubstituted C$_3$-C$_6$cycloalkyl, substituted C$_3$-C$_6$cycloalkyl, unsubstituted C$_2$-C$_6$heterocycloalkyl, and substituted C$_2$-C$_6$heterocycloalkyl; or
R$_7$ and R$_8$ taken together form a bond;
R$_6$ is H, substituted or unsubstituted C$_1$-C$_4$alkyl, substituted or unsubstituted C$_1$-C$_4$heteroalkyl, C$_1$-C$_6$alkoxyalkyl, C$_1$-C$_8$alkylaminoalkyl, substituted or unsubstituted C$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_4$alkyl(C$_3$-C$_8$cycloalkyl), or C$_1$-C$_4$alkyl(C$_2$-C$_8$heterocycloalkyl); and pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (D2-D6). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (D2-D6), including those in which the ester group is selected from a formate, acetate, propionate, butyrate, acrylate and ethylsuccinate.

In another embodiment are pharmaceutically acceptable carbamates of compounds of Formula (D2-D6). In another embodiment are pharmaceutically acceptable N-acyl derivatives of compounds of Formula (D2-D6).

For any and all of the embodiments, substituents can be selected from among from a subset of the listed alternatives. For example, in some embodiments, L$_a$ is CH$_2$, O, or NH. In other embodiments, L$_a$ is O or NH. In yet other embodiments, L$_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is C(═O), OC(═O), NHC(═O), S(═O)$_x$, OS(═O)$_x$, or NHS(═O)$_x$. In some other embodiments, Z is C(═O), NHC(═O), or S(═O)$_2$.

In some embodiments, R$_7$ and R$_8$ are independently selected from among H, unsubstituted C$_1$-C$_4$ alkyl, substituted C$_1$-C$_4$alkyl, unsubstituted C$_1$-C$_4$heteroalkyl, and substituted C$_1$-C$_4$heteroalkyl; or R$_7$ and R$_8$ taken together form a bond. In yet other embodiments, each of R$_7$ and R$_8$ is H; or R$_7$ and R$_8$ taken together form a bond.

In some embodiments, R$_6$ is H, substituted or unsubstituted C$_1$-C$_4$alkyl, substituted or unsubstituted C$_1$-C$_4$heteroalkyl, C$_1$-C$_6$alkoxyalkyl, C$_1$-C$_2$alkyl-N(C$_1$-C$_3$alkyl)$_2$, substituted or unsubstituted aryl, substituted or unsubstituted heteroaryl, C$_1$-C$_4$alkyl(aryl), C$_1$-C$_4$alkyl(heteroaryl), C$_1$-C$_4$alkyl(C$_3$-C$_8$cycloalkyl), or C$_1$-C$_4$alkyl(C$_2$-C$_8$heterocycloalkyl). In some other embodiments, R$_6$ is H, substituted or unsubstituted C$_1$-C$_4$alkyl, substituted or unsubstituted C$_1$-C$_4$heteroalkyl, C$_1$-C$_6$alkoxyalkyl, C$_1$-C$_2$alkyl-N(C$_1$-C$_3$alkyl)$_2$, C$_1$-C$_4$alkyl(aryl), C$_1$-C$_4$alkyl(heteroaryl), C$_1$-C$_4$alkyl(C$_3$-C$_8$cycloalkyl), or C$_1$-C$_4$alkyl(C$_2$-C$_8$heterocycloalkyl). In yet other embodiments, R$_6$ is H, substituted or unsubstituted C$_1$-C$_4$alkyl, —CH$_2$—O—(C$_1$-C$_3$alkyl), —CH$_2$—N(C$_1$-C$_3$alkyl)$_2$, C$_1$-C$_4$alkyl(phenyl), or C$_1$-C$_4$alkyl(5- or 6-membered heteroaryl). In some embodiments, R$_6$ is H, substituted or unsubstituted C$_1$-C$_4$alkyl, —CH$_2$—O—(C$_1$-C$_3$alkyl), —CH$_2$—N(C$_1$-C$_3$alkyl)$_2$, C$_1$-C$_4$alkyl(phenyl), or C$_1$-C$_4$alkyl(5- or 6-membered heteroaryl containing 1 or 2 N atoms), or $C_1$-$C_4$alkyl(5- or 6-membered heterocycloalkyl containing 1 or 2 N atoms).

In some embodiments, Y is an optionally substituted group selected from among alkylene, heteroalkylene, cycloalkylene, and heterocycloalkylene. In other embodiments, Y is an optionally substituted group selected from among $C_1$-$C_6$alkylene, $C_1$-$C_6$heteroalkylene, 4-, 5-, 6- or 7-membered cycloalkylene, and 4-, 5-, 6- or 7-membered heterocycloalkylene. In yet other embodiments, Y is an optionally substituted group selected from among $C_1$-$C_6$alkylene, $C_1$-$C_6$heteroalkylene, 5-, or 6-membered cycloalkylene, and 5-, or 6-membered heterocycloalkylene containing 1 or 2 N atoms. In some other embodiments, Y is a 5-, or 6-membered cycloalkylene, or a 5-, or 6-membered heterocycloalkylene containing 1 or 2 N atoms.

Any combination of the groups described above for the various variables is contemplated herein.

In further aspects are compounds (including irreversible inhibitors of ACKs, including Btk and its cysteine homologs) having the structure of compounds of Formula (A1-A6), Formula (B1-B6), Formula (C1-C6), Formula (D1-D6), including, but are not limited to, compounds selected from the group consisting of:

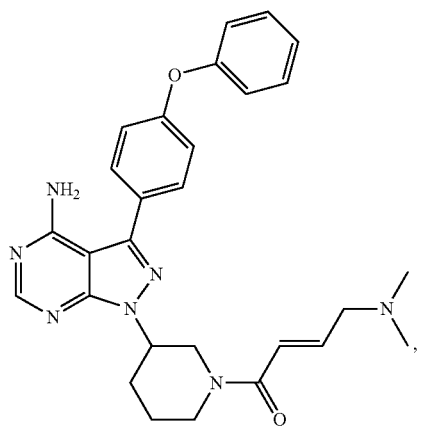

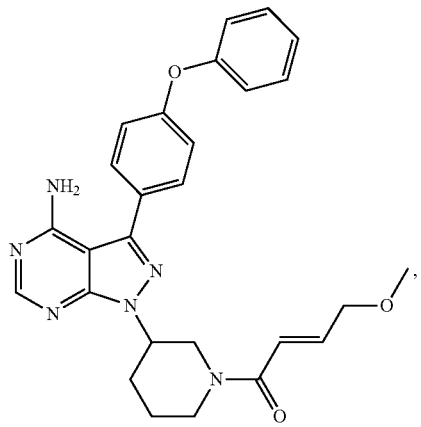

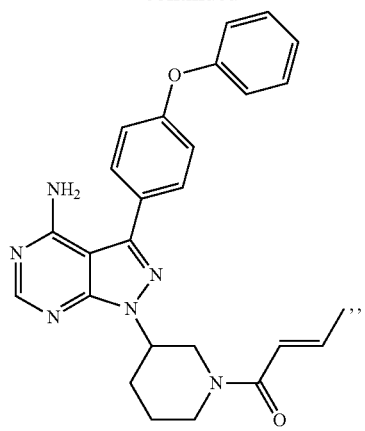

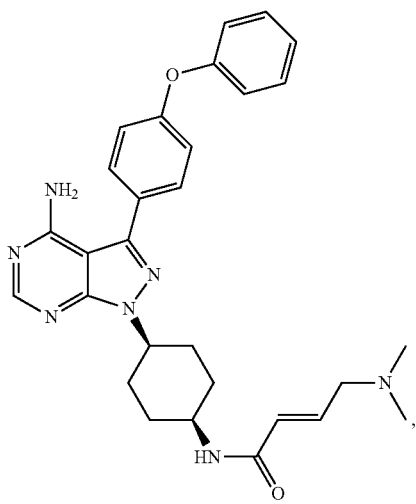

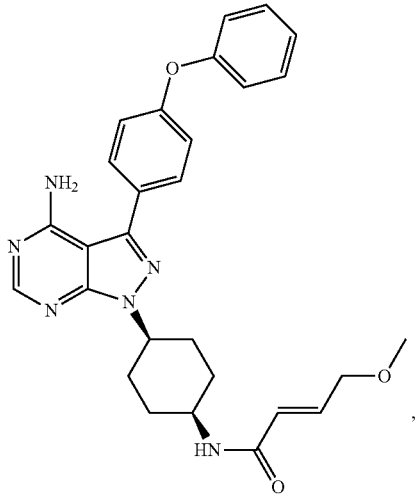

59
-continued
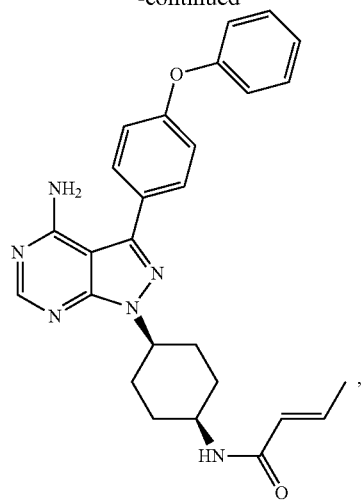
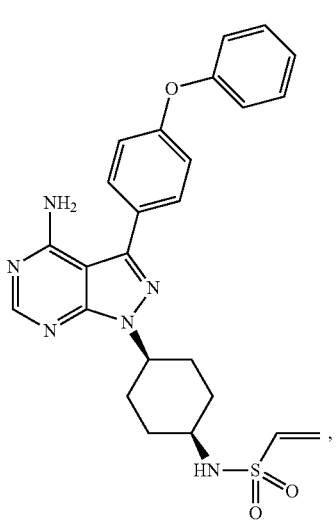
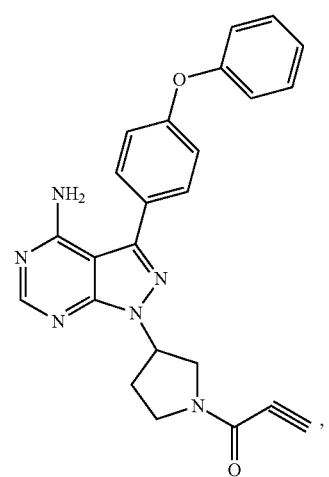 [SMILES: C#CC(=O)N1CCC(n2nc(-c3ccc(Oc4ccccc4)cc3)c3c(N)ncnc32)C1]
60
-continued
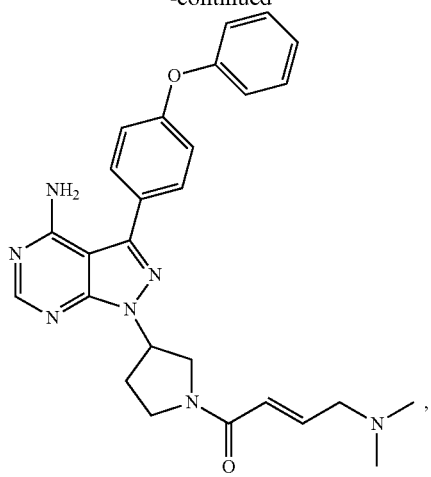
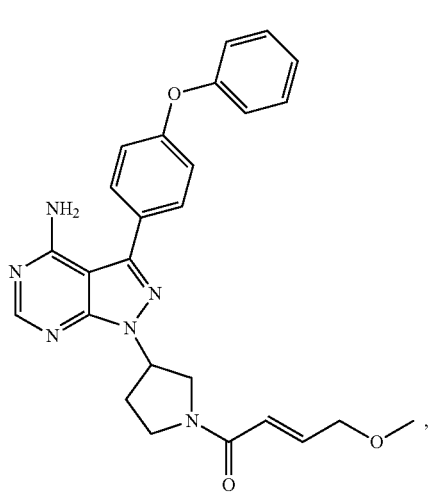
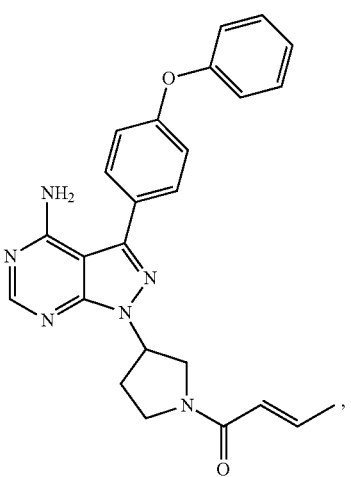

61
-continued
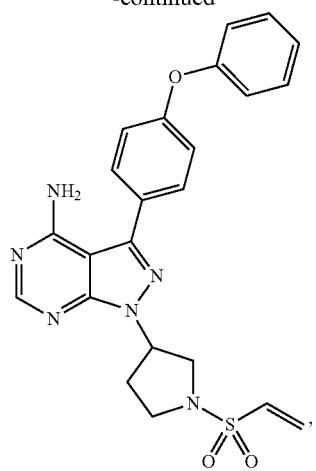
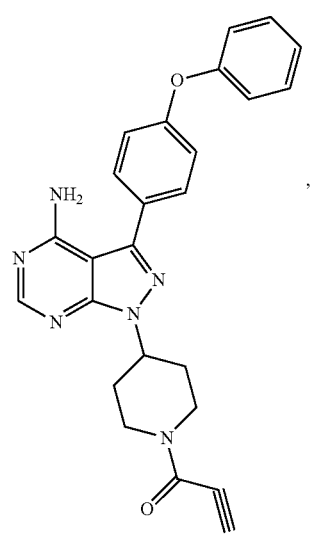
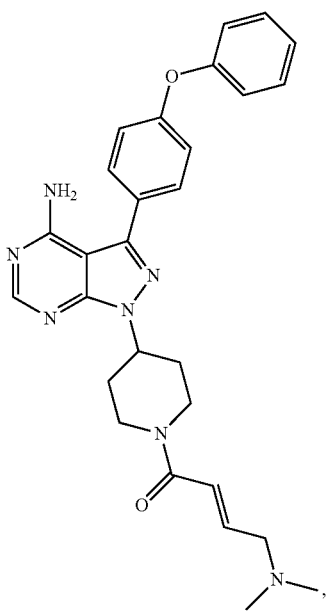
62
-continued
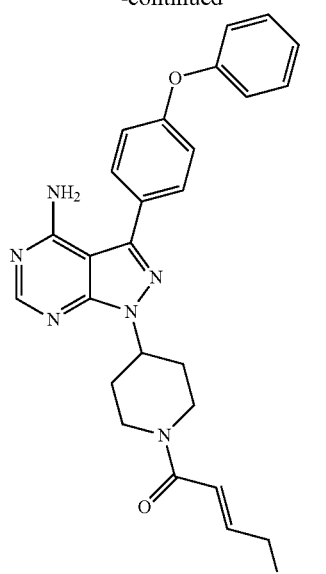
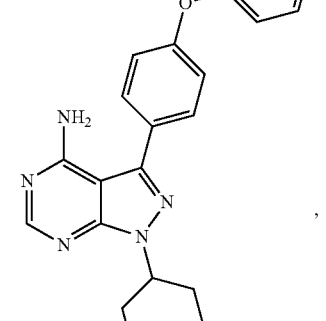
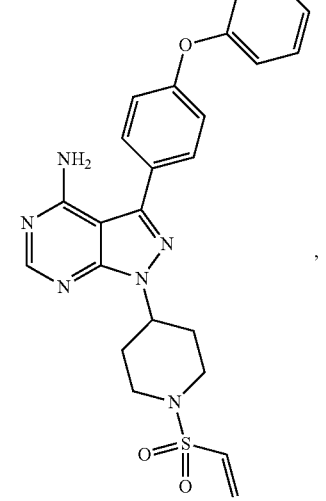

63
-continued
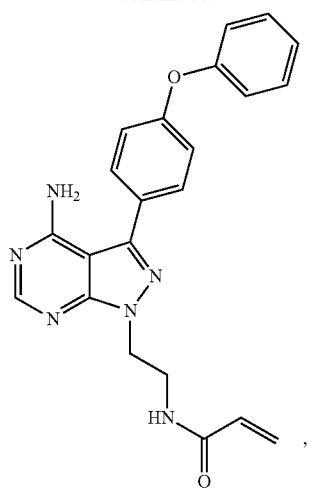
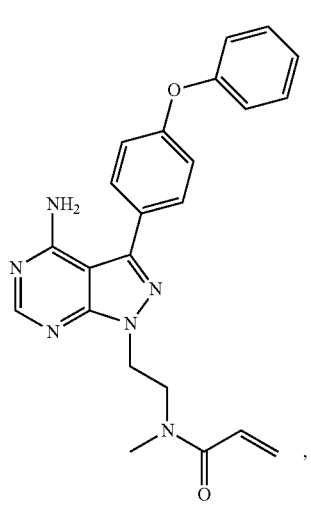
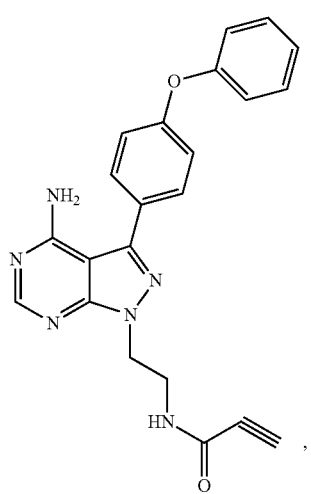
64
-continued
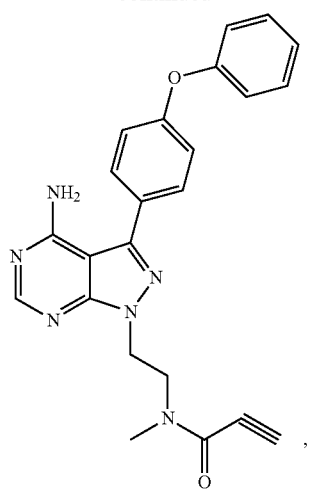
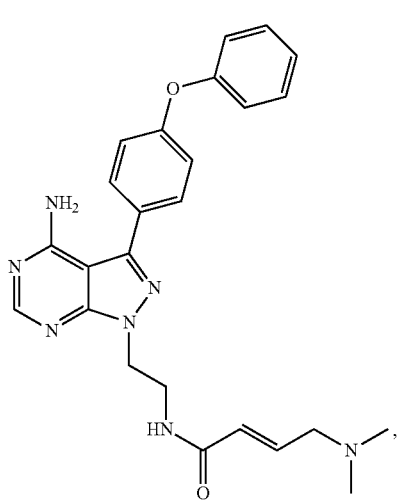
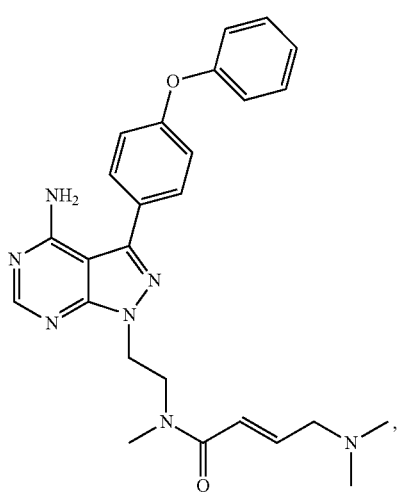

-continued

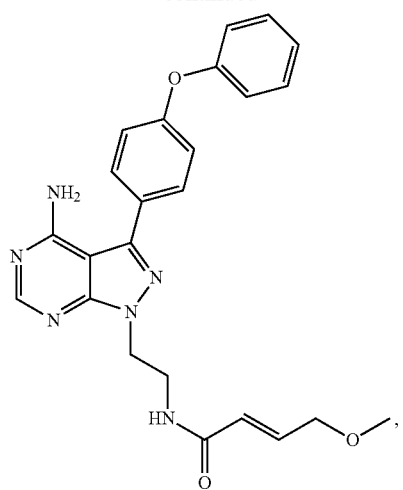

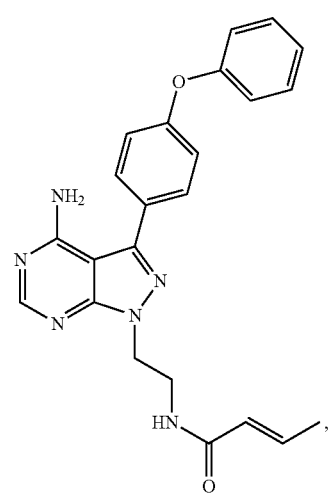

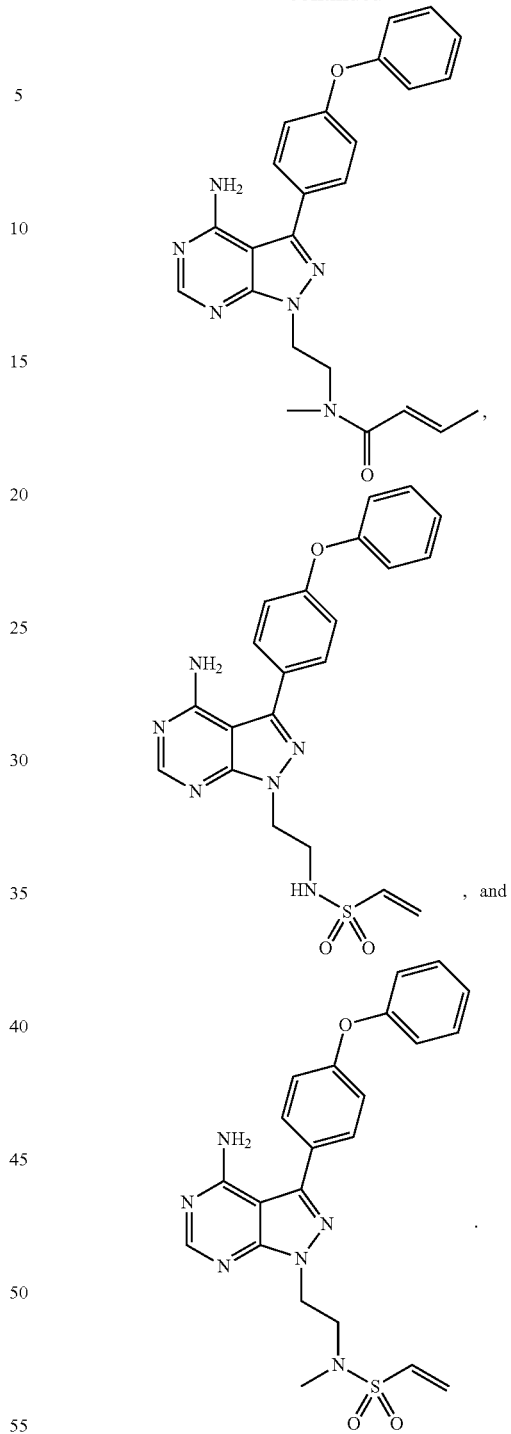

In one aspect are compounds (including irreversible inhibitors of ACKs, including Btk and its cysteine homologs) selected from among: (E)-4-(N-(2-hydroxyethyl)-N-methylamino)-1-(3-(4-phenoxyphenyl)-1H-pyrazolo[3,4-d]pyrimidin-1-yl)piperidin-1-yl)but-2-en-1-one (Compound 3); (E)-1-(3-(4-amino-3-(4-phenoxyphenyl)-1H-pyrazolo[3,4-d]pyrimidin-1-yl)-3-(1H-imidazol-4-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)-4-morpholinobut-2-en-1-one (Compound 5); (E)-1-(4-(4-amino-3-(4-phenoxyphenyl)-1H-pyrazolo[3, 4-d]pyrimidin-1-yl)piperidin-1-yl)-4-(dimethylamino)but-2-en-1-one (Compound 7); (E)-N-((1s,4s)-4-(4-amino-3-(4-phenoxyphenyl)-1H-pyrazolo[3,4-d]pyrimidin-1-yl)cyclohexyl)-4-(dimethylamino)but-2-enamide (Compound 8); N-((1r,4r)-4-(4-amino-3-(4-phenoxyphenyl)-1H-pyrazolo[3,4-d]pyrimidin-1-yl)cyclohexyl)acrylamide (Compound 10); (E)-1-((R)-2-((4-amino-3-(4-phenoxyphenyl)-1H-pyrazolo[3,4-d]pyrimidin-1-yl)methyl)pyrolidin-1-yl)-4-(dimethylamino)but-2-en-1-one (Compound 11); (E)-1-((S)-2-((4-amino-3-(4-phenoxyphenyl)-1H-pyrazolo[3,4-d]pyrimidin-1-yl)methyl)pyrolidin-1-yl)-4-(dimethylamino)but-2-en-1-one (Compound 12); 1-((R)-2-((4-amino-3-(4-phenoxyphenyl)-1H-pyrazolo[3,4-d]pyrimidin-1-yl)methyl)pyrrolidin-1-yl)prop-2-en-1-one (Compound 13); 1-((S)-2-((4-amino-3-(4-phenoxyphenyl)-1H-pyrazolo[3,4-d]pyrimidin-1-yl)methyl)pyrrolidin-1-yl)prop-2-en-1-one (Compound 14); 1((R)-2-((4-amino-3-(4-phenoxyphenyl)-1H-pyrazolo[3,4-d]pyrimidin-1-yl)methyl)pyrrolidin-1-yl)but-2-yn-1-one (Compound 15); 1-((S)-2-((4-amino-3-(4-phenoxyphenyl)-1H-pyrazolo[3,4-d]pyrimidin-1-yl)methyl)pyrrolidin-1-yl)but-2-yn-1-one (Compound 16); 1-((R)-3-(4-amino-3-(4-phenoxyphenyl)-1H-pyrazolo[3,4-d]pyrimidin-1-yl)piperidin-1-yl)but-2-yn-1-one (Compound 17); (E)-N-((1r,4r)-4-(4-amino-3-(4-phenoxyphenyl)-1H-pyrazolo[3,4-d]pyrimidin-1-yl)cyclohexyl-4-(dimethylamino)but-2-enamide (Compound 18); N-(2-(4-amino-3-(4-phenoxyphenyl)-1H-pyrazolo[3,4-d]pyrimidin-1-yl)ethyl)-N-methylacrylamide (Compound 19); (E)-1-(4-(4-amino-3-(4-phenoxyphenyl)-1H-pyrazolo[3,4-d]pyrimidin-1-yl)-4-morpholinobut-2-en-1-one (Compound 20); (E)-1-((S_-2-((4-amino-3-(4-phenoxyphenyl)-1H-pyrazolo[3,4-d]pyrimidin-1-yl)methyl)pyrrolidin-1-yl)-4-morpholinobut-2-en-1-one (Compound 21); N-((1s,4s)-4-(4-amino-3-(4-phenoxyphenyl)-1H-pyrazolo[3,4-d]pyrimidin-1-yl)cyclohexyl)but-2-ynamide (Compound 22); N-(2-(4-amino-3-(4-phenoxyphenyl)-1H-pyrazolo[3,4-d]pyrimidin-1-yl)ethyl)acrylamide (Compound 23); (E)-1-((R)-3-(4-amino-3-(4-phenoxyphenyl)-1H-pyrazolo[3,4-d]pyrimidin-1-yl)piperidin-1-yl)-4-morpholinobut-2-en-1-one (Compound 24); (E)-N-((1s,4s)-4-(4-amino-3-(4-phenoxyphenyl)-1H-pyrazolo[3,4-d]pyrimidin-1-yl)cyclohexyl)-4-morpholinobut-2-enamide (Compound 25).

The compounds of any of Formula (I), Formula (VII), Formula (A1-A6), Formula (B1-B6), Formula (C1-C6), or Formula (D1-D6) irreversibly inhibit Btk and are optionally used to treat patients suffering from Bruton's tyrosine kinase-dependent or Bruton's tyrosine kinase mediated conditions or diseases, including, but not limited to, conditions or diseases characterized by the presence or development of one or more solid tumors.

Preparation of Compounds

Compounds of any of Formula (A1-A6), Formula (B1-B6), Formula (C1-C6), Formula (D1-D6), Formula (I), or Formula (VII) are optionally synthesized using standard synthetic techniques or using such methods known in combination with methods described herein. In additions, solvents, temperatures and other reaction conditions are presented herein for illustration only, and not to limit the scope of the methods and compositions described herein. As a further guide the following synthetic methods may also be utilized.

The reactions are optionally employed in a linear sequence to provide the compounds described herein or used to synthesize fragments which are subsequently joined by the methods described herein and/or documented elsewhere.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

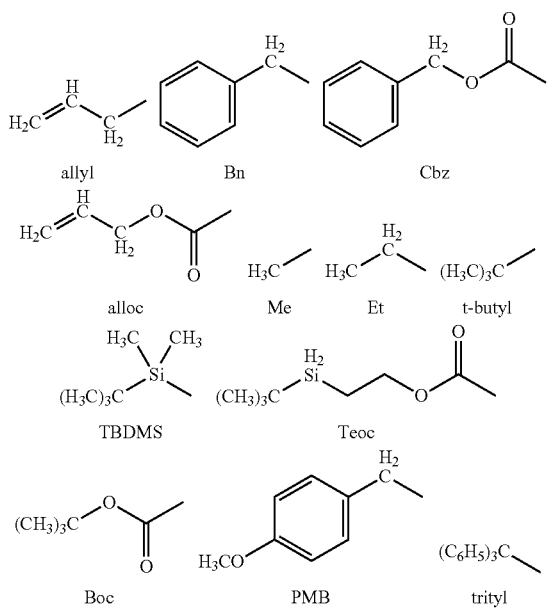

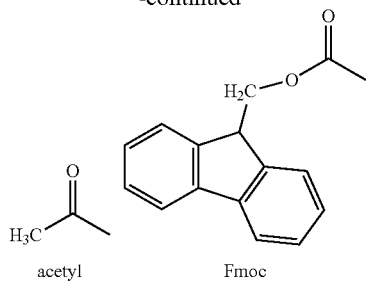

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis of Compounds

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein is either synthesized or obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents are optionally synthesized using techniques and materials, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. As a guide the following synthetic methods may be utilized.

The products of the reactions are optionally isolated and purified, if desired, using conventional techniques, including, but not limited to, filtration, distillation, crystallization, chromatography and the like. Such materials are optionally characterized using conventional means, including physical constants and spectral data.

Compounds described herein are optionally prepared using the synthetic methods described herein as a single isomer or a mixture of isomers.

A non-limiting example of a synthetic approach towards the preparation of compounds of any of Formula (A1-A6), Formula (B1-B6), Formula (C1-C6), Formula (D1-D6), Formula (I), or Formula (VII) is shown in Scheme I.

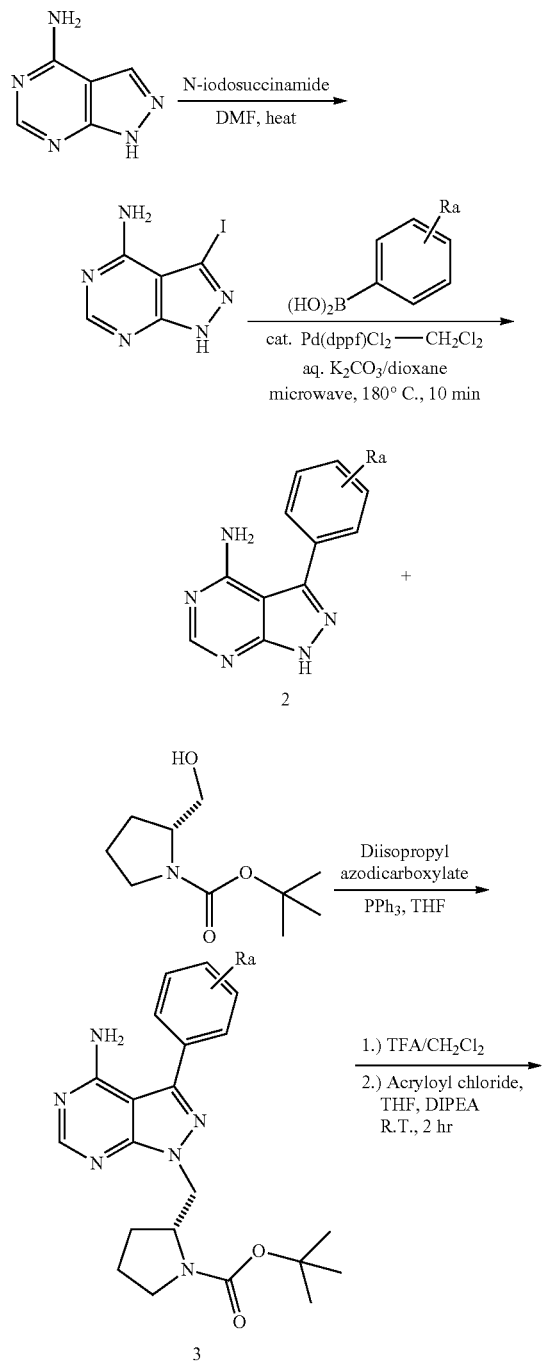

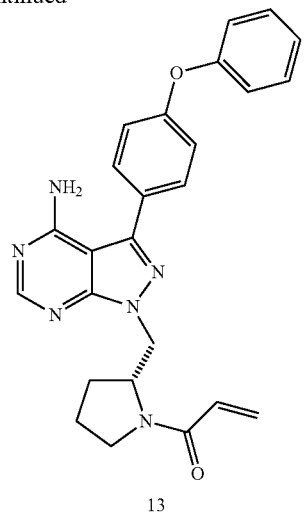

Halogenation of commercially available 1H-pyrazolo[3,4-d]pyrimidin-4-amine provides an entry into the synthesis of compounds of Formula (A1-A6), (B1-B6), (C1-C6) and/or (D1-D6). In one embodiment, 1H-pyrazolo[3,4-d]pyrimidin-4-amine is treated with N-iodosuccinamide to give 3-iodo-1H-pyrazolo[3,4-d]pyrimidin-4-amine. Metal catalyzed cross coupling reactions are then carried out on 3-iodo-1H-pyrazolo[3,4-d]pyrimidin-4-amine. In one embodiment, palladium mediated cross-coupling of a suitably substituted phenyl boronic acid under basic conditions constructs intermediate 2. Intermediate 2 is coupled with N-Boc-3-hydroxypiperidine (as non-limiting example) via Mitsunobu reaction to give the Boc (tert-butyloxycarbonyl) protected intermediate 3. After deprotection with acid, coupling with, but not limited to, an acid chloride, such as, but not limited to, acryloyl chloride, completes the synthesis to give Compound 13.

A non-limiting example of a synthetic approach towards the preparation of compounds containing the imidazotriazine moiety,

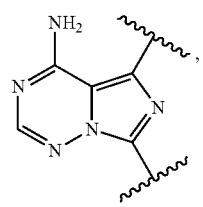 [SMILES: *c1nc(*)n2ncnc(N)c12]

is shown in Scheme II.

Scheme II.

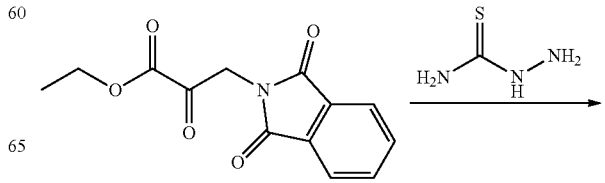

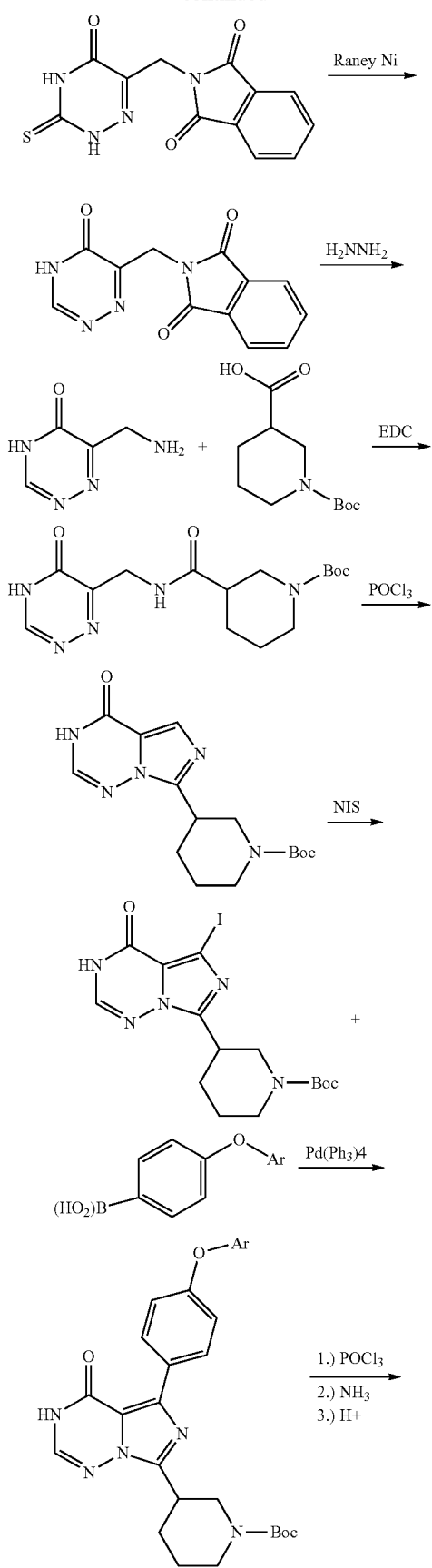
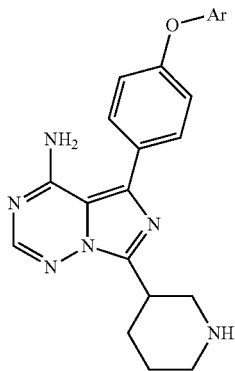
A non-limiting example of a synthetic approach towards the preparation of compounds containing any imidazopyrazine moiety,
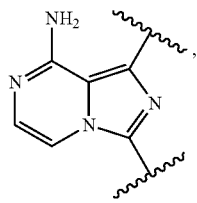
is shown in Scheme III.
Scheme III
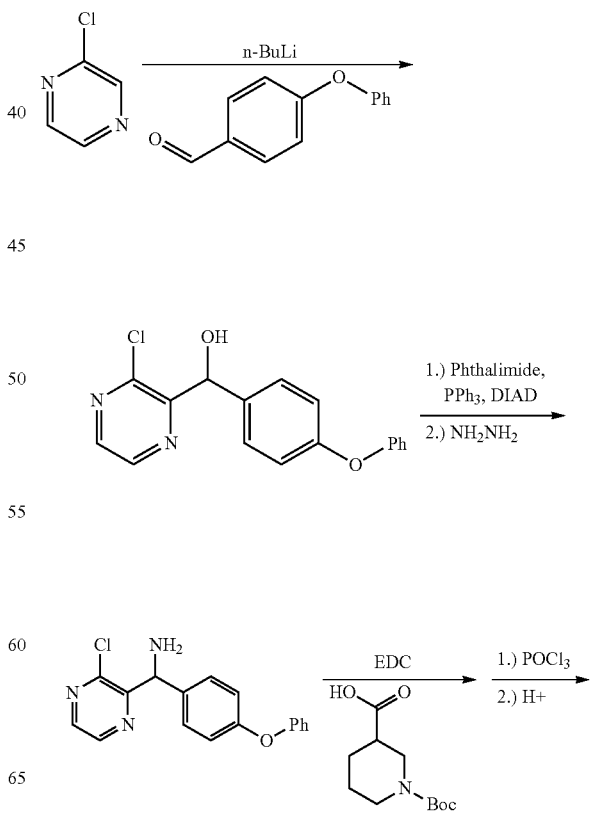

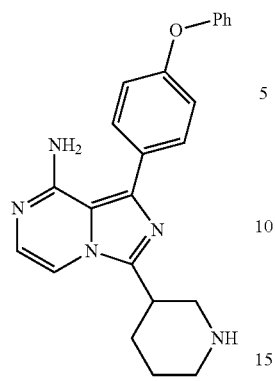
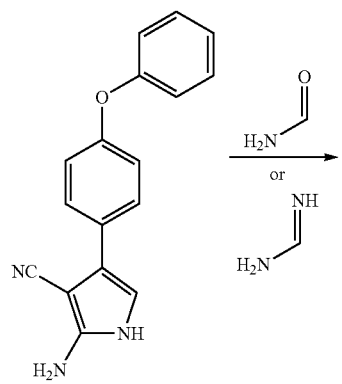
A non-limiting example of a synthetic approach towards the preparation of compounds containing the pyrrolopyrimidine moiety,
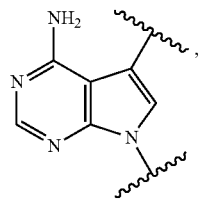 [SMILES: *c1cn(*)c2ncnc(N)c12]
is shown in Scheme IV.
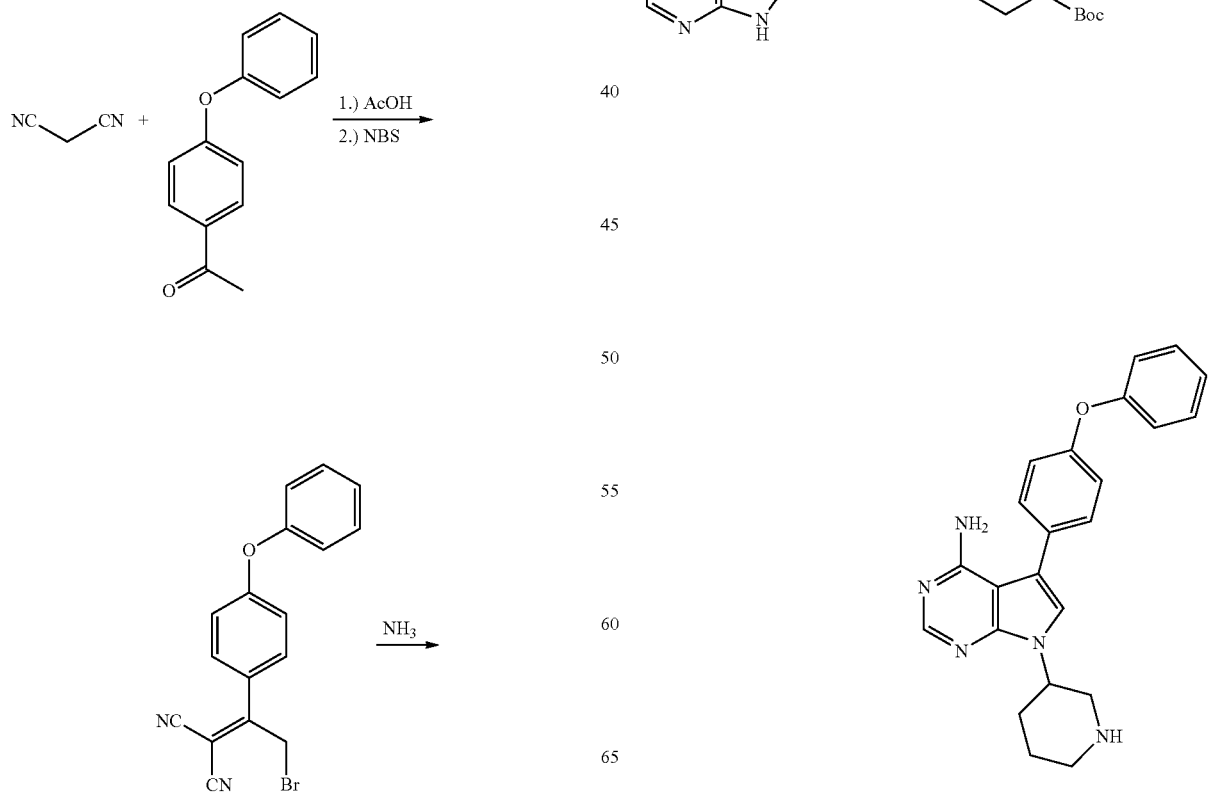

A non-limiting example of a synthetic approach towards the preparation of compounds containing the Azaindole moiety,

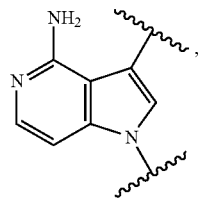 [SMILES: *c1cn(*)c2ccnc(N)c12]

is shown in Scheme V.

A non-limiting example of a synthetic approach towards the preparation of compounds containing the pyrrolopyrimidine moiety,

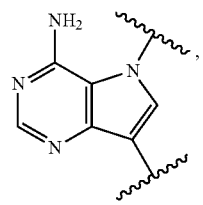 [SMILES: *c1cn(*)c2c(N)ncnc12]

is shown in Scheme VI.

Scheme V.

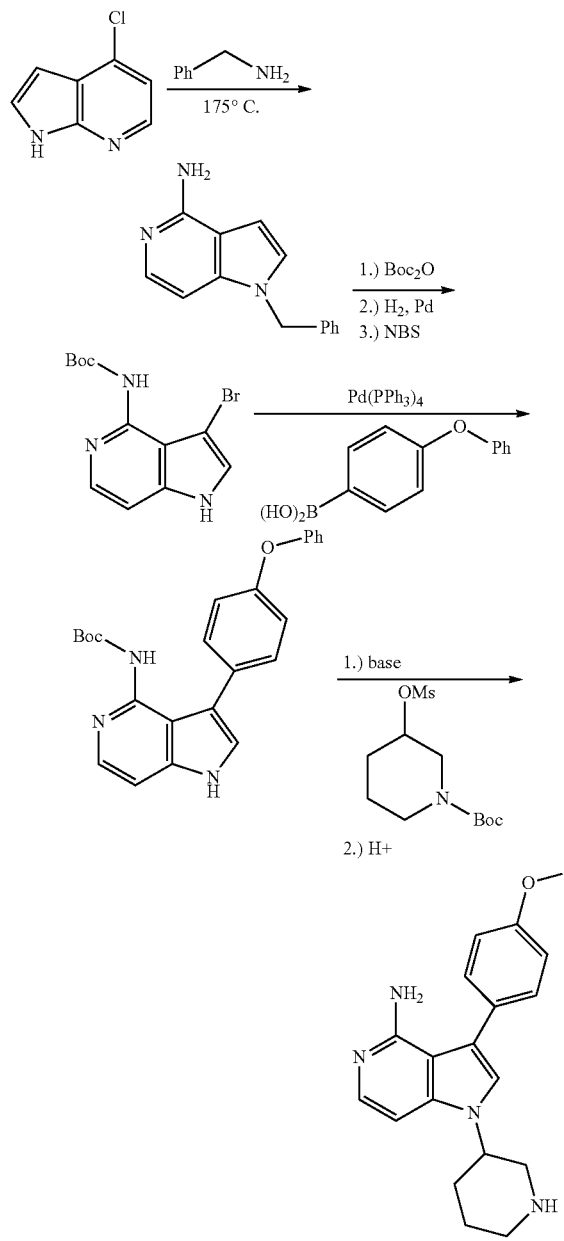

Scheme VI.

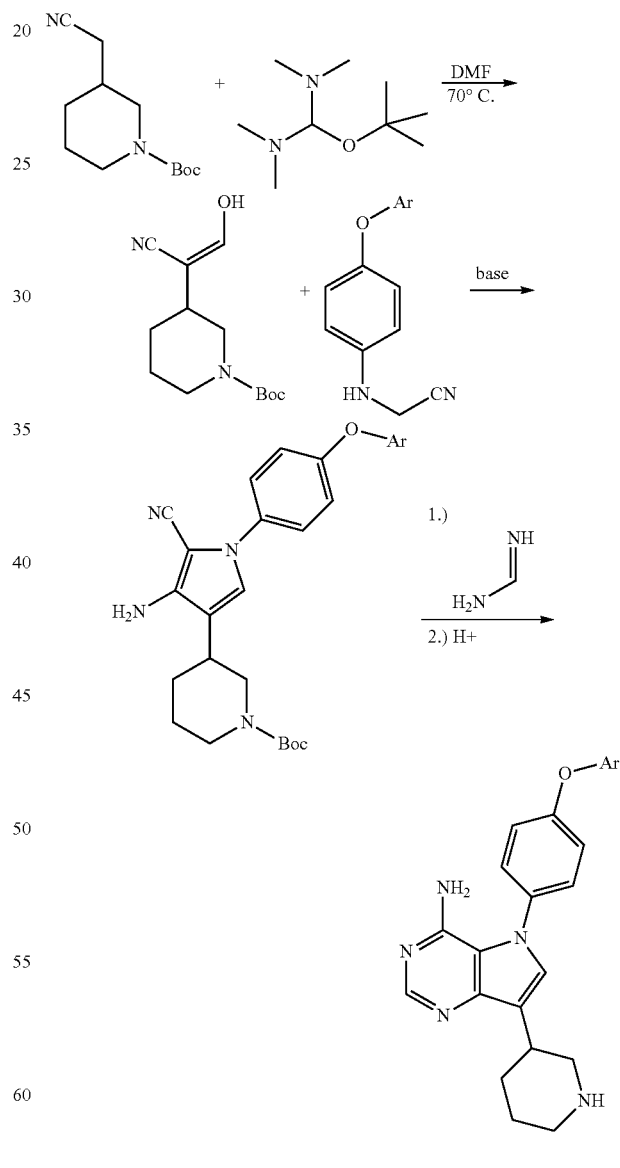

Using the synthetic methods described herein, tyrosine kinase inhibitors as disclosed herein are obtained in good yields and purity. The compounds prepared by the methods disclosed herein are purified by conventional means, such as, for example, filtration, recrystallization, chromatography, distillation, and combinations thereof.

Any combination of the groups described above for the various variables is contemplated herein.

Further Forms of Compounds

Compounds disclosed herein have a structure of any of Formula (A1-A6), Formula (B1-B6), Formula (C1-C6), Formula (D1-D6), Formula (I), or Formula (VII). It is understood that when reference is made to compounds described herein, it is meant to include compounds of any of Formula (A1-A6), Formula (B1-B6), Formula (C1-C6), Formula (D1-D6), Formula (I), or Formula (VII), as well as to all of the specific compounds that fall within the scope of these generic formulae, unless otherwise indicated.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods such as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (A1-A6), Formula (B1-B6), Formula (C1-C6), Formula (D1-D6), Formula (I), or Formula (VII) in unoxidized form can be prepared from N-oxides of compounds of any of Formula (A1-A6), Formula (B1-B6), Formula (C1-C6), Formula (D1-D6), Formula (I), or Formula (VII) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is known, prodrugs of compounds can be designed (if desired) (for examples of this procedure applied to other compounds, see, e.g., Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the compounds herein-described are prodrugs for another derivative or active compound.

Prodrugs are often useful because, in some situations, they are easier to administer than the parent drug. They are, for instance, bioavailable by oral administration whereas the parent is not. The prodrug optionally has improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated by reference for such disclosure.

Sites on the aromatic ring portion of compounds of any of Formula (A1-A6), Formula (B1-B6), Formula (C1-C6), Formula (D1-D6), Formula (I), or Formula (VII) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein (for example, compounds of any of Formula (A1-A6), Formula (B1-B6), Formula (C1-C6), Formula (D1-D6), Formula (I), or Formula (VII)) are optionally in the form of, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts are optionally analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Cysteine-Targeted Kinase Inhibitor Discovery Platform
Kinases/Inhibitors SAR Approach Protein kinases, which act on and modify the activity of specific proteins, are used to transmit signals and control complex processes in cells. Up to 518 different kinases have been identified in humans. Many kinase inhibitor compounds non-selectively bind and/or inhibit these kinases because the active sites of some of these kinases are similar in structure. Such cross-reactivity is not a desired feature of a kinase inhibitor compound because of the potential for undesired side effects when such a compound is being administered to treat a disorder.

We have observed that small differences in the structure of kinase inhibitor compounds have profound effects in the selectivity of similarly-structured kinases (e.g., ACKs, including, Btk and the Btk kinase cysteine homologs).

As a result, we have developed assays, methods, and systems for converting a non-selective inhibitor compound into a highly-selective inhibitor compound. In brief, the non-selective inhibitor compound is provided with a Michael acceptor moiety and a linker moiety that links the Michael acceptor moiety to the remainder of the non-selective inhibitor compound. A series of linker and Michael acceptor moieties provides a small library/panel of test inhibitor compounds. The inhibitor library/panel is contacted with a panel of structurally related kinases (e.g., Btk and the Btk kinase cysteine homologs). Binding is determined by a variety of means, included fluorescence detection (or via any other detectable label), mass spectrometry, or a combination of approaches. An Activity Probe is optionally used to detect binding of members of the inhibitor library/panel to the kinase library/panel. The binding data is then optionally collected and analyzed to provide a structure-activity relationship (SAR) between the structure of the members of the inhibitor panel/library (e.g., Michael acceptor and/or linker moieties) and the activity of binding to and/or inhibiting members of the kinase panel. Based on this information, further modifications are suggested if necessary. We have successfully used this approach to improve the binding and selectivity of Btk inhibitor compounds (see Examples herein, including "Kinase Inhibitor Discovery Platform" example section).

In some embodiments, a similar approach is used for converting a selective inhibitor compound for a group of similarly-structured ACKs (including, Btk and the Btk kinase cysteine homologs) into a more highly-selective inhibitor compound (e.g., more selective for a particular ACK over structurally-similar ACKs), or for converting a selective inhibitor compound for a particular ACK (e.g., Btk) into an even more selective inhibitor of that particular ACK. For example, in brief, the selective inhibitor compound (which, for example, contains an active-site binding moiety, a linker moiety and a Michael acceptor moiety) is modified. In one embodiment, a series of linker and Michael acceptor moieties provides a small library/panel of test inhibitor compounds. The inhibitor library/panel is contacted with a panel of structurally related kinases (e.g., Btk and the Btk kinase cysteine homologs). Binding is determined by a variety of means, included fluorescence detection (or via any other detectable label), mass spectrometry, or a combination of approaches. An Activity Probe is optionally used to detect binding of members of the inhibitor library/panel to the kinase library/panel. The binding data is then optionally collected and analyzed to provide a structure-activity relationship (SAR) between the structure of the members of the inhibitor panel/library (e.g., Michael acceptor and/or linker moieties) and the activity of binding to and/or inhibiting members of the kinase panel. Based on this information, further modifications are suggested if necessary. We have also successfully used this approach to improve the binding and selectivity of Btk inhibitor compounds (see Examples herein, including "Kinase Inhibitor Discovery Platform" example section).

Thus, for our highly selective BTK inhibitor Compound 1, we engineered an electrophilic center capable of irreversibly inactivating the target enzyme, BTK. That is, to an active site binding moiety of a reversible inhibitor was added a linker moiety and a Michael acceptor moiety that achieved a high degree of potency and selectivity by (1) fitting the core scaffold into the active site ATP binding pocket of kinase enzymes, and (2) forming a covalent bond with Cysteine-481 located in BTK. The chemistry required for covalent bond formation involves an electrophilic moiety that acts as a Michael acceptor, which bonds with a nucleophile (such as Cys-481) present in a precise location within the active site.

In another example, the linker and Michael acceptor moiety of Compound 1 was modified to provide Compound 9 which has a different selectivity pattern. Table 1 is a table showing the degree of inhibition of a panel of kinases for two example compounds. $IC_{50}$s were determined using the in vitro HotSpot kinase assay (purified enzymes, 33P-ATP, an appropriate substrate and 1 uM ATP.) Compared to Compound 1, Compound 9 has similar potency toward Btk, but significantly less potency toward JAK-3, ITK, and EGFR and significantly more potency toward the src-family kinases lck, c-src, FGR, Fyn, Hck, and Lyn and Yes. Thus, subtle modifications in the linker moiety and the Michael acceptor moiety are important for the design of selective ACK inhibitors.

TABLE 1

| Kinase | Compound 1 IC50 (nM) | Compound 9 IC50 (nM) |
| --- | --- | --- |
| BTK | 0.5 | 1.0 |
| ITK | 11.7 | 909.9 |
| Bmx/ETK | 0.8 | 1.1 |
| TEC | 77.8 | 108.0 |
| EFGR | 0.5 | 20.6 |
| HER4 | 9.4 | 1536.0 |
| HER4 | 0.1 | 3.2 |
| LCK | 2.0 | 1.0 |
| BLK | 0.5 | 0.2 |
| C-src | 262.6 | 14.3 |
| FGR | 2.3 | 0.4 |
| Fyn | 95.6 | 7.1 |
| HCK | 3.7 | 1.0 |
| Lyn | 16.2 | 1.2 |
| YES | 6.5 | 0.8 |
| ABL | 86.1 | 32.3 |
| Brk | 3.3 | 3.3 |
| CSK | 2.2 | 2.4 |
| FER | 8,070.0 | 3,346.0 |
| JAK3 | 10.4 | 8,278.0 |
| SYK | >10,000 | >10,000 |

Table 2 of Example 1c in the "Kinase Discovery Platform and Pulse Dosing" section of the examples section provides further modifications of the linker moiety and/or the Michael acceptor moiety and the impact of such changes of inhibitor selectivity.

Thus, in one aspect described herein are methods of identifying an irreversible inhibitor of a kinase selected from Btk, a Btk homolog, a Btk kinase cysteine homolog, an ACK, or HER4 (or indeed, any ACK) comprising:

(1) contacting a multiplicity of kinases selected from Btk, a Btk homolog, a Btk kinase cysteine homolog, an ACK, or HER4 (or indeed any ACK) with a compound that comprises a Michael acceptor moiety;
(2) contacting at least one non-kinase molecule having at least one accessible SH group with the compound that comprises a Michael acceptor moiety (this step allows for the selection of inhibitors that have low selectivity for higher abundance biological molecules that have moieties that irreversibly react with the inhibitor; thus preventing the inhibitor from binding to the desire ACK when administered as a drug to an individual); and
(3) determining the covalent binding of the compound that comprises a Michael acceptor with the multiplicity of kinases and the at least one non-kinase molecule; and repeating steps (1), (2), and (3) for at least one other compound that comprises a Michael acceptor moiety.

In a further aspect, the following steps are added: (4) comparing the covalent binding of the compound that comprises a Michael acceptor with the multiplicity of kinases and the at least one non-kinase molecule; and repeating steps (1), (2), (3) and (4) for at least one other compound that comprises a Michael acceptor moiety.

In a further aspect the irreversible inhibitor compounds are also contacted with at least one non-ACK kinase in order to determine the selectivity of the irreversible inhibitor compound for the ACK relative to the non-ACK.

By way of certain relevant examples of non-kinase molecules with at least one accessible SH group are glutathione and/or hemoglobin. Because of the high abundance of these molecules in typical biological systems (e.g., in an individual), the desired irreversible inhibitor compounds have low selectivity/reactivity with these non-kinase molecules.

In certain embodiments of the Kinase Inhibitor Discovery Platform, an Activity Probe (described in more detail herein) is used as a rapid diagnostic method for determining whether a test inhibitor compound has irreversibly inhibited an ACK. In one embodiment, the Activity Probe is itself an irreversible inhibitor of an ACK, an irreversible inhibitor of HER4, and further, has a reporter moiety (e.g., a fluorescent moiety) as part of its structure. When used in competition with a test irreversible inhibitor, the absence of a 'reporter' signal on an ACK is one indication that the test irreversible inhibitor has prevented the Activity Probe from binding to the ACK (and that the test irreversible inhibitor has a higher binding affinity for the ACK than the Activity Probe).

In certain embodiments, the Kinase Inhibitor Discovery Platform, steps (1) and (2) are conducted in vivo and step (3) is conducted in part using an Activity Probe. Further, in certain embodiments, the determining step uses mass spectrometry, fluorescence, or a combination thereof.

As described herein, in one embodiment, the inhibitor tested with the Kinase Inhibitor Discovery Platform comprise an active site binding moiety, a Michael acceptor moiety, and a linker moiety that links the Michael acceptor moiety to the active site binding moiety. For example, in such a scheme, the following information is collected and analyzed: the structure-function activity relationship between the structure of the linker moiety and/or the Michael acceptor moiety of each compound, and the binding and/or selectivity of each compound to at least one kinase. Further, in certain embodiments, structure of the active site binding moiety of each compound is not varied, whereas the structure of the linker moiety and/or the Michael acceptor moiety is varied.

In one example, the inhibitors have the structure of Formula (VII):

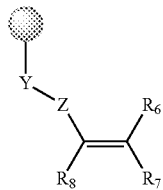

Formula (VII)

wherein:
wherein

is a moiety that binds to the active site of a kinase, including a tyrosine kinase, further including a Btk kinase cysteine homolog;

Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene;

Z is $C(=O)$, $OC(=O)$, $NHC(=O)$, $NCH_3C(=O)$, $C(=S)$, $S(=O)_x$, $OS(=O)_x$, $NHS(=O)_x$, where x is 1 or 2;

$R_7$ and $R_8$ are independently selected from among H, unsubstituted $C_1$-$C_4$ alkyl, substituted $C_1$-$C_4$ alkyl, unsubstituted $C_1$-$C_4$ heteroalkyl, substituted $C_1$-$C_4$ heteroalkyl, unsubstituted $C_3$-$C_6$ cycloalkyl, substituted $C_3$-$C_6$ cycloalkyl, unsubstituted $C_2$-$C_6$ heterocycloalkyl, and substituted $C_2$-$C_6$ heterocycloalkyl; or $R_7$ and $R_8$ taken together form a bond; and $R_6$ is H, substituted or unsubstituted $C_1$-$C_4$ alkyl, substituted or unsubstituted $C_1$-$C_4$ heteroalkyl, $C_1$-$C_6$ alkoxyalkyl, $C_1$-$C_8$ alkylaminoalkyl, $C_1$-$C_8$ hydroxyalkylaminoalkyl, $C_1$-$C_8$ alkoxyalkylaminoalkyl, substituted or unsubstituted $C_3$-$C_6$ cycloalkyl, substituted or unsubstituted aryl, substituted or unsubstituted $C_2$-$C_8$ heterocycloalkyl, substituted or unsubstituted heteroaryl, $C_1$-$C_4$ alkyl(aryl), $C_1$-$C_4$ alkyl(heteroaryl), $C_1$-$C_4$ alkyl($C_3$-$C_8$ cycloalkyl), or $C_1$-$C_4$ alkyl($C_2$-$C_8$ heterocycloalkyl).

In such a scheme, the following information is collected and analyzed: the structure-function activity relationship between the structure of Y—Z and/or

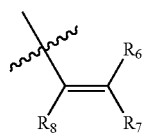

of each compound, and the binding and/or selectivity of each compound to at least one kinase. Further, the structure of

of each compound is not varied, whereas the structure of the linker moiety (Y—Z) and/or the Michael acceptor moiety

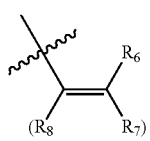

is varied.

In certain embodiments of the Kinase Inhibitor Discovery Platform, the resulting inhibitor is selective for one kinase selected from Btk, a Btk homolog, an ACK, HER4, and a Btk kinase cysteine homolog over at least one other kinase selected from Btk, a Btk homolog, an ACK, HER4, and a Btk kinase cysteine homolog. In some embodiments, this selectivity is at least 5×, at least 10×, at least 20×, at least 50×, or at least 100×. In further embodiments, the resulting inhibitor is selective for at least one kinase selected from Btk, a Btk homolog, an ACK, HER4, and a Btk kinase cysteine homolog over at least one other non-kinase molecule having an accessible SH group. In some embodiments, this selectivity is at least 5×, at least 10×, at least 20×, at least 50×, or at least 100×.

In further embodiments, the resulting inhibitor is used in the therapeutic methods described herein, or in the pharmaceutical compositions described herein.

Activity Probe Compounds

Because of the Kinase Inhibitor Discovery Platform described herein optionally utilizes an Activity Probe, the following section describes the design, structure and use of non-limiting examples of Activity Probes.

The Activity Probe compounds described herein are composed of a moiety comprising an inhibitor of Btk, a Btk homolog, a Btk kinase cysteine homolog, an ACK, or HER4 (hereinafter, a "Kinase Inhibitor"), a linker moiety, and a reporter moiety. In one embodiment, the Kinase Inhibitor is an irreversible inhibitor. In another embodiment, the irreversible Kinase Inhibitor binds to a non-catalytic residue in the ATP binding pocket of Btk, a Btk homolog, a Btk kinase cysteine homolog, an ACK, or HER4 (hereinafter a "Kinase"); in further embodiments, the non-catalytic residue is a cysteine residue. In some embodiments, the Activity Probe forms a covalent bond with at least one non-catalytic residue of a Kinase. In other embodiments, the Activity Probe forms a non-covalent bond with at least one non-catalytic residue of a Kinase. In a further embodiment, the Activity Probe forms hydrogen bonding within the ATP binding pocket of a Kinase. In yet a further embodiment, the Activity Probe has Van der Waals attractions with the Kinase.

In some other embodiments, the Activity Probes described herein are activity dependent such that the probe binds only an active Kinase. In further embodiments, the Activity Probe binds a Kinase that has been switched on by phosphorylation by upstream kinases. In yet a further embodiment, the Activity Probes described herein are activity independent such that the probe binds Kinases that have not been switched on by phosphorylation by upstream kinases. In some embodiments, the Activity Probe labels a phosphorylated conformation of a Kinase. In other embodiments, the Activity Probe labels a Kinase in a non-phosphorylated conformation.

In some embodiments, the Activity Probe is permeable to cells.

In further embodiments, the linker moiety is selected from a bond, a substituted alkyl moiety, a substituted heterocycle moiety, a substituted amide moiety, a ketone moiety, a substituted carbamate moiety, an ester moiety, or any combination thereof. In further embodiments, the reporter moiety is a moiety that is detected using standard or modified laboratory equipment.

In one aspect is a Activity Probe of Formula (I) comprising:

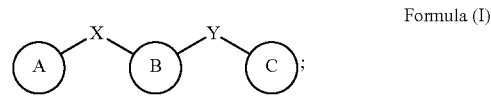

Formula (I)

wherein:

A is a Kinase Inhibitor moiety;

X and Y are independently selected from the group consisting of: a bond, —O(C=O)—, —NR$^a$(C=O)—, —NR$^a$—,

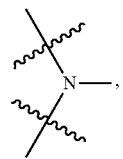 [SMILES: *N(*)C]

—O—, —S—, —S—S—, —O—NR$^a$—, —O(C=O)O—, —O(C=O)NR$^a$, —NR$^a$(C=O)NR$^a$—, —N=CR$^a$—, —S(C=O)—, —S(O)—, and —S(O)$_2$—;

wherein

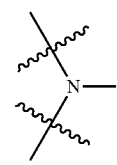 [SMILES: *N(*)C]

forms a N-containing heterocycle;

B is a linker moiety;

C is a reporter moiety; and

R$^a$ is hydrogen or alkyl.

In one embodiment, the moiety comprising an irreversible Kinase Inhibitor is derived from an irreversible inhibitor of a Kinase. In some embodiments, such irreversible Kinase Inhibitors should possess at least one of the following characteristics: potency, selectively and cell permeability. In further embodiments, such irreversible Kinase Inhibitors possess at least two of the aforementioned characteristics, and in further embodiments, at least all of the aforementioned characteristics.

In another embodiment, the Kinase Inhibitor moiety is derived from a Btk inhibitor having the structure of Formula (II):

Formula (II)

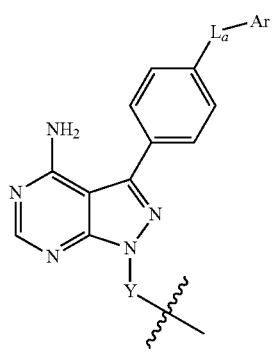

wherein:

$L_a$ is $CH_2$, O, NH or S;

Ar is a substituted or unsubstituted aryl, or a substituted or unsubstituted heteroaryl; and Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene.

In some embodiments, $L_a$ is $CH_2$, O, or NH. In other embodiments, $L_a$ is O or NH. In yet other embodiments, $L_a$ is O.

In other embodiments, Ar is a substituted or unsubstituted aryl. In yet other embodiments, Ar is a 6-membered aryl. In some other embodiments, Ar is phenyl.

In some embodiments, Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene. In other embodiments, Y is an optionally substituted group selected from among $C_1$-$C_6$alkylene, $C_1$-$C_6$heteroalkylene, 4-, 5-, 6-, or 7-membered cycloalkylene, and 4-, 5-, 6-, or 7-membered heterocycloalkylene. In yet other embodiments, Y is an optionally substituted group selected from among $C_1$-$C_6$alkylene, $C_1$-$C_6$heteroalkylene 5- or 6-membered cycloalkylene, and 5- or 6-membered heterocycloalkylene containing 1 or 2 N atoms. In some other embodiments, Y is a 5- or 6-membered cycloalkylene, or a 5- or 6-membered heterocycloalkylene containing 1 or 2 N atoms. In some embodiments, Y is a 4-, 5-, 6-, or 7-membered cycloalkylene ring; or Y is a 4-, 5-, 6-, or 7-membered heterocycloalkylene ring.

In some embodiments, the Kinase Inhibitor moiety is derived from a compound selected from among: 1-(3-(4-amino-3-(4-phenoxyphenyl)-1H-pyrazolo[3,4-d]pyrimidin-1-yl)piperidin-1-yl)prop-2-en-1-one; (E)-1-(3-(4-amino-3-(4-phenoxyphenyl)-1H-pyrazolo[3,4-d]pyrimidin-1-yl)piperidin-1-yl)but-2-en-1-one; 1-(3-(4-amino-3-(4-phenoxyphenyl)-1H-pyrazolo[3,4-d]pyrimidin-1-yl)piperidin-1-yl)sulfonylethene; 1-(3-(4-amino-3-(4-phenoxyphenyl)-1H-pyrazolo[3,4-d]pyrimidin-1-yl)piperidin-1-yl)prop-2-yn-1-one; 1-(4-(4-amino-3-(4-phenoxyphenyl)-1H-pyrazolo[3,4-d]pyrimidin-1-yl)piperidin-1-yl)prop-2-en-1-one; N-((1s,4s)-4-(4-amino-3-(4-phenoxyphenyl)-1H-pyrazolo[3,4-d]pyrimidin-1-yl)cyclohexyl)acrylamide; 1-((R)-3-(4-amino-3-(4-phenoxyphenyl)-1H-pyrazolo[3,4-d]pyrimidin-1-yl)pyrrolidin-1-yl)prop-2-en-1-one; 1-((S)-3-(4-amino-3-(4-phenoxyphenyl)-1H-pyrazolo[3,4-d]pyrimidin-1-yl)pyrrolidin-1-yl)prop-2-en-1-one; 1-((R)-3-(4-amino-3-(4-phenoxyphenyl)-1H-pyrazolo[3,4-d]pyrimidin-1-yl)piperidin-1-yl)prop-2-en-1-one; 1-((S)-3-(4-amino-3-(4-phenoxyphenyl)-1H-pyrazolo[3,4-d]pyrimidin-1-yl)piperidin-1-yl) prop-2-en-1-one; and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one; (E)-4-(N-(2-hydroxyethyl)-N-methylamino)-1-(3-(4-phenoxyphenyl)-1H-pyrazolo[3,4-d]pyrimidin-1-yl) piperidin-1-yl)but-2-en-1-one (Compound 3); (E)-1-(3-(4-amino-3-(4-phenoxyphenyl)-1H-pyrazolo[3,4-d]pyrimidin-1-yl)-3-(1H-imidazol-4-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)-4-morpholinobut-2-en-1-one (Compound 5); (E)-1-(4-(4-amino-3-(4-phenoxyphenyl)-1H-pyrazolo[3,4-d]pyrimidin-1-yl)piperidin-1-yl)-4-(dimethylamino)but-2-en-1-one (Compound 7); (E)-N-((1s,4s)-4-(4-amino-3-(4-phenoxyphenyl)-1H-pyrazolo[3,4-d] pyrimidin-1-yl)cyclohexyl)-4-(dimethylamino)but-2-enamide (Compound 8); N-((1r,4r)-4-(4-amino-3-(4-phenoxyphenyl)-1H-pyrazolo[3,4-d]pyrimidin-1-yl) cyclohexyl)acrylamide (Compound 10); (E)-1-((R)-2-((4-amino-3-(4-phenoxyphenyl)-1H-pyrazolo[3,4-d]pyrimidin-1-yl)methyl)pyrrolidin-1-yl)-4-(dimethylamino)but-2-en-1-one (Compound 11); (E)-1-((S)-2-((4-amino-3-(4-phenoxyphenyl)-1H-pyrazolo[3,4-d]pyrimidin-1-yl)methyl) pyrrolidin-1-yl)-4-(dimethylamino)but-2-en-1-one (Compound 12); 1-((R)-2-((4-amino-3-(4-phenoxyphenyl)-1H-pyrazolo[3,4-d]pyrimidin-1-yl)methyl)pyrrolidin-1-yl) prop-2-en-1-one (Compound 13); 1-((S)-2-((4-amino-3-(4-phenoxyphenyl)-1H-pyrazolo[3,4-d]pyrimidin-1-yl)methyl) pyrrolidin-1-yl)prop-2-en-1-one (Compound 14); 1((R)-2-((4-amino-3-(4-phenoxyphenyl)-1H-pyrazolo[3,4-d] pyrimidin-1-yl)methyl)pyrrolidin-1-yl)but-2-yn-1-one (Compound 15); 1-((S)-2-((4-amino-3-(4-phenoxyphenyl)-1H-pyrazolo[3,4-d]pyrimidin-1-yl)methyl)pyrrolidin-1-yl) but-2-yn-1-one (Compound 16); 1-((R)-3-(4-amino-3-(4-phenoxyphenyl)-1H-pyrazolo[3,4-d]pyrimidin-1-yl) piperidin-1-yl)but-2-yn-1-one (Compound 17); (E)-N-((1r, 4r)-4-(4-amino-3-(4-phenoxyphenyl)-1H-pyrazolo[3,4-d] pyrimidin-1-yl)cyclohexyl-4-(dimethylamino)but-2-enamide (Compound 18); N-(2-(4-amino-3-(4-phenoxyphenyl)-1H-pyrazolo[3,4-d]pyrimidin-1-yl)ethyl)-N-methylacrylamide (Compound 19); (E)-1-(4-(4-amino-3-(4-phenoxyphenyl)-1H-pyrazolo[3,4-d]pyrimidin-1-yl)-4-morpholinobut-2-en-1-one (Compound 20); (E)-1-((S_-2-((4-amino-3-(4-phenoxyphenyl)-1H-pyrazolo[3,4-d] pyrimidin-1-yl)methyl)pyrrolidin-1-yl)-4-morpholinobut-2-en-1-one (Compound 21); N-((1s,4s)-4-(4-amino-3-(4-phenoxyphenyl)-1H-pyrazolo[3,4-d]pyrimidin-1-yl) cyclohexyl)but-2-ynamide (Compound 22); N-(2-(4-amino-3-(4-phenoxyphenyl)-1H-pyrazolo[3,4-d]pyrimidin-1-yl) ethyl)acrylamide (Compound 23); (E)-1-((R)-3-(4-amino-3-(4-phenoxyphenyl)-1H-pyrazolo[3,4-d]pyrimidin-1-yl) piperidin-1-yl)-4-morpholinobut-2-en-1-one (Compound 24); (E)-N-((1s,4s)-4-(4-amino-3-(4-phenoxyphenyl)-1H-pyrazolo[3,4-d]pyrimidin-1-yl)cyclohexyl)-4-morpholinobut-2-enamide (Compound 25).

In another embodiment, the linker moiety is selected from a bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the linker moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the linker moiety is optionally substituted with halogen, CN, OH, $NO_2$, alkyl, S(O), and $S(O)_2$. In other embodiments, the water soluble polymer is a PEG group.

In other embodiments, the linker moiety provides sufficient spatial separation between the reporter moiety and the Kinase Inhibitor moiety. In further embodiments, the linker moiety is stable. In yet a further embodiment, the linker moiety does not substantially affect the response of the reporter moiety. In other embodiments the linker moiety provides chemical stability to the Activity Probe. In further embodiments, the linker moiety provides sufficient solubility to the Activity Probe.

In some embodiments, linkages such as water soluble polymers are coupled at one end to a Kinase Inhibitor moiety and to a reporter moiety at the other end. In other embodiments, the water soluble polymers are coupled via a functional group or substituent of the Kinase Inhibitor moiety. In further embodiments, the water soluble polymers are coupled via a functional group or substituent of the reporter moiety. In other embodiments, covalent attachment of hydrophilic polymers to a Kinase Inhibitor moiety and a reporter moiety represents one approach to increasing water solubility (such as in a physiological environment), bioavailability, increasing serum half-life, increasing pharmacodynamic parameters, or extending the circulation time of the Activity Probe, including proteins, peptides, and particularly hydrophobic molecules. In further embodiments, additional important features of such hydrophilic polymers include biocompatibility and lack of toxicity. In other embodiments, for therapeutic use of the end-product preparation, the polymer is pharmaceutically acceptable.

In some embodiments, examples of hydrophilic polymers include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyamino-acids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing. In other embodiments, the water soluble polymer is any structural form including but not limited to linear, forked or branched. In some embodiments, polymer backbones that are water-soluble, with from 2 to about 300 termini, are particularly useful. In further embodiments, multifunctional polymer derivatives include, but are not limited to, linear polymers having two termini, each terminus being bonded to a functional group which is the same or different. In some embodiments, the water polymer comprises a poly(ethylene glycol) moiety. In further embodiments, the molecular weight of the polymer is of a wide range, including but not limited to, between about 100 Da and about 100,000 Da or more. In yet further embodiments, the molecular weight of the polymer is between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. The foregoing list for substantially water soluble backbones is by no means exhaustive and is merely illustrative, and in some embodiments, the polymeric materials having the qualities described above suitable for use in methods and compositions described herein.

In further embodiments, the number of water soluble polymers linked to a Kinase Inhibitor moiety and a reporter moiety described herein is adjusted to provide an altered (including but not limited to, increased or decreased) pharmacologic, pharmacokinetic or pharmacodynamic characteristic such as in vivo half-life. In some embodiments, the half-life of the Activity Probe is increased at least about 10, about 20, about 30, about 40, about 50, about 60, about 70, about 80, about 90 percent, about two fold, about five-fold, about 10-fold, about 50-fold, or at least about 100-fold over a Activity Probe without a water soluble linker.

In another embodiment, X is selected from the group consisting of: a bond, —O(C=O)—, —NR$^a$(C=O)—, —NR$^a$—,

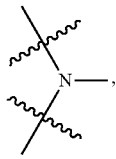

—O—, —S—, —S—S—, —O—NR$^a$—, —O(C=O)O—, —O(C=O)NR$^a$, —NR$^a$(C=O)NR$^a$—, —N=CR$^a$—, —S(C=O)—, —S(O)—, and —S(O)$_2$—; wherein

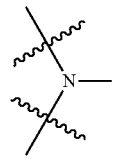

forms a N-containing heterocycle. In one embodiment, X is NR$^a$(C=O). In another embodiment, X is a bond. In another embodiment, X is —O(C=O)—. In a further embodiment, Y is selected from the group consisting of: a bond, —O(C=O)—, —NR$^a$(C=O)—, —NR$^a$—,

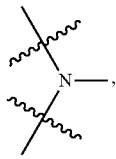

—O—, —S—, —S—S—, —O—NR$^a$—, —O(C=O)O—, —O(C=O)NR$^a$, —NR$^a$(C=O)NR$^a$—, —N=CR$^a$—, —S(C=O)—, —S(O)—, and —S(O)$_2$—; wherein

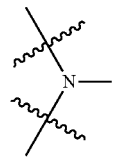 [SMILES: *N(*)C]

forms a N-containing heterocycle. In yet a further embodiment, Y is a bond. In one embodiment, Y is —NR$^a$(C=O)—. In yet another embodiment, R$^a$ is hydrogen. In yet a further embodiment, R$^a$ is alkyl.

In a further embodiment, the reporter moiety is selected from the group consisting of a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analog, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In another embodiment, the reporter moiety is a fluorophore. In a further embodiment, the fluorophore is selected from the group consisting of: BODIPY 493/503, BODIPY FL, BODIPY R6G, BODIPY 530/550, BODIPY TMR, BODIPY 558/568, BODIPY 564/570, BODIPY 576/589, BODIPY 581/591, BODIPY TR, Fluorescein, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1, 5-FAM, BCECF, BCECF, dichlorofluorescein, rhodamine 110, rhodamine 123, Rhodamine Green, YO-PRO-1, SYTOX Green, Sodium Green, SYBR Green I, Alexa Fluor 500, FITC, Fluo-3, Fluo-4, fluoroemerald, YoYo-1 ssDNA, YoYo-1 dsDNA, YoYo-1, SYTO RNASelect, Diversa Green-FP, Dragon Green, EvaGreen, Surf Green EX, Spectrum Green, Oregon Green 488, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, EGFP (Campbell Tsien 2003), EGFP (Patterson 2001), Fluorescein, Kaede Green, 7-Benzylamino-4-Nitrobenz-2-Oxa-1,3-Diazole, Bexl, Doxorubicin, Lumio Green, and SuperGlo GFP.

In a further embodiment, the fluorophore is selected from the group consisting of: BODIPY 493/503, BODIPY FL, BODIPY R6G, BODIPY 530/550, BODIPY TMR, BODIPY 558/568, BODIPY 564/570, BODIPY 576/589, BODIPY 581/591, and BODIPY TR. In yet a further embodiment, the fluorophore is BODIPY FL. In certain embodiments, the fluorophore is not BODIPY 530. In some embodiments, the fluorophore has an excitation maxima of between about 500 and about 600 nm. In some other embodiments, the fluorophore has an excitation maxima of between about 500 and about 550 nm. In another embodiments, the fluorophore has an excitation maxima of between about 550 and about 600 nm. In yet a further embodiment, the fluorophore has an excitation maxima of between about 525 and about 575 nm. In other embodiments, the fluorophore has an emission maxima of between about 510 and about 670 nm. In another embodiment, the fluorophore has an emission maxima of between about 510 and about 600 nm. In a further embodiment, the fluorophore has an emission maxima of between about 600 and about 670 nm. In another embodiment, the fluorophore has an emission maxima of between about 575 and about 625 nm.

By way of example only and in some embodiments, the observed potency, selectivity, and cell permeability of compounds such as Compound 2 are appropriate to incorporate these molecules into a Kinase-targeted, activity based probe that allows direct visualization of Kinase activity in intact cells. In vitro profiling against a panel of greater than 100 kinases showed Compound 2 to be a highly potent and selective inhibitor of Tec family kinases, including, Btk, as well as Src family kinases. Without limiting the scope of the compositions and methods described herein, it is postulated that the structural basis for the selectivity is covalent modification of a non-catalytic cysteine residue (Cys 481 in Btk) that is conserved in the ATP binding pocket of the Tec family and several other kinases.

However, in other embodiments, any irreversible Kinase Inhibitor that binds to the non-catalytic cysteine residue in the ATP binding pocket of a Kinase is used in the compounds and methods described herein.

General Synthesis and Characterization of an Illustrative Activity Probe

Without limiting the scope of the compositions described herein, an illustrative probe was synthesized by attaching a bodipy FL fluorophore to an irreversible inhibitor via a piperazine linker. The piperazine linker served to maintain probe solubility and provided spatial separation between the fluorophore and the pyrazolopyrimidine core.

thioether functionalities, and optionally aromatic or mono/polyunsaturated hydrocarbons, polyoxyethylene such as polyethylene glycol, oligo/polyamides such as poly-.α.-alanine, polyglycine, polylysine, and peptides in general, oligosaccharides, oligo/polyphosphates. Moreover, in other embodiments, the spacer consists of combined units thereof. In further embodiments, the length of the spacer varies, taking into consideration the desired or necessary positioning and spatial orientation of the active/functional part of the Activity Probe.

Without limiting the scope of the compositions described herein, in some embodiments the reporter moiety is Bodipy. In the present context, the term reporter moiety means a group which is detectable either by itself or as a part of a detection series.

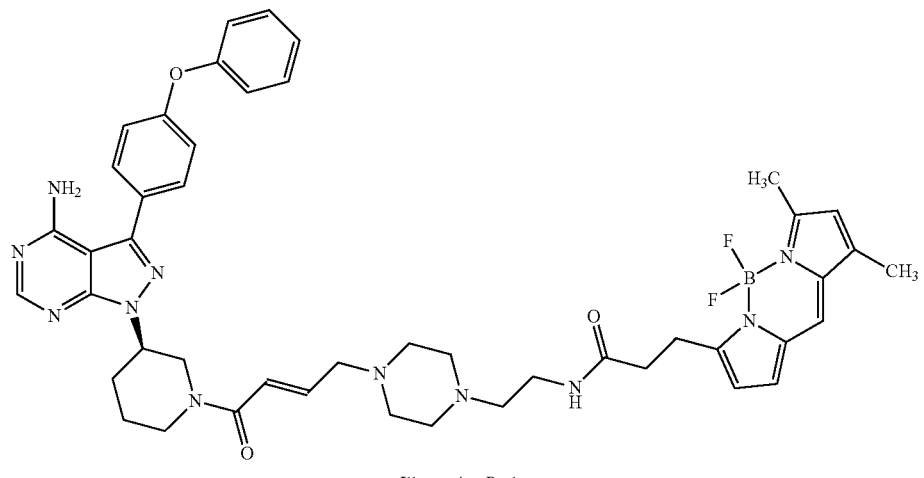

Illustrative Probe

In some embodiments, the linkage formed is a stable linkage. In other embodiments, in the case where the conjugate comprises two components, the linker moiety forms a linkage, in some embodiments, a stable linkage, between the Kinase Inhibitor moiety and the reporter moiety. In some embodiments, the linker moiety is stable and provides the means to control and determine the distance between the Kinase Inhibitor moiety and the report moiety. Further, in some embodiments, the linker moiety is selected such that the probe's solubility is maintained. In some embodiments, the linker moiety is a piperazinyl moiety. In further embodiments, a piperazinyl-based linkage is formed by using a piperazine containing compound. In other embodiments, the number and order of units that comprise the linker moiety is selected such that the length between the first component and the second component, as well as the hydrophobic and hydrophilic characteristics of the linker is controlled.

In the present context, spatial separation means a thermochemically and photochemically non-active distance-making group and in some embodiments is used to join two or more different moieties of the types defined above. In other embodiments, spacers are selected on the basis of a variety of characteristics including their hydrophobicity, hydrophilicity, molecular flexibility and length. The spacer, thus, in some embodiments, comprises a chain of carbon atoms optionally interrupted or terminated with one or more heteroatoms, such as oxygen atoms, nitrogen atoms, and/or sulphur atoms. Thus, in some embodiments, the spacer comprises one or more amide, ester, amino, ether, and/or In some embodiments, the labeled Activity Probes described herein are purified by one or more procedures including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. In other embodiments, apparent molecular weight is estimated by GPC by comparison to globular protein standards (PROTEIN PURIFICATION METHODS, A PRACTICAL APPROACH (Harris & Angal, Eds.) IRL Press 1989, 293-306).

In one aspect, the in vitro inhibitory potency of a probe against a panel of selected Kinases as a rapid means of confirming accessibility of the reactive moiety to the Kinase active site is tested. By way of example only, although less potent than the parent Compound 2, the illustrative probe of Compound 3 retains potency against Btk ($IC_{50}$~90 nM). Thus, the piperazine linker and bodipy fluorophore do not seriously compromise accessibility of the illustrative probe to the enzyme active site.

The Activity Probes described herein label kinases at the non-catalytic Cys 481 (or a homologous cysteine) and that in some embodiments, probe labeling does not require the catalytic machinery per se. As such it differs from canonical activity-based probes that target the enzyme catalytic machinery directly. In some embodiments, the Kinase undergoes a phosphorylation dependent conformational change that is tightly coupled to ATP binding and kinase activation. In some embodiments, effective labeling by a probe requires the Kinase to be in its active conformation in order to directly detect Kinase activity in cells. In other embodiments, effective labeling by an Activity Probe does not require the Kinase to be in its active conformation in order to directly detect Kinase activity in cells.

Therapeutic Uses of Irreversible Inhibitor Compounds

Described herein are methods, compositions, uses and medicaments for the treatment of disorders characterized by the presence of a solid tumor comprising administering to an individual in need an irreversible inhibitor of an ACK. In some embodiments, the disorder is a sarcoma, lymphoma, and/or carcinoma. In some embodiments, the disorder is mammary ductal carcinoma, lobular carcinoma, an adenocarcinoma (e.g. pancreatic cancer and colon cancer), small cell lung carcinoma, non-small cell lung carcinoma, and melanomas. In some embodiments, the disorder is mammary ductal carcinoma, lobular carcinoma, or a combination thereof. In some embodiments, the disorder is pancreatic cancer.

In some embodiments, the ACK is Btk or a Btk homolog. In yet further embodiments, the ACK is tyrosine kinases that share homology with Btk by having a cysteine residue (including a Cys 481 residue) that forms a covalent bond with the irreversible inhibitor. See, e.g., protein kinases in FIG. 7. In some embodiments, the ACK is HER4.

The methods described herein (which includes uses of a pharmaceutical composition to treat a disorder, or uses of a compound to form a medicament for treating a disorder) include administering to an individual in need thereof a composition containing a therapeutically effective amount of one or more irreversible Btk inhibitor compounds described herein. In some embodiments, the individual has been diagnosed with or is predisposed to develop a sarcoma, lymphoma, and/or carcinoma. In some embodiments, the individual has been diagnosed with or is predisposed to develop mammary ductal carcinoma, lobular carcinoma, an adenocarcinoma (e.g. pancreatic cancer and colon cancer), small cell lung carcinoma, non-small cell lung carcinoma, and melanomas. In some embodiments, the individual has been diagnosed with or is predisposed to develop mammary ductal carcinoma, lobular carcinoma, or a combination thereof. In some embodiments, the individual has been diagnosed with or is predisposed to develop pancreatic cancer.

Without being bound by theory, the diverse roles played by Btk signaling in various hematopoietic cell functions show that small molecule Btk inhibitors are useful for reducing the risk of or treating a disorder characterized by the presence or development of one or more solid tumors.

In some embodiments, are methods for treating a disorder characterized by the presence of a solid tumor (e.g. lymphomas, carcinomas, and/or sarcomas) comprising administering to an individual in need a pharmaceutical formulation of any irreversible inhibitor of Btk (or a Btk homolog) of Formula (A1-A6), Formula (B1-B6), Formula (C1-C6), Formula (D1-D6), Formula (I), or Formula (VII). In some embodiments, the solid neoplasm is mammary ductal carcinoma, lobular carcinoma, an adenocarcinoma (e.g. pancreatic cancer and colon cancer), small cell lung carcinoma, non-small cell lung carcinoma, and melanomas.

In still further embodiments are methods for treating a disorder characterized by the presence of a solid tumor comprising administering to an individual in need thereof a composition containing a therapeutically effective amount of a compound that forms a covalent bond with a cysteine sidechain of a Bruton's tyrosine kinase or a Bruton's tyrosine kinase homolog. In some embodiments, the individual has been diagnosed with or is predisposed to develop a sarcoma, lymphoma, and/or carcinoma. In some embodiments, the individual has been diagnosed with or is predisposed to develop mammary ductal carcinoma, lobular carcinoma, an adenocarcinoma (e.g. pancreatic cancer and colon cancer), small cell lung carcinoma, non-small cell lung carcinoma, and melanomas. In some embodiments, the individual has been diagnosed with or is predisposed to develop mammary ductal carcinoma, lobular carcinoma, or a combination thereof. In some embodiments, the individual has been diagnosed with or is predisposed to develop pancreatic cancer.

Further, in some embodiments, the irreversible Btk inhibitor compounds described herein are used to inhibit a small subset of other tyrosine kinases that share homology with Btk by having a cysteine residue (including a Cys 481 residue) that is able to form a covalent bond with the irreversible inhibitor. See, e.g., protein kinases in FIG. 7. Thus, a subset of tyrosine kinases other than Btk are also expected to be useful as therapeutic targets in a number of health conditions, including lymphomas, carcinomas, and/or sarcomas.

Symptoms, diagnostic tests, and prognostic tests for each of the above-mentioned conditions include, e.g., *Harrison's Principles of Internal Medicine©,*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of irreversible inhibitors, including irreversible Btk inhibitor compounds for treating any of the foregoing diseases. For example, refer to Examples 1-4 of the "Therapeutic Uses" section of the Examples included herein. As an example, dosing of irreversible inhibitors for the treatment of cancer can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866. Animal models for treatment of thromboembolic disorders are also known.

In one embodiment, the therapeutic efficacy of the compound for one of the foregoing diseases is optimized during a course of treatment. For example, an individual being treated optionally undergoes a diagnostic evaluation to correlate the relief of disease symptoms or pathologies to inhibition of in vivo Btk activity achieved by administering a given dose of an irreversible Btk inhibitor. Cellular assays are used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells are used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to an individual is optionally increased or decreased as needed so as to maintain a level of Btk inhibition optimal for treating the subject's disease state.

In one embodiment are methods for identifying biomarkers suitable for determining patient response to an irreversible ACK inhibitor (including, e.g., a compound of Formula (I)) comprising administering to a test subject a composition containing an amount of the irreversible ACK inhibitor (including, e.g., a compound of Formula (I)) sufficient to inhibit B cell receptor signaling and correlating B cell receptor signaling with apoptosis. In another or further embodiment are methods for selecting an individual for treatment for lymphoma with an irreversible ACK inhibitor (including, e.g., a compound of Formula (I)) comprising measuring pErk or Erk transcriptional target levels in an individual sample, and correlating a high level of transcriptional targets with a positive response to the treatment. In another or further embodiments are methods for measuring an individual's response to treatment comprising administering to the patient an irreversible ACK inhibitor (including, e.g., a compound of Formula (I)), measuring pErk or Erk transcriptional target levels in an individual sample, and correlating a reduced level of transcriptional targets with a positive response to the administration of the irreversible ACK inhibitor (including, e.g., a compound of Formula (I)).

Combination Treatments

In some embodiments, the irreversible Btk inhibitor compositions described herein are used in combination with other well known therapeutic reagents that are selected for their therapeutic value for the condition to be treated. In general, the compositions described herein and, in embodiments where combinational therapy is employed, other agents do not have to be administered in the same pharmaceutical composition, and are optionally, because of different physical and chemical characteristics, have to be administered by different routes. The initial administration is made, for example, according to established protocols, and then, based upon the observed effects, the dosage, modes of administration and times of administration are modified.

In certain instances, it is appropriate to administer at least one irreversible Btk inhibitor compound described herein in combination with another therapeutic agent. By way of example only, if one of the side effects experienced by an individual upon receiving one of the irreversible Btk inhibitor compounds described herein is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by an individual is increased by administering one of the compounds described herein with another therapeutic agent (which also includes a therapeutic regimen) that also has therapeutic benefit. In any case, regardless of the disease, disorder being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disorder, the condition of the patient, and the actual choice of compounds used. The determination of the order of administration, and the number of repetitions of administration of each therapeutic agent during a treatment protocol, is based on an evaluation of the disease being treated and the condition of the patient.

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disorder being treated and so forth. In addition, when co-administered with one or more biologically active agents, the compound provided herein is administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (A1-A6), (B1-B6), (C1-C6), or (D1-D6) described herein) are optionally administered in any order or even simultaneously. If simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses is from about more than zero weeks to less than about four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

In some embodiments, the pharmaceutical agents which make up the combination therapy disclosed herein are administered in a combined dosage form, or in separate dosage forms intended for substantially simultaneous administration. In some embodiments, the pharmaceutical agents that make up the combination therapy are administered sequentially, with either therapeutic compound being administered by a regimen calling for two-step administration. In some embodiments, the two-step administration regimen calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval.

In addition, the compounds described herein also are optionally used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies are administered before, during or after the occurrence of a disorder, and the timing of administering the composition containing a compound is variable. In some embodiments, the compounds are used as a prophylactic and are administered continuously to subjects with a propensity to develop conditions or diseases in order to prevent the occurrence of the disorder. In some embodiments, the compounds and compositions are administered to an individual during or as soon as possible after the onset of the symptoms. In some embodiments, the administration of the compounds is initiated within the first 48 hours of the onset of the symptoms, within the first 6 hours of the onset of the symptoms, or within 3 hours of the onset of the symptoms. In some embodiments, the initial administration is via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disorder is detected or suspected, and for a length of time necessary for the treatment of the disease, such as, for example, from about 1 month to about 3 months. The length of treatment can vary for each subject, and the length can be determined using the known criteria. In some embodiments, the compound or a formulation containing the compound is administered for at least 2 weeks, between about 1 month to about 5 years, or from about 1 month to about 3 years.

Exemplary Therapeutic Agents for Use in Combination with an Irreversible Inhibitor Compound In some embodiments, where the subject is suffering from or at risk of suffering from a disorder characterized by the presence or development of one or more solid tumors, the subjected is treated with an irreversible Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and, in some embodiments, are useful for treating cancer in combination with the compounds described herein.

Further examples of anti-cancer agents for use in combination with an irreversible Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents for use in combination with an irreversible Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents for use in combination with an irreversible Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents for use in combination with an irreversible Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomustine, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with an irreversible Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use employed in combination an irreversible Btk inhibitor compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomustine, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with an irreversible Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents for use in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation marketed drugs and drugs in development.

Where the subject is suffering from or at risk of suffering from a thromboembolic disorder (e.g., stroke), in some embodiments, the individual is treated with an irreversible Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), factor VIIa inhibitors, ticlopidine, clopidogrel, CS-747 (prasugrel, LY640315), ximelagatran, or BIBR 1048.

Pharmaceutical Composition/Formulation

Pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999).

A pharmaceutical composition, as used herein, refers to a mixture of a compound described herein, such as, for example, compounds of any of Formula (A1-A6), Formula (B1-B6), Formula (C1-C6), Formula (D1-D6), Formula (I), or Formula (VII), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disorder to be treated. Preferably, the mammal is a human. The compounds can be used singly or in combination with one or more therapeutic agents as components of mixtures.

The pharmaceutical formulations described herein are administered to an individual by any suitable administration route, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (A1-A6), Formula (B1-B6), Formula (C1-C6), Formula (D1-D6), Formula (I), or Formula (VII), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds exist as tautomers. All tautomers are included within the scope of the compounds presented herein. Additionally, in some embodiments, the compounds described herein exist in unsolvated as well as solvated forms with pharmaceutically acceptable solvents such as water, ethanol, and the like. The solvated forms of the compounds presented herein are also considered to be disclosed herein.

A "carrier" or "carrier materials" includes excipients in pharmaceutics and is selected on the basis of compatibility with compounds disclosed herein, such as, compounds of any of Formula (A1-A6), Formula (B1-B6), Formula (C1-

C6), Formula (D1-D6), Formula (I), or Formula (VII), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action. "Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

Dosage Forms

Moreover, the pharmaceutical compositions described herein, which include a compound of any of Formula (A1-A6), Formula (B1-B6), Formula (C1-C6), Formula (D1-D6), Formula (I), or Formula (VII) are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (A1-A6), Formula (B1-B6), Formula (C1-C6), Formula (D1-D6), Formula (I), or Formula (VII). In one embodiment, some or all of the particles of the compound of any of Formula (A1-A6), Formula (B1-B6), Formula (C1-C6), Formula (D1-D6), Formula (I), or Formula (VII), are coated. In another embodiment, some or all of the particles of the compound of any of Formula (A1-A6), Formula (B1-B6), Formula (C1-C6), Formula (D1-D6), Formula (I), or Formula (VII), are microencapsulated. In still another embodiment, the particles of the compound of any of Formula (A1-A6), Formula (B1-B6), Formula (C1-C6), Formula (D1-D6), Formula (I), or Formula (VII), are not microencapsulated and are uncoated.

Examples of Methods of Dosing and Treatment Regimens

In some embodiments, the compounds described herein are used in the preparation of medicaments for the inhibition of Btk or a homolog thereof, or for the treatment of diseases or conditions that benefit, at least in part, from inhibition of Btk or a homolog thereof. In some embodiments, the compounds described herein are used in the preparation of medicaments for the inhibition of HER4 or a homolog thereof, or for the treatment of diseases or conditions that benefit, at least in part, from inhibition of HER4 or a homolog thereof. In addition, a method for treating any of the diseases or conditions described herein in an individual in need of such treatment, involves administration of pharmaceutical compositions containing at least one compound of any of Formula (A1-A6), Formula (B1-B6), Formula (C1-C6), Formula (D1-D6), Formula (I), or Formula (VII), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In some embodiments, the compositions containing the compound(s) described herein are administered for prophylactic and/or therapeutic treatments. In therapeutic applications, the compositions are administered to an individual already suffering from a disorder, in an amount sufficient to cure or at least partially arrest the symptoms of the disorder. Amounts effective for this use will depend on the severity and course of the disorder, previous therapy, the patient's health status, weight, and response to the drugs, and the judgment of the treating physician.

In prophylactic applications, compositions containing the compounds described herein are administered to an individual susceptible to or otherwise at risk of a particular disease, disorder. Such an amount is defined to be a "prophylactically effective amount or dose." In this use, the precise amounts also depend on the patient's state of health, weight, and the like. When used in an individual, effective amounts for this use will depend on the severity and course of the disease, disorder, previous therapy, the patient's health status and response to the drugs, and the judgment of the treating physician.

In some embodiments, the irreversible kinase inhibitor is administered to the patient on a regular basis, e.g., three times a day, two times a day, once a day, every other day or every 3 days. In other embodiments, the irreversible kinase inhibitor is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the irreversible kinase inhibitor is administered only when the patient exhibits a particular symptom, e.g., the onset of pain, or the onset of a fever, or the onset of an inflammation, or the onset of a skin disorder.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder is retained. Patients can, however, require intermittent treatment on a long-term basis upon any recurrence of symptoms.

The amount of a given agent that will correspond to such an amount will vary depending upon factors such as the particular compound, disorder and its severity, the identity (e.g., weight) of the subject or host in need of treatment, and is determined according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disorder to be treated, the mode of administration, the requirements of the individual subject, the severity of the disorder being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Dosing Strategies to Increase Selectivity

Described herein are irreversible kinase inhibitors that are selective for one or more ACKs, including Btk, a Btk homolog, an ACK, HERO, and a Btk kinase cysteine homolog. In some embodiments, the irreversible inhibitors described herein also bind reversibly to other kinases (some of which, in some embodiments, are also ACKs). As a means of enhancing the selectivity profile, such inhibitors are formulated (formulation includes chemical modifications of the inhibitor, use of excipients in a pharmaceutical composition, and combinations thereof) such that the pharmacokinetic profile favors enhanced selectivity of the inhibitors for an ACK over a non-ACK. By way of example only, an ACK is formulated to have a short plasma half-life. In other embodiments, an ACK is formulated to have an extended plasma half-life.

Figure 5:
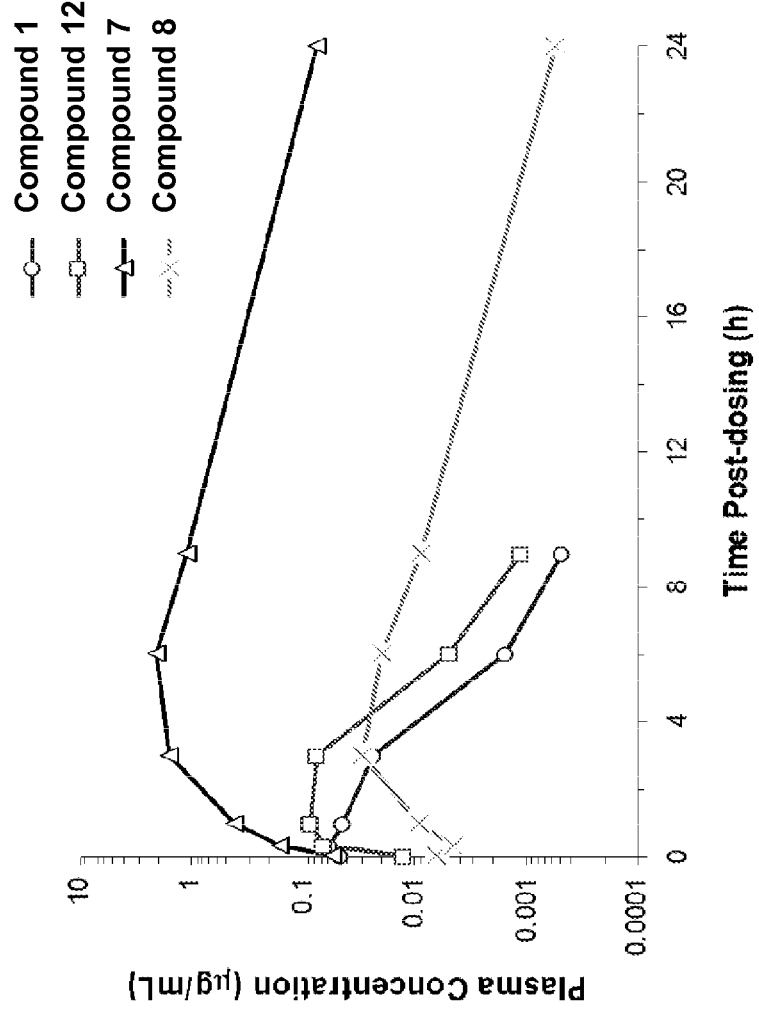
FIG. 5 presents an illustrative line graph showing in vivo plasma concentrations post-dosing of male jugular vein cannulated rats with Compounds 1, 7, 8, and 12. Blood samples were collected at 0.0833 (5 minutes), 0.333 (20 minutes), 1, 3, 6, 9, and 24 hours post-dosing from orally dosed rats. Compound 1 and Compound 12 have a short half-life in vivo. In contrast, Compound 7 and Compound 8 have a significantly longer in vivo half-life. Compounds like 1 and 12 are predicted to have enhanced kinase selectivity in vivo because inhibition will be sustained only for those kinases that are irreversibly inhibited.

For example, as shown in the Examples, Compound 1 and Compound 12 have a short half-life in vivo. In contrast, Compound 7 and Compound 8 have a significantly longer in vivo half-life (FIG. 5). Compounds like 1 and 12 are predicted to have enhanced kinase selectivity in vivo because inhibition will be sustained only for those kinases that are irreversibly inhibited. Further, given that the irreversible kinase inhibitors described herein have both reversible (in general to non-ACKs) and irreversible (generally, to ACKs) activities, in vivo properties of absorption, distribution, metabolism and excretion (ADME) are selected in order to optimize the therapeutic index. Specifically, in some embodiments, rapidly cleared compounds cause only brief inhibition of reversibly inhibited targets while maintaining sustained inhibition of irreversibly inhibited targets. Depending on the degree to which sustained inhibition of particular targets results in therapeutic effects or toxicities, we identify compounds with an optimal combination of in vitro selectivity profiles and in vivo ADME properties.

In one embodiment are kinase inhibitors that selectively and irreversibly binds to a protein tyrosine kinase selected from Btk, a Btk homolog, an ACK, HER4, and a Btk kinase cysteine homolog, in which the kinase inhibitor reversibly and non-selectively binds to a multiplicity of protein tyrosine kinases, and further in which the plasma half life of the kinase inhibitor is less than about 4 hours. In such an embodiment, the kinase inhibitor selectively and irreversibly binds to at least one of Btk, Jak3, Blk, Bmx, Tec, and Itk. In a further embodiment, the kinase inhibitor selectively and irreversibly binds to Btk. In a further embodiment, the kinase inhibitor selectively and irreversibly binds to Jak3. In a further embodiment, the kinase inhibitor selectively and irreversibly binds to Tec. In a further embodiment, the kinase inhibitor selectively and irreversibly binds to Btk and Tec. In a further embodiment, the kinase inhibitor selectively and irreversibly binds to Blk. In a further embodiment, the kinase inhibitor reversibly and non-selectively binds to a multiplicity of src-family protein kinase inhibitors. In a further embodiment, the plasma half life of the kinase inhibitor is less than about 3 hours. In a further embodiment, the plasma half life of the kinase inhibitor is less than about 2 hours.

In one embodiment are kinase inhibitors that selectively and irreversibly binds to a protein tyrosine kinase selected from Btk, a Btk homolog, an ACK, HER4, and a Btk kinase cysteine homolog, in which the kinase inhibitor reversibly and non-selectively binds to a multiplicity of protein tyrosine kinases, and further in which the plasma half life of the kinase inhibitor is greater than about 12 hours. In such an embodiment, the kinase inhibitor selectively and irreversibly binds to at least one of Btk, Jak3, Blk, Bmx, Tec, and Itk. In a further embodiment, the kinase inhibitor selectively and irreversibly binds to Btk. In a further embodiment, the kinase inhibitor selectively and irreversibly binds to Jak3. In a further embodiment, the kinase inhibitor selectively and irreversibly binds to Tec. In a further embodiment, the kinase inhibitor selectively and irreversibly binds to Btk and Tec. In a further embodiment, the kinase inhibitor selectively and irreversibly binds to Blk. In a further embodiment, the kinase inhibitor reversibly and non-selectively binds to a multiplicity of src-family protein kinase inhibitors In a further embodiment, the kinase inhibitor the plasma half life of the kinase inhibitor is greater than about 16 hours.

In one particular embodiment of any of the aforementioned kinase inhibitors, such kinase inhibitors have the structure of Formula (VII):

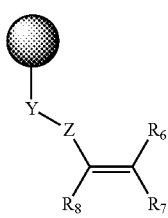

Formula (VII)

wherein:
wherein

is a moiety that binds to the active site of a kinase, including a tyrosine kinase, further including a Btk kinase cysteine homolog;
Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene;
Z is C(=O), OC(=O), NHC(=O), NCH$_3$C(=O), C(=S), S(=O)$_x$, OS(=O)$_x$, NHS(=O)$_x$, where x is 1 or 2;
R$_7$ and R$_8$ are independently selected from among H, unsubstituted C$_1$-C$_4$ alkyl, substituted C$_1$-C$_4$alkyl, unsubstituted C$_1$-C$_4$heteroalkyl, substituted C$_1$-C$_4$heteroalkyl, unsubstituted C$_3$-C$_6$cycloalkyl, substituted C$_3$-C$_6$cycloalkyl, unsubstituted C$_2$-C$_6$heterocycloalkyl, and substituted C$_2$-C$_6$heterocycloalkyl; or
R$_7$ and R$_8$ taken together form a bond;
R$_6$ is H, substituted or unsubstituted C$_1$-C$_4$alkyl, substituted or unsubstituted C$_1$-C$_4$heteroalkyl, C$_1$-C$_6$alkoxyalkyl, C$_1$-C$_8$alkylaminoalkyl, C$_1$-C$_8$hydroxyalkylaminoalkyl, substituted or unsubstituted C$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_4$alkyl(C$_3$-C$_8$cycloalkyl), or C$_1$-C$_4$alkyl(C$_2$-C$_8$heterocycloalkyl); and
pharmaceutically active metabolites, or pharmaceutically acceptable solvates, pharmaceutically acceptable salts, or pharmaceutically acceptable prodrugs thereof.

In a further embodiment,

on the kinase inhibitor is a substituted fused biaryl moiety selected from

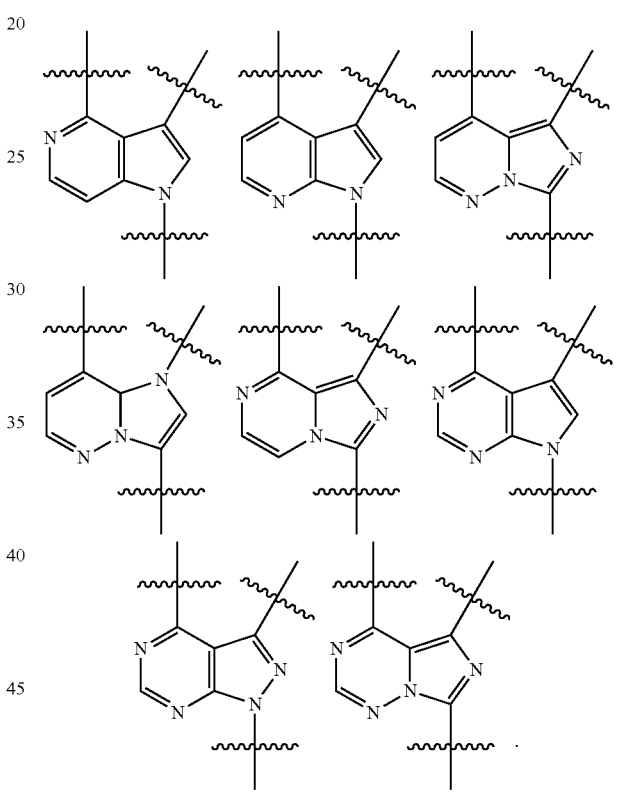

In a further embodiment of such kinases:
Z is C(=O), NHC(=O), NCH$_3$C(=O), or S(=O)$_2$.
The kinase inhibitor of Claim 49, wherein:
each of R$_7$ and R$_8$ is H; or
R$_7$ and R$_8$ taken together form a bond.

In a further embodiment of such kinases:
R$_6$ is H, substituted or unsubstituted C$_1$-C$_4$alkyl, substituted or unsubstituted C$_1$-C$_4$heteroalkyl, C$_1$-C$_6$alkoxyalkyl, C$_1$-C$_8$alkylaminoalkyl, C$_1$-C$_8$hydroxyalkylaminoalkyl, C$_1$-C$_8$alkoxyalkylaminoalkyl, C$_1$-C$_4$alkyl(aryl), C$_1$-C$_4$alkyl (heteroaryl), C$_1$-C$_4$alkyl(C$_3$-C$_8$cycloalkyl), or C$_1$-C$_4$alkyl (C$_2$-C$_8$heterocycloalkyl).

In a further embodiment of such kinases:
Y is a 4-, 5-, 6-, or 7-membered cycloalkylene ring; or
Y is a 4-, 5-, 6-, or 7-membered heterocycloalkylene ring; or
Y is a C$_1$-C$_4$ alkylene, or 4-, 5-, 6-, or 7-membered heterocycloalkylene ring.

In another aspect of such dosing methods are pharmaceutical formulations comprising any of the aforementioned ACK inhibitors and a pharmaceutically acceptable excipient. In some embodiments, such pharmaceutical formulations are formulated for a route of administration selected from oral administration, parenteral administration, buccal administration, nasal administration, topical administration, or rectal administration. In certain embodiments, the pharmaceutical formulations are formulated for oral administration.

In another aspect of such dosing methods are methods for treating rheumatoid arthritis comprising administering to an individual any of the aforementioned ACK inhibitors that selectively and irreversibly binds to Btk and Tec.

In yet another aspect of such dosing strategies are methods for increasing the selectivity of a test protein tyrosine kinase inhibitor that irreversibly and selectively binds to at least one protein kinase inhibitor selected from Btk, a Btk homolog, a Btk kinase cysteine homolog, an ACK, or HER4, in which the test protein tyrosine kinase inhibitor is chemically modified to decrease the plasma half life to less than about 4 hours. In some embodiments, the test protein tyrosine kinase inhibitor is chemically modified to decrease the plasma half life to less than about 3 hours.

In further embodiments, the test protein tyrosine kinase inhibitor has the structure of Formula (VII):

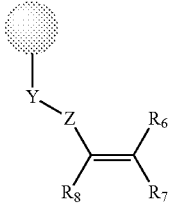

Formula (VII)

wherein

is a moiety that binds to the active site of a kinase, including a tyrosine kinase, further including a Btk kinase cysteine homolog;

Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene;

Z is $C(=O)$, $OC(=O)$, $NHC(=O)$, $NCH_3C(=O)$, $C(=S)$, $S(=O)_x$, $OS(=O)_x$, $NHS(=O)_x$, where x is 1 or 2;

$R_7$ and $R_8$ are independently selected from among H, unsubstituted $C_1$-$C_4$ alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond; and $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl).

In a further embodiment, the test protein tyrosine kinase inhibitor non-selectively and reversibly binds to a multiplicity of src-family protein tyrosine kinases.

In a further aspect of such dosing strategies are methods for treating a disorder characterized by the presence or development of one or more solid tumors comprising administering to an individual in need a pharmaceutical composition of any of the aforementioned ACK inhibitors. For example, as presented in the Examples, brief exposure to Compound 1 in vitro is sufficient to inhibit B cell activation in normal human B cells. This protocol mimics the predicted exposure of cells to Compound 1 in vivo and demonstrates that inhibition of B cells is sustained despite washing out of Compound 1.

Kits/Articles of Manufacture

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of Btk, or in which Btk is a mediator or contributor to the symptoms or cause.

For example, the container(s) include one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.
Synthesis of Compounds Example 1: Preparation of 4-Amino-3-(4-phenoxyphenyl)-1H-pyrazolo[3,4-d]pyrimidine (Intermediate 2)

4-Amino-3-(4-phenoxyphenyl)-1H-pyrazolo[3,4-d]pyrimidine (Intermediate 2) is prepared as disclosed in International Patent Publication No. WO 01/019829. Briefly, 4-phenoxybenzoic acid (48 g) is added to thionyl chloride (100 mL) and heated under gentle reflux for 1 hour. Thionyl chloride is removed by distillation, the residual oil dissolved in toluene and volatile material removed at 80° C./20 mbar. The resulting acid chloride is dissolved in toluene (200 mL) and tetrahydrofuran (35 mL). Malononitrile (14.8 g) is added and the solution and stirred at −10° C. while adding diisopropylethylethylamine (57.9 g) in toluene (150 mL), while maintaining the temperature below 0° C. After 1 hour at 0° C., the mixture is stirred at 20° C. overnight. Amine hydrochloride is removed by filtration and the filtrate evaporated in vacuo. The residue is taken up in ethyl acetate and washed with 1.25 M sulphuric acid, then with brine and dried over sodium sulfate. Evaporation of the solvents gives a semisolid residue which is treated with a little ethyl acetate to give 4.1 g of 1,1-dicyano-2-hydroxy-2-(4-phenoxyphenyl)ethene as a white solid (m.p. 160-162° C.). The filtrate on evaporation gives 56.58 (96%) of 1,1-dicyano-2-hydroxy-2-(4-phenoxyphenyl)ethene as a grey-brown solid, which is sufficiently pure for further use.

1,1-Dicyano-2-hydroxy-2-(4-phenoxyphenyl)ethene (56.5 g) in acetonitrile (780 mL) and methanol (85 mL) is stirred under nitrogen at 0° C. while adding diisopropylethylamine (52.5 mL) followed by 2M trimethylsilyldiazomethane (150 mL) in THF. The reaction is stirred for 2 days at 20° C., and then 2 g of silica is added (for chromatography). The brown-red solution is evaporated in vacuo, the residue dissolved in ethyl acetate and washed well with water then brine, dried and evaporated. The residue is extracted with diethyl ether (3×250 mL), decanting from insoluble oil. Evaporation of the ether extracts gives 22.5 g of 1,1-dicyano-2-methoxy-2-(4-phenoxyphenyl)ethene as a pale orange solid. The insoluble oil is purified by flash chromatography to give 15.0 g of a red-orange oil. 1,1-Dicyano-2-methoxy-2-(4-phenoxyphenyl)ethene (22.5 g) and 1,1-dicyano-2-methoxy-2-(4-phenoxyphenyl)ethene oil (15 g) are treated with a solution of hydrazine hydrate (18 mL) in ethanol (25 mL) and heated on the steambath for 1 hour. Ethanol (15 mL) is added followed by water (10 mL). The precipitated solid is collected and washed with ethanol:water (4:1) and then dried in air to give 3-amino-4-cyano-5-(4-phenoxyphenyl)pyrazole as a pale orange solid.

3-Amino-4-cyano-5-(4-phenoxyphenyl)pyrazole (29.5 g) is suspended in formamide (300 mL) and heated under nitrogen at 180° C. for 4 hours. The reaction mixture is cooled to 30° C. and water (300 mL) is added. The solid is collected, washed well with water, then with methanol and dried in air to give of 4-amino-3-(4-phenoxyphenyl)-1H-pyrazolo[3,4-d]pyrimidine.

Example 2: Synthesis of 1-(3-(4-amino-3-(4-phenoxyphenyl)-1H-pyrazolo[3,4-d]pyrimidin-1-yl)piperidin-1-yl)prop-2-en-1-one (Compound 13)

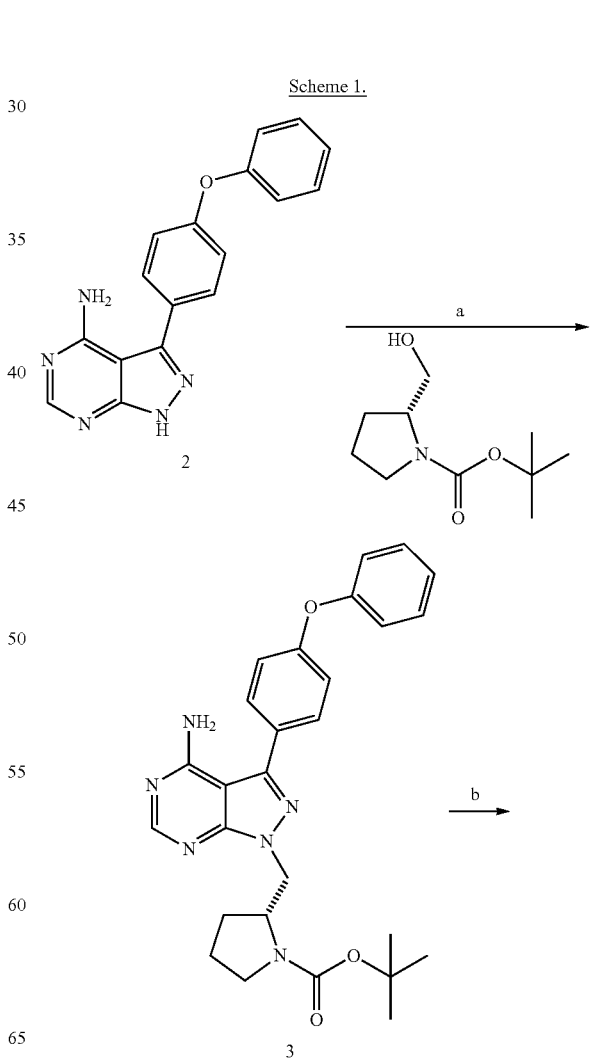

Scheme 1.

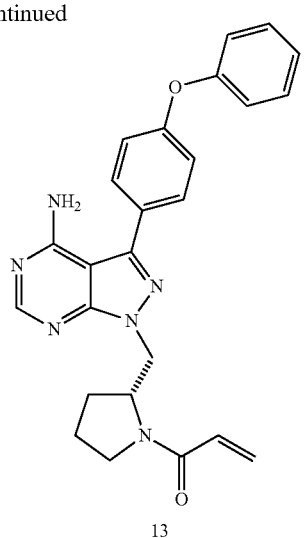

13

Synthesis of Compound 13; a) triphenylphosphine (TPP), diisopropyl diazodicarboxylate (DIAD), tetrahydrofuran (THF); b) TFA/CH$_2$Cl$_2$; then acryloyl chloride, diisopropylethylamine (DIPEA), tetrahydrofuran (THF).

Compounds described herein were synthesized by following the steps outlined in Scheme 1. A detailed illustrative example of the reaction conditions shown in Scheme 1 is described for the synthesis of 1-((R)-2-((4-amino-3-(4-phenoxyphenyl)-1H-pyrazolo[3,4-d]pyrimidin-1-yl)methyl)pyrrolidin-1-yl)prop-2-en-1-one (Compound 13).

0.5 g of 4-amino-3-(4-phenoxyphenyl)-1H-pyrazolo[3,4-d]pyrimidine and 0.65 g of triphenylphosphine (TPP) were mixed together with 15 mL of tetrahydrofuran (THF). (R)-tert-butyl 2-(hydroxymethyl)pyrrolidine-1-carboxylate (0.5 g; 1.5 equivalents) was added to the mixture followed by the addition of diisopropyl diazodicarboxylate (0.5 mL). The reaction mixture was stirred at room temperature for 4 hr. The reaction mixture was concentrated and purified by flash chromatography (acetone/CH$_2$Cl$_2$=1/1) to give intermediate 3 (1.49 g).

Intermediate 3 (1.49 g) was treated with 4 mL of TFA and 5 mL of CH$_2$Cl$_2$ and stirred overnight at room temperature and then concentrated to dryness. The residue was dissolved in ethyl acetate (100 mL) and then washed with dilute aq. NaHCO$_3$ (100 mL). The ethyl acetate layer was dried (MgSO$_4$), filtered and concentrated to ~20 mL and then 4.0 M HCl\dioxane (1 mL) was added and a yellow precipitate formed. The solid was collected by filtration and washed with ethyl acetate (20 mL). The solid was suspended in ethyl acetate (100 mL) and again washed with dilute aq. NaHCO$_3$ (100 mL). The ethyl acetate was dried (MgSO$_4$), filtered and concentrated to provide 0.43 g of a light yellow solid. The solid (0.14 g, 0.36 mmol) was stirred in THF (3 mL) and TEA (015 mL, 1.1 mmol) was added, followed by cooling the reaction with an ice bath for 30 min, then acryl chloride (30 µL, 0.36 mmol) added and the reaction was stirred for 2 hr. The reaction mixture was diluted with ethyl acetate (75 mL) and washed with dilute aq. NaHCO$_3$ (100 mL). The organic layer was dried (MgSO$_4$), filtered and concentrated. Flash chromatography (with CH$_2$Cl$_2$/MeOH=20/1) gave 90 mg of compound 4 as a white solid. EM (calc)=440.2; MS (M+1): 441.2.

Example 3: Synthesis of 1-((S)-2-((4-amino-3-(4-phenoxyphenyl)-1H-pyrazolo[3,4-d]pyrimidin-1-yl)methyl)pyrrolidin-1-yl)prop-2-en-1-one (Compound 14)

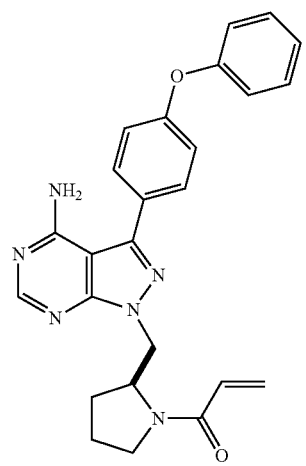

The synthesis of Compound 14 was accomplished using a procedure analogous to that described in Example 2. EM (calc.): 440.2; MS (M+1H): 441.2.

Example 4: Synthesis of N-((1r,4r)-4-(4-amino-3-(4-phenoxyphenyl)-1H-pyrazolo[3,4-d]pyrimidin-1-yl)cyclohexyl)acrylamide

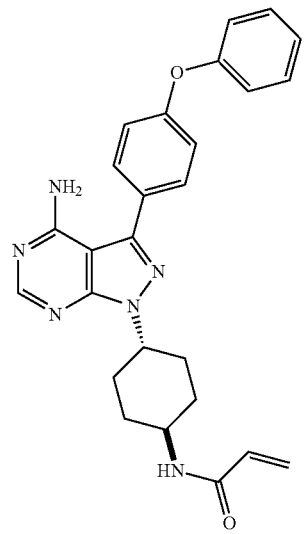 [SMILES: C=CC(=O)N[C@H]1CC[C@H](n2nc(-c3ccc(Oc4ccccc4)cc3)c3c(N)ncnc32)CC1]

The synthesis of this compound was accomplished using a procedure analogous to that described for Example 2 EM (calc.): 454.21; MS (M+1): 455.2.

Example 5: Synthesis of N-(2-(4-amino-3-(4-phenoxyphenyl)-1H-pyrazolo[3,4-d]pyrimidin-1-yl)ethyl)-N-methylacrylamide (Compound 19)

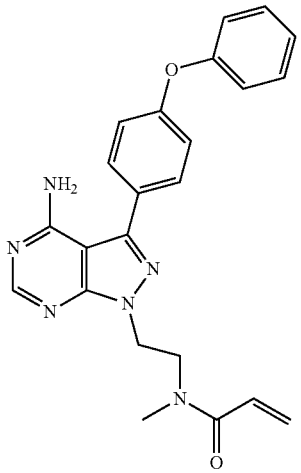 [SMILES: C=CC(=O)N(C)CCn1nc(-c2ccc(Oc3ccccc3)cc2)c2c(N)ncnc21]

The synthesis of this compound was accomplished using a procedure analogous to that described for Example 2. EM (calc.): 414.18; MS (M+1H): 415.2.

Example 6: Synthesis of N-(2-(4-amino-3-(4-phenoxyphenyl)-1H-pyrazolo[3,4-d]pyrimidin-1-yl)ethyl)acrylamide (Compound 23)

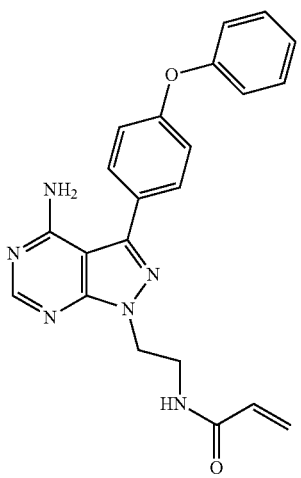 [SMILES: C=CC(=O)NCCn1nc(-c2ccc(Oc3ccccc3)cc2)c2c(N)ncnc21]

The synthesis of this compound was accomplished using a procedure analogous to that described for Example 2. EM (calc.): 400.16; MS (M+1H): 401.2.

Example 7: Synthesis of 1-((R)-3-(4-amino-3-(4-phenoxyphenyl)-1H-pyrazolo[3,4-d]pyrimidin-1-yl)piperidin-1-yl)but-2-yn-1-one e (Compound 17)

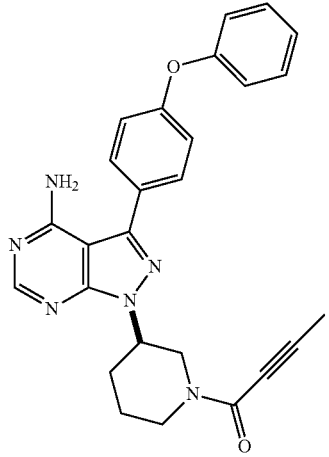

The synthesis of this compound was accomplished using a procedure analogous to that described for Example 2. EM (calc.): 452.2; MS (M+1H): 453.2.

Example 8: Synthesis of 1-((R)-2-((4-amino-3-(4-phenoxyphenyl)-1H-pyrazolo[3,4-d]pyrimidin-1-yl)methyl)pyrrolidin-1-yl)but-2-yn-1-one (Compound 15)

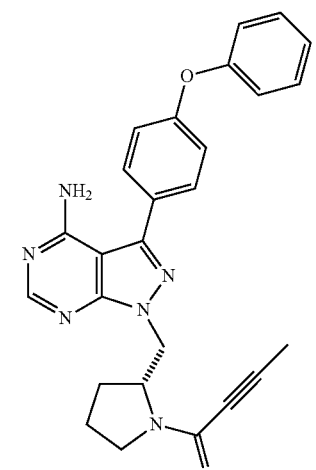

The synthesis of this compound was accomplished using a procedure analogous to that described for Example 2. EM (calc.): 452.2; MS (M+1H): 453.2.

Example 9: Synthesis of (E)-1-((R)-2-((4-amino-3-(4-phenoxyphenyl)-1H-pyrazolo[3,4-d]pyrimidin-1-yl)methyl)pyrrolidin-1-yl)-4-(dimethylamino)but-2-en-1-one (Compound 11)

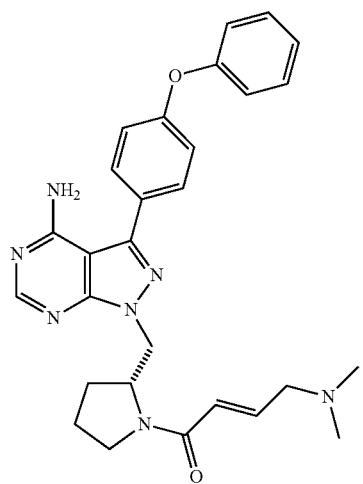

The synthesis of this compound was accomplished using a procedure analogous to that described for Example 2. EM (calc.): 497.25; MS (M+1H): 498.2.

Therapeutic Uses of Inhibitor Compounds

Example 1: Inhibition of Lymphoma Tumor Cell Growth

Compound 1 inhibits lymphoma tumor cell growth. A variety of lymphoma cell lines were incubated with a range of concentrations of Compound 1 to determine the GI50, the concentration that results in 50% decrease in cell proliferation (FIG. 1A). Compound 1 inhibits tumor growth in DOHH2 and DLCL2 xenograft models (FIGS. 1B and 1C).

For in vitro cell proliferation assays, cells were seeded in 96-well plates in standard growth media (in most cases RPMI+10% fetal calf serum) and Compound 1 was added in a 9-point dilution series ranging from 10 uM to 0.04 uM with DMSO at 0.1% final concentration in all wells. After 72 hours, cell number was measured using Alamar Blue using manufacturer's protocol. A dilution series of untreated cells was run in parallel to verify that the Alamar Blue assay reliably reflected cell number and that growth conditions were not limiting. The GI50, the concentration that results in a 50% decrease in cell number, was calculated using Calcusyn to fit the dose-response curve. GI50 values were confirmed in two or more separate experiments for each cell line.

For in vivo lymphoma xenograft studies, 5E6 DOHH2 or DLCL2 cells in 50% matrigel were implanted subcutaneously in SCID mice and dosed orally with Compound 1 beginning when tumor size reached 100 mm2.

Example 2: Inhibition of Collagen-Induced Arthritis in a Mouse

Compound 1 inhibits collagen-induced arthritis in the mouse. Male DBA/1OlaHsd mice were injected intradermally with 150 microliters of 2 mg/mL Type II collagen in Freund's complete adjuvant with supplemental *M. tuberculosis,* 4 mg/mL and boosted with the same injection 21 days later. After paw inflammation was established, animals were randomized and Compound for vehicle was dosed orally once per day starting at day 1. Paw inflammation was scored from 0-5 and averaged across all paws from all animals for each group in the study. Compound 1 at 12.5 mg/kg and 50 mg/kg regressed inflammation through the end of the study (day 11) while 3.125 mg/kg significantly reduced the increase in paw inflammation (FIG. 2). Dexamethasone was included as a positive control.

In another study, Compound 1 was dosed at 12.5 mg/kg to such mice over: (a) each day of an 11-day period; (b) days 1, 2, and 3 of an 11-day period; or (c) days 9, 10, and 11 of an 11-day period. Intermittent dosing reduced the increase in paw inflammation. In addition, Compound 9 was dosed to such mice at a level of 12.5 mg/kg or 50 mg/kg each day of an 11-day period. Compound 9 reduced the increase in paw inflammation.

Example 3: Inhibition of Lupus in a Mouse Model

Figure 3:
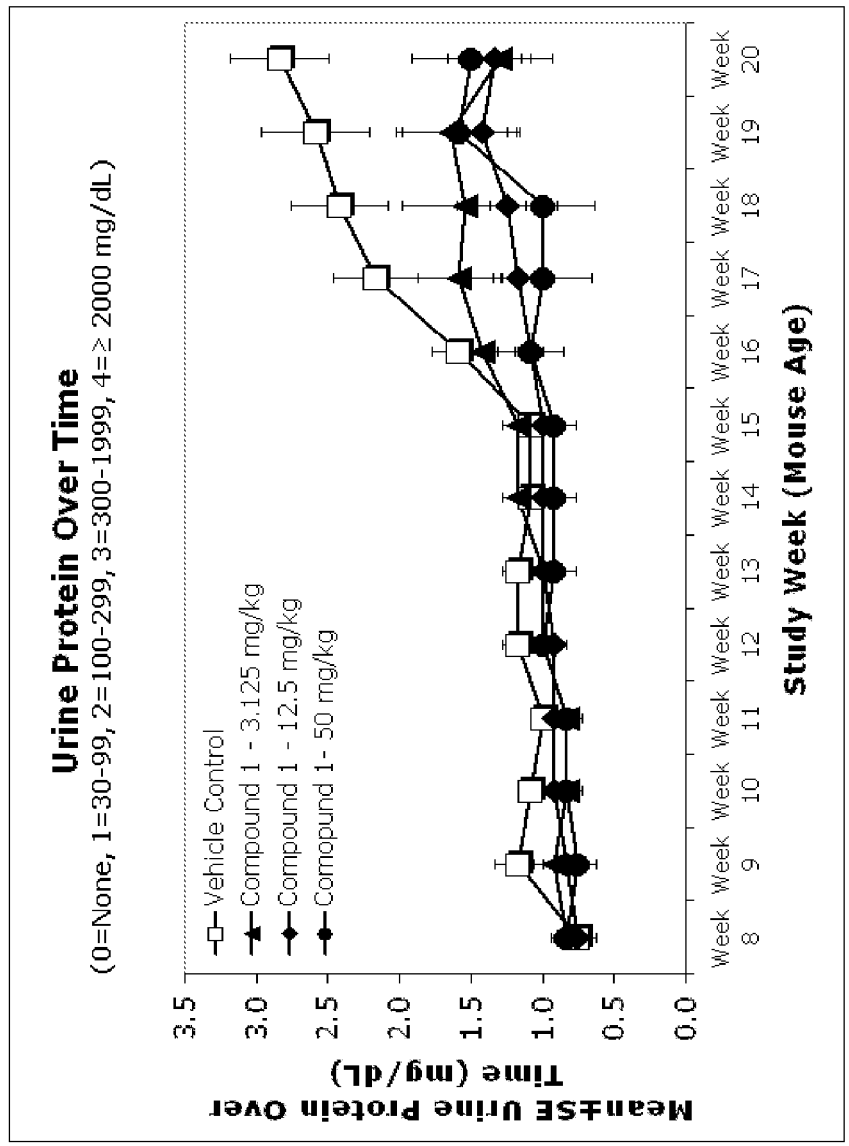
FIG. 3 presents an illustrative line graph showing inhibition of disease progression in a mouse MRL/lpr model of lupus. MRL/lpr mice (Jax strain 000485) were dosed orally once per day from 8 weeks of age until 20 weeks of age and urine protein levels were measured weekly. Compound 1 at 3.125 mg/kg, 12.5 mg/kg, and 50 mg/kg significantly reduced proteinuria, indicating amelioration of the progressive autoimmune renal failure seen in this mouse strain.

Compound 1 inhibits disease progression in the mouse MRL/lpr model of lupus. Compound 1 at 3.125 mg/kg, 12.5 mg/kg, and 50 mg/kg significantly reduced proteinuria, indicating amelioration of the progressive autoimmune renal failure seen in this mouse strain (FIG. 3). MRL/lpr mice (Jax strain 000485) were dosed orally once per day from 12 weeks of age until 20 weeks of age and urine protein levels were measured weekly using Clinitech Multistick dipstick.

Example 4: Inhibition of Mast Cell Degranulation

Figure 4:
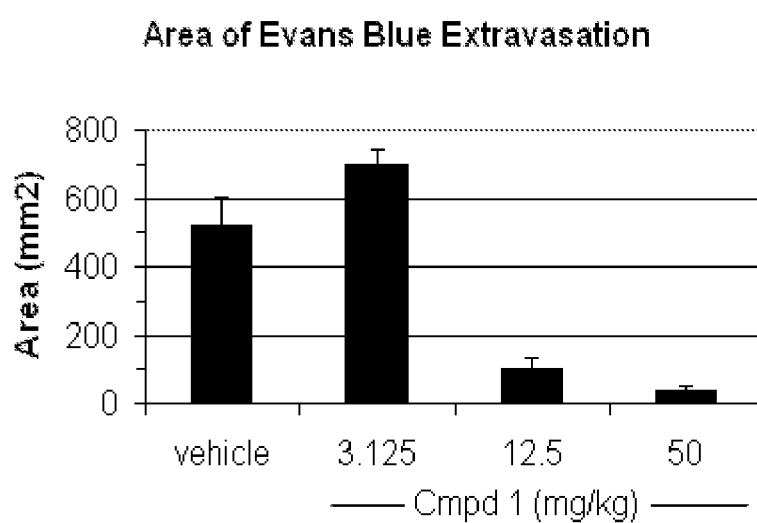
FIG. 4 presents an illustrative bar graph showing inhibition of mast cell degranulation in a mouse passive cutaneous anaphylaxis model. 23 hours after mice were sensitized with an intradermal injection of monoclonal anti-DNP-IgE in the back, they received a single oral dose of Compound 1 or vehicle. After one hour, animals were challenged with an intravenous injection of DNP-BSA and Evans Blue dye and the area of extravasation was measured. Increasing doses of Compound 1 significantly decreased the amount of Evans Blue release, indicating decreased mast cell activation and vascular permeabilization.

Compound 1 inhibits mast cell degranulation in a mouse passive cutaneous anaphylaxis model. Increasing doses of Compound 1 significantly decrease the amount of Evans Blue release, indicating decreased mast cell activation and vascular permeabilization. (FIG. 4)

Mice were sensitized with an intradermal injection of monoclonal anti-DNP-IgE in the back. 23 hours later they received a single oral dose of Compound 1 or vehicle. After one hour, animals were challenged with an intravenous injection of DNP-BSA and Evans Blue dye. Mast cell degranulation leads to vascular permeability and the distribution of the dye into the skin of the back. The area of extravasation after 1 hour is measured.

Example 5: Pharmaceutical Compositions

The compositions described below are presented with a compound of Formula (A1-A6) for illustrative purposes; any of the compounds of any of Formulas (A1-A6), (B1-B6), (C1-C6), or (D1-D6) are optionally used in such pharmaceutical compositions.

Example 5a: Parenteral Composition

To prepare a parenteral pharmaceutical composition suitable for administration by injection, 100 mg of a water-soluble salt of a compound of Formula (A1-A6) is dissolved in DMSO and then mixed with 10 mL of 0.9% sterile saline. The mixture is incorporated into a dosage unit form suitable for administration by injection.

Example 5b: Oral Composition

To prepare a pharmaceutical composition for oral delivery, 100 mg of a compound of Formula (A1-A6) is mixed

Example 5c: Sublingual (Hard Lozenge) Composition

To prepare a pharmaceutical composition for buccal delivery, such as a hard lozenge, mix 100 mg of a compound of Formula (A1-A6), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 5d: Inhalation Composition

To prepare a pharmaceutical composition for inhalation delivery, 20 mg of a compound of Formula (A1-A6) is mixed with 50 mg of anhydrous citric acid and 100 mL of 0.9% sodium chloride solution. The mixture is incorporated into an inhalation delivery unit, such as a nebulizer, which is suitable for inhalation administration.

Example 5e: Rectal Gel Composition

To prepare a pharmaceutical composition for rectal delivery, 100 mg of a compound of Formula (A1-A6) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 5f: Topical Gel Composition

To prepare a pharmaceutical topical gel composition, 100 mg of a compound of Formula (A1-A6) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 5g: Ophthalmic Solution Composition

To prepare a pharmaceutical ophthalmic solution composition, 100 mg of a compound of Formula (A1-A6) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 6: Levels of Tonic BCR Signaling Predict Response to Compound 1

To identify biomarkers that correlate with response to Compound 1, phosphorylation events in the BCR signal transduction pathway were investigated. A panel of phospho-specific antibodies that recognize activating phosphorylation sites on Syk, Btk, BLNK, PLC-g1, PLC-g2, ERK, and AKT were used and tested the effects of Compound 4 on both basal phosphorylation and phosphorylation following BCR stimulation driven by anti-IgM or anti-IgG cross-linking. We examined phosphorylation patterns in both a Compound 1 sensitive cell line (DOHH2) and a Compound 1 resistant cell line (Ramos).

Compound 1 inhibits most BCR-stimulus induced phosphorylation events with similar potency in both cell lines. However, when we examined basal phosphorylation levels, we found higher basal phosphorylation in DOHH2 compared to Ramos, with phospho-ERK in particular indicating higher levels of basal or tonic signaling in DOHH2. Furthermore, Compound 4 significantly decreased pERK levels in unstimulated DOHH2 cells (IC50<10 nM), but not in Ramos cells.

A panel of nine Btk expressing B cell lymphoma cell lines was screened for basal pERK levels. Seven lines expressed significantly higher levels of basal pERK, and of these, 5 were sensitive to Compound 1 (GI50<1.3 uM), while the two cell lines with low pERK levels were resistant to Compound 1. This data shows that tonic BCR signaling contributes to the survival of a subset of lymphoma cell lines, and that inhibition of this signaling by Compound 4 is correlated with induction of apoptosis.

Two additional experiments demonstrate that sensitivity to Compound 1 is correlated with high levels of pERK. First 1 uM of Compound 4 reduces expression of the known ERK transcriptional target Egr-1 within 1 hr, with maximal down-regulation (10-fold) achieved by 4 hr. Second, in the lymphoma cell line WSU-DLCL2, BCR cross-linking by anti-IgG (30 ug/ml) overcomes inhibition of pERK by Compound 4, showing that strong BCR stimulus activates parallel pathways to pERK that do not require Btk. BCR stimulus also rescues WSU-DLCL2 from Compound 1 induced cytotoxicity, further confirming that inhibition of pERK is correlated with apoptosis induction by Compound 1. Taken together these data show high levels of pERK or ERK transcriptional targets such as Egr-1 serve as useful markers for lymphomas in which tonic BCR signaling is contributing to cell survival and that these lymphomas are particularly sensitive to BCR pathway inhibitors such as Compound 1.

Kinase Inhibitor Discovery Platform and Pulse Dosing

Example 1: Design of an Inhibitor

Because the ATP binding sites of the >500 kinases in the human genome are highly conserved, it has proven difficult to engineer selectivity for individual kinases using conventional reversible binding inhibitors. For our highly selective BTK inhibitor Compound 1, we engineered an electrophilic center capable of irreversibly inactivating the target enzyme, BTK. The approach employed structure based design to achieve a high degree of potency and selectivity by (1) fitting the core scaffold into the active site ATP binding pocket of kinase enzymes, and (2) forming a covalent bond with Cysteine-481 located in BTK. The unique chemistry required for covalent bond formation involves an electrophilic moiety that acts as a Michael acceptor, which bonds with a nucleophile (such as Cys-481) present in a precise location within the active site.

Example 2: Inhibitor Screening Approach

By way of example only, a panel of 50-100 Cys-targeting kinase inhibitors is generated. The molecular orientation and positioning of the electrophilic group in these inhibitors in relation to the Cysteine residue will affect the potency and selectivity of a given inhibitor. Each inhibitor will then be profiled for kinetics of kinase inhibition ($K_i$) for each of the ten Cys-containing kinases, effect on tumor cell proliferation ($GI_{50}$), effect on relevant off-targets (hERG, CYPs), drug-like characteristics (solubility, clogP) and ability to block labeling by the active site probe. This panel of diverse inhibitors are then be used in cell assays (for example, inhibition of tumor growth) to screen for a phenotype of interest. With the phenotype, the identification of additional inhibited kinases is determined using the active site probe and mass spectrometry.

Example 3: Inhibition of a Panel of Kinases for Compound 1 and Compound 9

In another example, the linker and Michael acceptor moiety of Compound 1 was modified to provide Compound 9 which has a different selectivity pattern. Table 1 is a table showing the degree of inhibition of a panel of kinases for two example compounds. $IC_{50}$s were determined using the in vitro HotSpot kinase assay (purified enzymes, $^{33}$P-ATP, an appropriate substrate and 1 uM ATP.) Compared to Compound 1, Compound 9 has similar potency toward Btk, but significantly less potency toward JAK-3, ITK, and EGFR and significantly more potency toward the src-family kinases lck, c-src, FGR, Fyn, Hck, and Lyn and Yes. Thus, subtle modifications in the linker moiety and the Michael acceptor moiety are important for the design of selective ACK inhibitors.

TABLE 1

| Kinase | Compound 1 IC50 (nM) | Compound 9 IC50 (nM) |
| --- | --- | --- |
| BTK | 0.5 | 1.0 |
| ITK | 11.7 | 909.9 |
| Bmx/ETK | 0.8 | 1.1 |
| TEC | 77.8 | 108.0 |
| EFGR | 0.5 | 20.6 |
| HER4 | 9.4 | 1536.0 |
| HER4 | 0.1 | 3.2 |
| LCK | 2.0 | 1.0 |
| BLK | 0.5 | 0.2 |
| C-src | 262.6 | 14.3 |
| FGR | 2.3 | 0.4 |
| Fyn | 95.6 | 7.1 |
| HCK | 3.7 | 1.0 |
| Lyn | 16.2 | 1.2 |
| YES | 6.5 | 0.8 |
| ABL | 86.1 | 32.3 |
| Brk | 3.3 | 3.3 |
| CSK | 2.2 | 2.4 |
| FER | 8,070.0 | 3,346.0 |
| JAK3 | 10.4 | 8,278.0 |
| SYK | >10,000 | >10,000 |

Example 4: Modification of Linker and Michael Acceptor Moieties and In Vitro Inhibitory Activity In this example, compounds are selected based on in vitro characteristics to optimize for potency of inhibition of particular kinases and degree of covalent binding to off-target cysteines such as glutathione. For example, in Table 2, Compound 9 and Compound 12 both inhibit Btk with a similar potency as Compound 1, but they are both significantly less potent inhibitors of EGFR, ITK, and JAK-3. As another example, Compound 11 is similar to Compound 1 for inhibition of Btk but does not bind glutathione as readily.

A calculated value (e.g (1/Btk $IC_{50}$)/Glutathione conjugation rate) as shown in the Table 2) is used to compare compounds for their ratio between potency at inhibiting their target and their non-specific binding to other SH groups, such as those in glutathione. As shown in Table 2, this calculated value is 4.7 for Compound 1 and for 239.6 for Compound 11. Calculated ratios such as these are used to quantitatively compare different compounds and select compounds for further study.

Example 4a: Enzyme Inhibition

For enzyme inhibition assays, compounds were tested in range of ten concentrations from 10 uM to 0.0005 uM using purified enzymes and the Hotspot kinase assay. Reaction conditions were 1 uM ATP, one hour incubation with inhibitor, and kinase activity detected using 33-ATP phosphorylation of an appropriately selected peptide substrate. Dose-response curves were fit using Prism, and the $IC_{50}$, the concentration at which enzyme inhibition is 50% of maximal inhibition, was determined. See Table 2.

Example 4b: Glutathione Binding Assays

For the glutathione binding assays, 5 mM glutathione, 10 µM Btk inhibitor in DMSO (10 µL) and 6 equivalents of N'N' Diisopropyl ethyl amine were combined in 1 mL potassium phosphate buffer. The mixture was incubated for 0, 15, 60 minutes at room temperature and the reaction was stopped with 10 equivalents of formic acid. 50 µL of each reaction mixture was injected on HPLC (Mobil Phase A: 0.2% formic acid in water, Mobile Phase B: 0.2% formic acid in acetonitrile, HPLC Column: Metasil Basic 3 µL, 150×4.6 mm, 10% B, Gradient: 10% to 90% B, Detection: UV/Vis 260 nM). Rate of reaction was reported as nmole GSH conjugate conversion per minute from the normalized ratio for area under the curve from HPLC chromatograms for both GSH conjugate and the parent.

Example 4c: Cell Proliferation Assay

Analogs are generated that are Btk inhibitors and that are cytotoxic to the lymphoma cell line DOHH2. See Table 2. For the DOHH2 cell proliferation assay, cells were seeded in 96-well plates in standard growth media (RPMI+10% fetal calf serum) and compounds were added in a 9-point dilution series ranging from 10 uM to 0.04 uM with DMSO at 0.1% final concentration in all wells. After 72 hours, cell number was measured using Alamar Blue using manufacturer's protocol. A dilution series of untreated cells was run in parallel to verify that the Alamar Blue assay reliably reflected cell number and that growth conditions were not limiting. The $GI_{50}$, the concentration that results in a 50% decrease in cell number, was calculated using Calcusyn to fit the dose-response curve.

TABLE 2

| # | Compound Structure | BTK IC$_{50}$ (nM) | ITK IC$_{50}$ (nM) | EGFR IC$_{50}$ (nM) | LCK IC$_{50}$ (nM) | JAK3 IC$_{50}$ (nM) | Glutathione Conj Rate (nmol/min) | (1/BTK IC$_{50}$)/ Glutathione Rate | DOHH2 GI$_{50}$ (µM) |
|---|---|---|---|---|---|---|---|---|---|
| 1 | 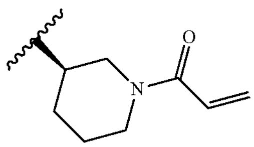 [SMILES: *[C@@H]1CCCN(C(=O)C=C)C1] | 0.5 | 11.7 | 0.5 | 2.0 | 10.4 | 0.398 | 4.7 | 0.1 |
| 2 | 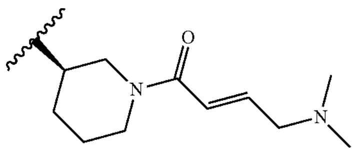 [SMILES: *[C@@H]1CCCN(C(=O)/C=C/CN(C)C)C1] | 1.1 | | 48.8 | | | | | 0.32 |
| 3 | 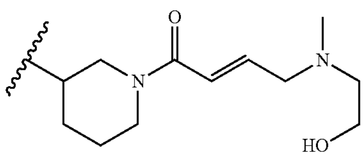 [SMILES: *C1CCCN(C(=O)/C=C/CN(C)CCO)C1] | 21 | | 74.5 | | | | | |
| 4 | 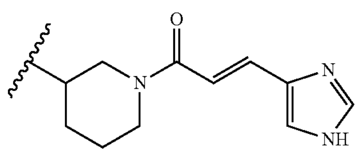 [SMILES: *C1CCCN(C(=O)/C=C/c2c[nH]cn2)C1] | 22.2 | | 487.6 | | | | | |
| 5 | 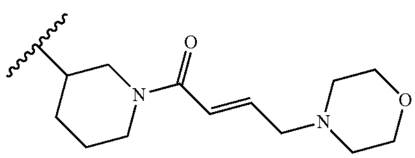 [SMILES: *C1CCCN(C(=O)/C=C/CN2CCOCC2)C1] | 5.6 | | 326.0 | | | 0.004 | 44.5 | |
| 6 | 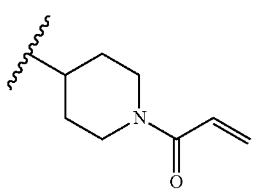 [SMILES: *C1CCN(C(=O)C=C)CC1] | 3.1 | | 60.9 | | | 0.39 | 0.8 | |
| 7 | 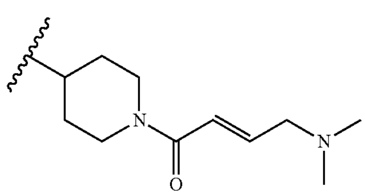 [SMILES: *C1CCN(C(=O)/C=C/CN(C)C)CC1] | 6.3 | 6,123 | 268.7 | 2.6 | >10,000 | 0.01 | 15.9 | 0.317 |
| 8 | 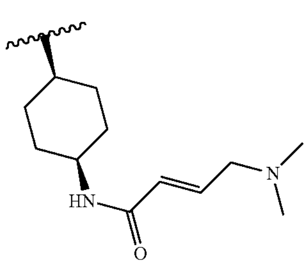 [SMILES: *[C@H]1CC[C@@H](NC(=O)/C=C/CN(C)C)CC1] | 1.4 | | 83.4 | | | | | |

TABLE 2-continued

| # | Compound Structure | BTK IC$_{50}$ (nM) | ITK IC$_{50}$ (nM) | EGFR IC$_{50}$ (nM) | LCK IC$_{50}$ (nM) | JAK3 IC$_{50}$ (nM) | Glutathione Conj Rate (nmol/min) | (1/BTK IC$_{50}$)/ Glutathione Rate | DOHH2 GI$_{50}$ (μM) |
|---|---|---|---|---|---|---|---|---|---|
| 9 | 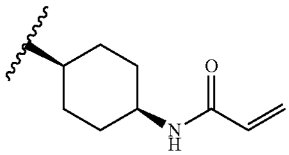 [SMILES: *[C@H]1CC[C@@H](NC(=O)C=C)CC1] | 1.0 | 909.9 | 20.6 | 1.0 | 8278.0 | | | 0.011 |
| 10 | 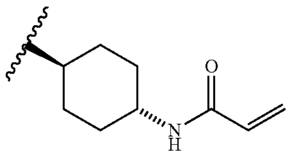 [SMILES: *[C@H]1CC[C@H](NC(=O)C=C)CC1] | 1.31 | 1954 | 44.5 | 0.88 | >10,000 | | | <0.03 |
| 11 | 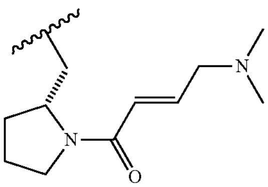 [SMILES: *C[C@H]1CCCN1C(=O)/C=C/CN(C)C] | 0.92 | 6891 | 18.85 | 2.43 | >10,000 | 0.004525 | 239.6 | >10 |
| 12 | 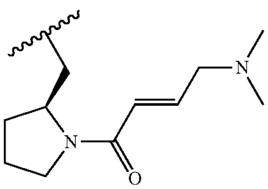 [SMILES: *C[C@@H]1CCCN1C(=O)/C=C/CN(C)C] | 1.33 | 14290 | 698.3 | 5.97 | >10,000 | 0.004361 | 172.2 | >10 |
| 13 | 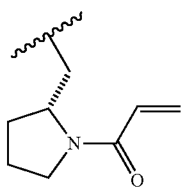 [SMILES: *C[C@H]1CCCN1C(=O)C=C] | 0.67 | 3013 | 18.75 | 1.56 | 12980 | | | 0.24 |
| 14 | 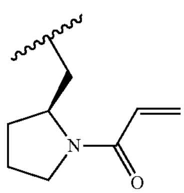 [SMILES: *C[C@@H]1CCCN1C(=O)C=C] | 0.39 | 592.3 | 2.298 | 9.24 | 1456 | | | 0.37 |
| 15 | 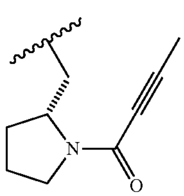 [SMILES: *C[C@H]1CCCN1C(=O)C#CC] | 4.16 | 21100 | 289.4 | 5.90 | >10,000 | | | 0.59 |
| 16 | 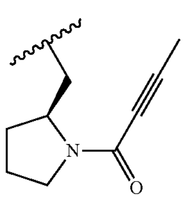 [SMILES: *C[C@@H]1CCCN1C(=O)C#CC] | 3.14 | >10,000 | 2807 | 3.82 | >10,000 | | | 0.21 |

TABLE 2-continued

| # | Compound Structure | BTK IC$_{50}$ (nM) | ITK IC$_{50}$ (nM) | EGFR IC$_{50}$ (nM) | LCK IC$_{50}$ (nM) | JAK3 IC$_{50}$ (nM) | Glutathione Conj Rate (nmol/min) | (1/BTK IC$_{50}$)/ Glutathione Rate | DOHH2 GI$_{50}$ (μM) |
|---|---|---|---|---|---|---|---|---|---|
| 17 | 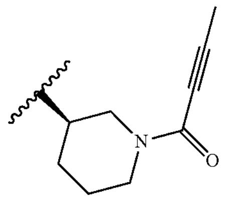 [SMILES: *[C@@H]1CCCN(C(=O)C#CC)C1] | 2.00 | 2333 | 435.3 | 2.07 | >10,000 | 0.0243 | 20.6 | 0.21 |
| 18 | 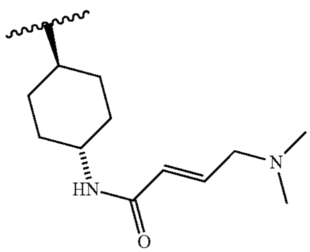 [SMILES: *[C@H]1CC[C@H](NC(=O)/C=C/CN(C)C)CC1] | 1.38 | 2536 | 22.53 | 0.76 | >10,000 | | | <0.03 |
| 19 | 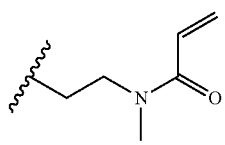 [SMILES: *CCN(C)C(=O)C=C] | 1.58 | 534.6 | 28.22 | 6.62 | 5997 | | | 0.69 |
| 20 | 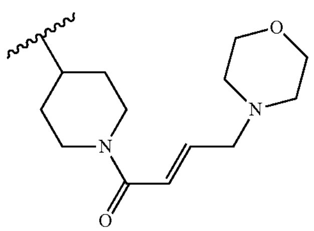 [SMILES: *C1CCN(C(=O)/C=C/CN2CCOCC2)CC1] | 4.07 | 7993 | 303.60 | 98.59 | >10,000 | | | 0.39 |
| 21 | 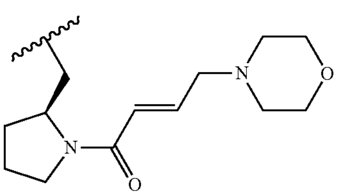 [SMILES: *C[C@@H]1CCCN1C(=O)/C=C/CN1CCOCC1] | 4.15 | >10,000 | 6238.00 | 1346 | >10,000 | | | 1.53 |
| 22 | 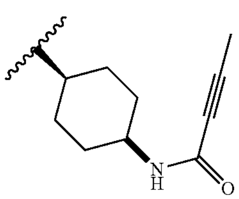 [SMILES: *[C@H]1CC[C@@H](NC(=O)C#CC)CC1] | 1.57 | 3691 | 156.30 | 22.12 | >10,000 | 0.014 | 45.4 | <0.04 |
| 23 | 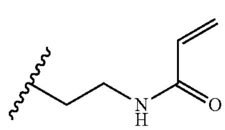 | 0.32 | 830 | 70.49 | 208.00 | 3306.00 | | | 0.11 |
| 24 | 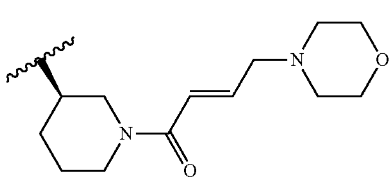 [SMILES: *[C@@H]1CCCN(C(=O)/C=C/CN2CCOCC2)C1] | 0.89 | 476 | 383.70 | 235.40 | 9077.00 | | | 0.44 |

TABLE 2-continued

| # | Compound Structure | BTK IC$_{50}$ (nM) | ITK IC$_{50}$ (nM) | EGFR IC$_{50}$ (nM) | LCK IC$_{50}$ (nM) | JAK3 IC$_{50}$ (nM) | Glutathione Conj Rate (nmol/min) | (1/BTK IC$_{50}$)/ Glutathione Rate | DOHH2 GI$_{50}$ (μM) |
|---|---|---|---|---|---|---|---|---|---|
| 25 | (structure) | 3.48 | >10,000 | 272.90 | 25.81 | >10,000 | | | 0.05 |

Example 5: Kinase Inhibitor Selectivity Predicted by Dosing

Compound 1 and Compound 12 have a short half-life in vivo. In contrast, Compound 7 and Compound 8 have a significantly longer in vivo half-life (FIG. 5). Compounds like 1 and 12 are predicted to have enhanced kinase selectivity in vivo because inhibition will be sustained only for those kinases that are irreversibly inhibited.

Male jugular vein cannulated rats were administered a single dose of all test compounds at 8 mg/kg each, in combination by oral gavage. Dose volumes were adjusted based on body weight data collected immediately prior to dosing. Blood samples were collected at 0.0833 (5 minutes), 0.333 (20 minutes), 1, 3, 6, 9, and 24 hours post-dosing from orally dosed rats. The samples were collected into plasma separator Microtainer tubes with anticoagulant (lithium heparin). Plasma samples were prepared by centrifugation (5 min at 5000×g), and at least 100 μL were transferred to storage tubes and stored frozen at −80° C. Plasma samples were thawed and 75 uL aliquots were transferred to centrifuge tubes to which 10 μL aliquots of internal standard solution (1 μg/mL) were added. The samples were not diluted with blank plasma prior to further processing. Soluble proteins were precipitated by the addition of 200 μL of acetonitrile, followed by centrifugation (20 min at 16,000×g). The samples were evaporated to dryness and reconstituted in 200 μL of water containing 0.2% formic acid and 10% methanol. All samples were loaded onto an auto sampler maintained at 6° C. and evaluated for concentrations of test compounds using LC-MS/MS.

Example 6: B Cell Inhibition

Figure 6A:
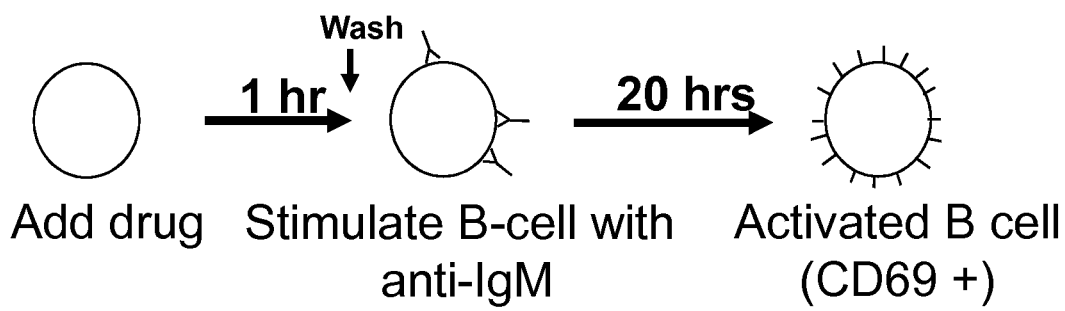
FIG. 6A presents an experimental scheme that illustrates a brief in vitro exposure of B cells to Compound 1.
Figure 6B:
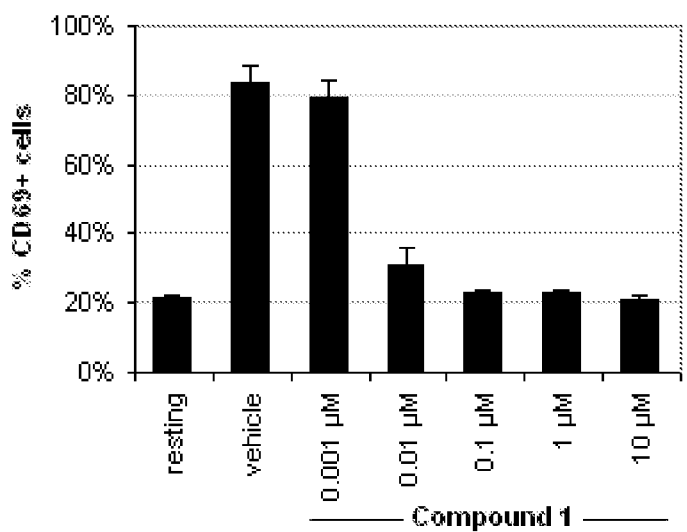
FIG. 6B presents an illustrative bar graph showing brief exposure to Compound 1 in vitro is sufficient to inhibit B cell activation in normal human B cells. B cells were purified from blood from healthy donors by negative selecting using the RosetteSep Human B cell enrichment cocktail. Cells were plated in growth media and indicated concentrations of Compound 1 were added. After incubation for 1 hour at 37° C., cells were washed three times using an 8-fold dilution in growth media for each wash. Cells were then stimulated with IgM F(ab')2 for 18 hours at 37° C., stained with anti-CD69-PE antibody and analyzed by flow cytometry. This protocol mimics the predicted exposure of cells to Compound 1 in vivo and demonstrates that inhibition of B cells is sustained despite washing out of Compound 1.
Figure 8:
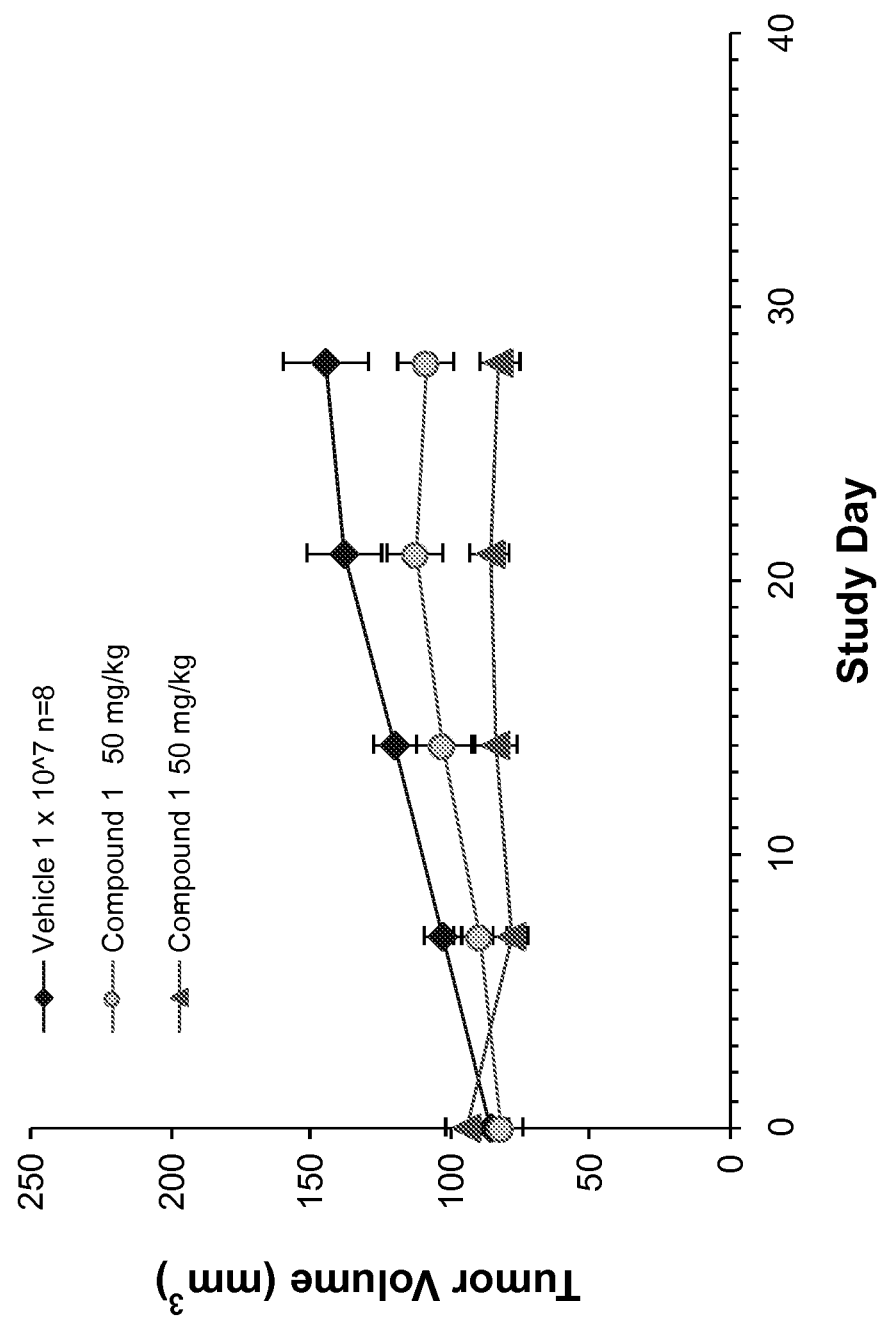
FIG. 8 shows efficacy of HER4 inhibitor Compound 1 in MDA-MB-453 grown as a xenograft in nude mice.
Figure 9A:
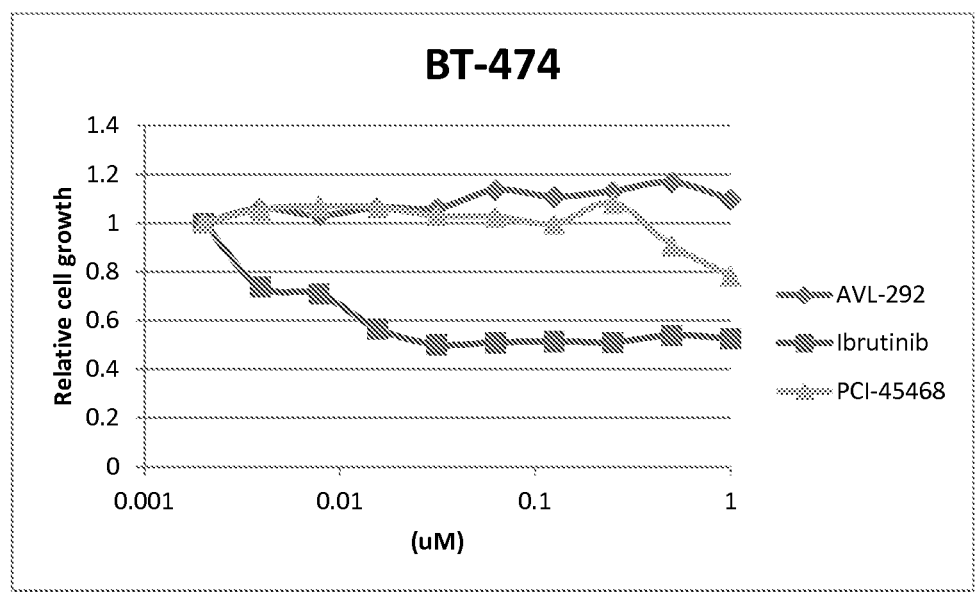
FIG. 9A-FIG. 9D: exemplifies the effects of ibrutinib on relative cell growth (FIG. 9A) BT-474 cells—ibrutinib, AVL-292 and PCI-45468.
Figure 9B:
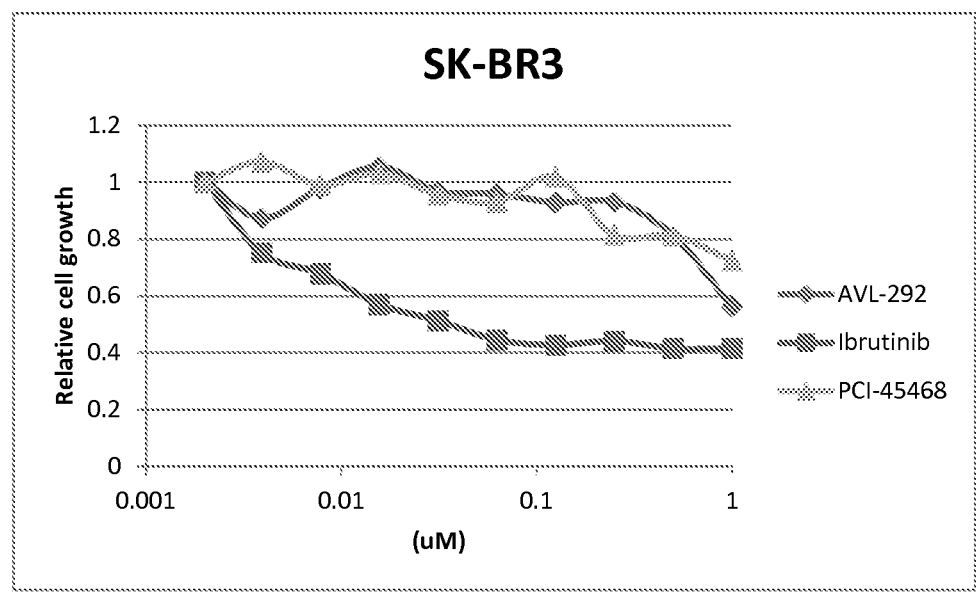
Figure 9C:
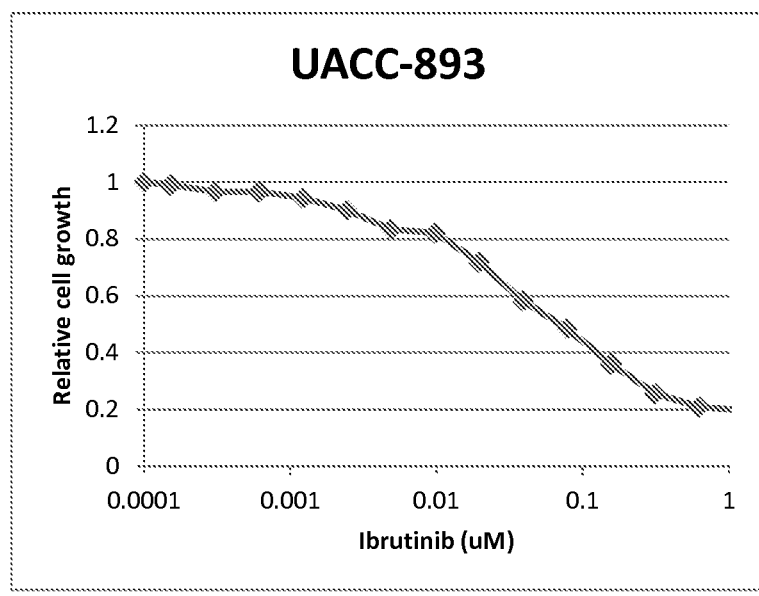
Figure 9D:
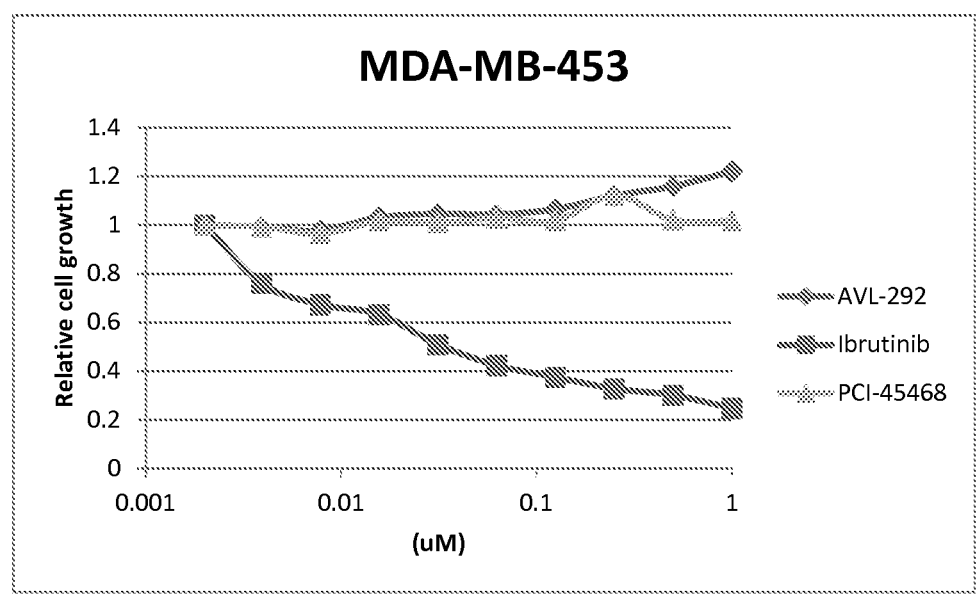

Brief exposure to Compound 1 in vitro is sufficient to inhibit B cell activation in normal human B cells (FIG. 6). This protocol mimics the predicted exposure of cells to Compound 1 in vivo and demonstrates that inhibition of B cells is sustained despite washing out of Compound 1.

B cells were purified from blood from healthy donors by negative selecting using the RosetteSep Human B cell enrichment cocktail. Cells were plated in growth media (10% RPMI+10% fetal calf serum) and indicated concentrations of Compound 1 were added. After incubation for 1 hour at 37° C., cells were washed three times using an 8-fold dilution in growth media for each wash. Cells were then stimulated with 10 ug/ml of IgM F(ab')2 for 18 hours at 37° C. Cells were then stained with anti-CD69-PE antibody and analyzed by flow cytometry using standard conditions.

Example 7: Optimizing the Therapeutic Index of Kinase Inhibitors

Given that kinase inhibitors described above will have both reversible and irreversible activities, we select their in vivo properties of absorption, distribution, metabolism and excretion (ADME) in order to optimize the therapeutic index. Specifically, rapidly cleared compounds are expected to cause only brief inhibition of reversibly inhibited targets while maintaining sustained inhibition of irreversibly inhibited targets. Depending on the degree to which sustained inhibition of particular targets results in therapeutic effects or toxicities, we identify compounds with an optimal combination of in vitro selectivity profiles and in vivo ADME properties.

Example 8: Administration of Btk Inhibitor to a Mouse Model for Colon Cancer Under the skin of a mouse is implanted a colon cancer xenograft. On a daily basis, administration of Compound 1 is effected by intravenous administration at a level of 1 microgram per gram of mouse weight. The size of the tumor xenograft is also monitored daily. Success is determined by survival of the mouse for a period of time statistically longer than survival of a mouse administered with vehicle on the same dosing schedule.

Example 9: Pancreatic Cancer Clinical Trial

Length of Study
  8 months [length of time from FPV to LPV]
Objectives
  The primary objective of this study will be to determine the objective response rate (ORR) for Btk inhibitors when administered every 2 weeks to patients with adenocarcinoma of the pancreas. The secondary objectives of this study will be to measure time-to-event variables including: time to objective tumor response for responding patients (TtOR), duration of response for responding patients, time to treatment failure (TtTF), time to progressive disease (TtPD), progression-free survival (PFS), overall survival (OS); the toxicities of therapy.
Study Design
  The study will be a multi-center, double-blind, randomized, placebo-controlled Phase 2 study. Tumor assessments will be repeated every 4 cycles (approximately 8 weeks). Patients will receive study therapy for 12 treatments, or until tumor progression was documented, unacceptable toxicity was experienced, the patient withdrew consent, or the patient is unable to fulfill the responsibilities of study participation as determined by the treating physician or the qualified investigator. After study discontinuation, patients who have not progressed will have tumor assessments performed approximately every 8 weeks until disease progression. Once patients have disease progression, patients will enter a post-study follow-up period, and will be followed every 12 weeks for 24 months for overall survival. Patients will also be followed for ongoing or any new toxicities.

Diagnosis and Main Criteria for Inclusion:

Male and females ≥18 years of age will be eligible for this study if they are diagnosed with adenocarcinoma of the pancrease. Patients must have had as their initial presentation pancreatic metastasis without evidence of pulmonary metastasis.

Main inclusion criteria will include: histologically proven adenocarcinoma; performance Status of 0 or 1 on the Eastern Cooperative Oncology Group (ECOG) scale; a complete history and physical, chest x-ray, CT scan of abdomen and pelvis; barium enema, or colonoscopy. Patients with pain will be requires to have had their pain stabilized for 1 week prior to commencing therapy. Patients requiring opioids for pain control will be required to have been on a fixed analgesic regimen aimed to provide adequate pain control with no more than three breakthrough (supplemental) doses of analgesics per day to control pain. Patients will be requires to demonstrate adequate bone marrow reserve (i.e. Neutrophil count ≥1.5×109 cells/L; Platelets ≥100×109 cells/L). Patients will be required to have negative tumor markers for alpha-fetoprotein (AFP) and monoclonal antichorionic gonadotropin (β-subunit) (βHCG). Patients will be required to demonstrate at least one unidimensionally measurable lesion, meeting Response Evaluation Criteria in Solid Tumors (RECIST). Patient will also be required to have an estimated life expectancy of at least 12 weeks.

Main exclusion criteria will include: prior chemotherapy; pregnancy or breastfeeding; inability or unwillingness to take folic acid, vitamin B12 supplementation, or dexamethasone.

Study Drug, Dose, and Mode of Administration

Btk inhibitor of Formula VII dosage will be 500 mg/m$^2$ and will be given as a 10-minute infusion on Day 1 of each 14-day cycle. Folic acid and vitamin B12 supplementation, and dexamethasone (or equivalent corticosteroid) prophylaxis will also be administered.

Variables

Efficacy: Tumor response rate will be defined as the number of patients with documented partial response (PR) or complete response (CR) divided by the number of patients qualified for tumor response analysis. Time-to-event analyses will be performed on the observed distributions of time to objective progressive disease, progression-free survival (PFS), time to treatment failure (TtTF), and overall survival (OS) using the Kaplan-Meier (K-M) method. All patients with best overall response of CR or PR will be analyzed for response duration by using the K-M method.

Safety: Safety analyses will include adverse event (AE) rates, serious AEs, vital signs, laboratory data, blood transfusions required, and deaths. Toxicities using laboratory and nonlaboratory adverse events will be evaluated using the common terminology criteria for adverse events (CTCAE, version 3.0).

Evaluation Methods

Statistical: The primary analysis will be to estimate the objective best overall response rate and its 95% confidence interval (CI). Medians for each of the time-to-event endpoints, and time-to-event variables will be estimated using the K-M method. All estimates of treatment effects will be conducted at a two-sided alpha level of 0.05, and CI for all parameters will be estimated were to be constructed using a 95% level.

Example 10: Breast Cancer Clinical Trial

Length of Study 6 months

Objectives

The primary objective of this study will be to determine the objective response rate (ORR) for Btk inhibitors when administered every 2 weeks to patients with breast cancer. The secondary objectives of this study will be to measure time-to-event variables including: time to objective tumor response for responding patients (TtOR), duration of response for responding patients, time to treatment failure (TtTF), time to progressive disease (TtPD), progression-free survival (PFS), overall survival (OS); the toxicities of therapy.

Study Design

The study will be a multi-center, double-blind, randomized, placebo-controlled Phase 2 study. Tumor assessments will be repeated every 4 cycles (approximately 6 weeks). Patients will receive study therapy for 12 treatments, or until tumor progression was documented, unacceptable toxicity was experienced, the patient withdrew consent, or the patient is unable to fulfill the responsibilities of study participation as determined by the treating physician or the qualified investigator. After study discontinuation, patients who have not progressed will have tumor assessments performed approximately every 6 weeks until disease progression. Once patients have disease progression, patients will enter a post-study follow-up period, and will be followed every 12 weeks for 24 months for overall survival. Patients will also be followed for ongoing or any new toxicities.

Diagnosis and Main Criteria for Inclusion:

Female patients aged 18 years or older

Histologically-confirmed ER-negative, progesterone receptor (PgR)-positive or PgR-negative, metastatic breast cancer Cancer not life-threatening No previous endocrine or cytotoxic treatment for metastatic breast cancer.

Study Drug, Dose, and Mode of Administration

Btk inhibitor of Formula VII dosage will be 1000 mg/m$^2$ and will be given as a 60-minute infusion on Day 1 of each cycle. Folic acid and vitamin B12 supplementation, and dexamethasone (or equivalent corticosteroid) prophylaxis will also be administered.

Variables

Efficacy: Tumor response rate will be defined as the number of patients with documented partial response (PR) or complete response (CR) divided by the number of patients qualified for tumor response analysis. Time-to-event analyses will be performed on the observed distributions of time to objective progressive disease, progression-free survival (PFS), time to treatment failure (TtTF), and overall survival (OS) using the Kaplan-Meier (K-M) method. All patients with best overall response of CR or PR will be analyzed for response duration by using the K-M method.

Safety: Safety analyses will include adverse event (AE) rates, serious AEs, vital signs, laboratory data, blood transfusions required, and deaths. Toxicities using laboratory and nonlaboratory adverse events will be evaluated using the common terminology criteria for adverse events (CTCAE, version 3.0).

Evaluation Methods

Statistical: The primary analysis will be to estimate the objective best overall response rate and its 95% confidence interval (CI). Medians for each of the time-to-event endpoints, and time-to-event variables will be estimated using the K-M method. All estimates of treatment effects will be conducted at a two-sided alpha level of 0.05, and CI for all parameters will be estimated were to be constructed using a 95% level.

Example 11: Breast Cancer Clinical Trial

An MDA-MB-453 breast cancer xenograft was implanted under the skin of a nude mouse. On a daily basis, administration of Compound 1 was effected by intravenous administration at a level of (a) 50 mg/kg of mouse weight, or (b) 5 mg/kg of mouse weight. The volume of the tumor xenograft was monitored daily.

Example 12: Assays and Reagents

All the cells are purchased from ATCC and cultured as indicated from the source; Antibodies are from Cell Signaling and Sata Cluz Biotechnologies; Western blotting reagents from Life Technology (Invitrogen)

Cell proliferation assay with alamar blue: cells are plated at 10,000 cells/well in 100 uL. After 3 day incubation at 370 C in 5% CO2 incubator, alamar blue (Invitrogen 1:10) is added into each well and incubated for another 2.5-3 h. Read the plate at Ex/Em-545/590 nm.

Immunoblotting: Cells are washed once with cold PBS and lysed in 1x sample buffer (Invitrogen). The whole cell lysate is boiled, sonicated, and then loaded into 4-15% gradient SDS-PAGE gel. The proteins are transferred to PVDF membrane. After probing with antibodies, the detection is conducted using Odyssey spectrometer (Li-Cor).

Results

Breast cancer lines (BT-474, SK-BR3, MDA-MB-453 and UACC-893) which are HER2 amplified are sensitive to the growth inhibitory effect of ibrutini (see e.g., FIGS. 9a-9d).

Figure 10A:
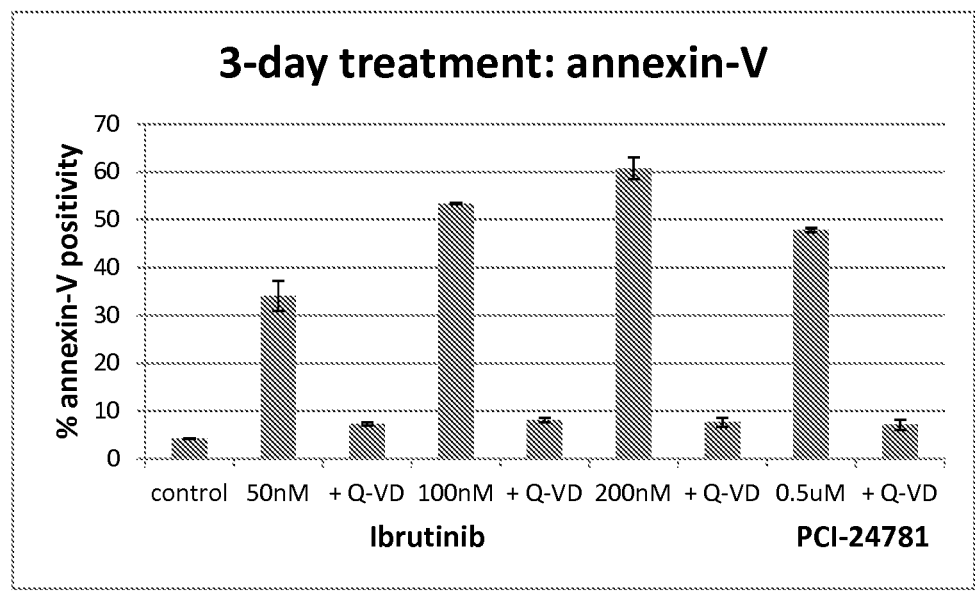
FIG. 10A-FIG. 10B: exemplifies the effects of ibrutinib and PCI-24781 on BT-474 cells (FIG. 10A) 3-day treatment: annexin-V.
Figure 10B:
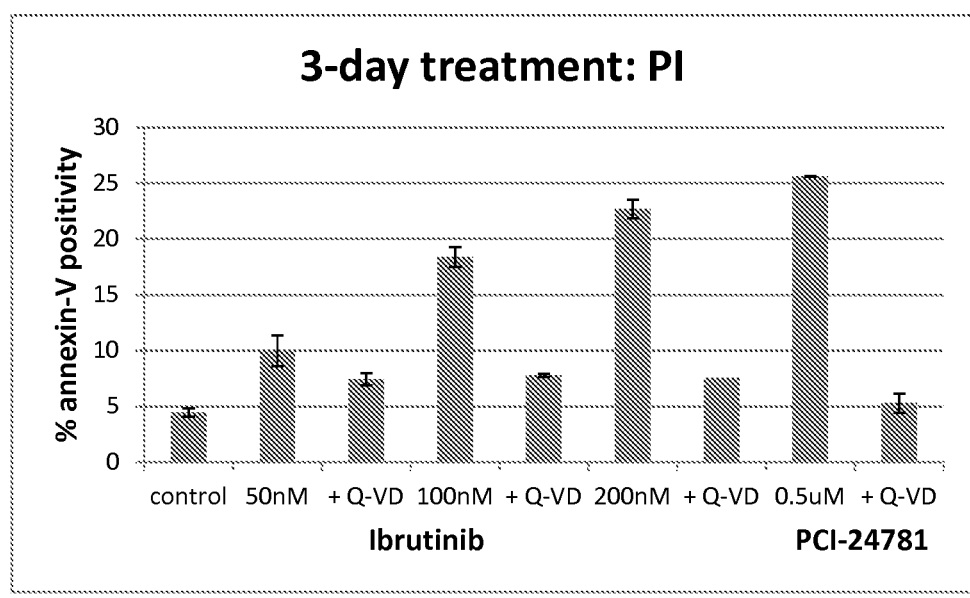

Ibrutinib induces apoptosis in BT-474 cells (see e.g., FIGS. 10a and 10b).

Figure 11:
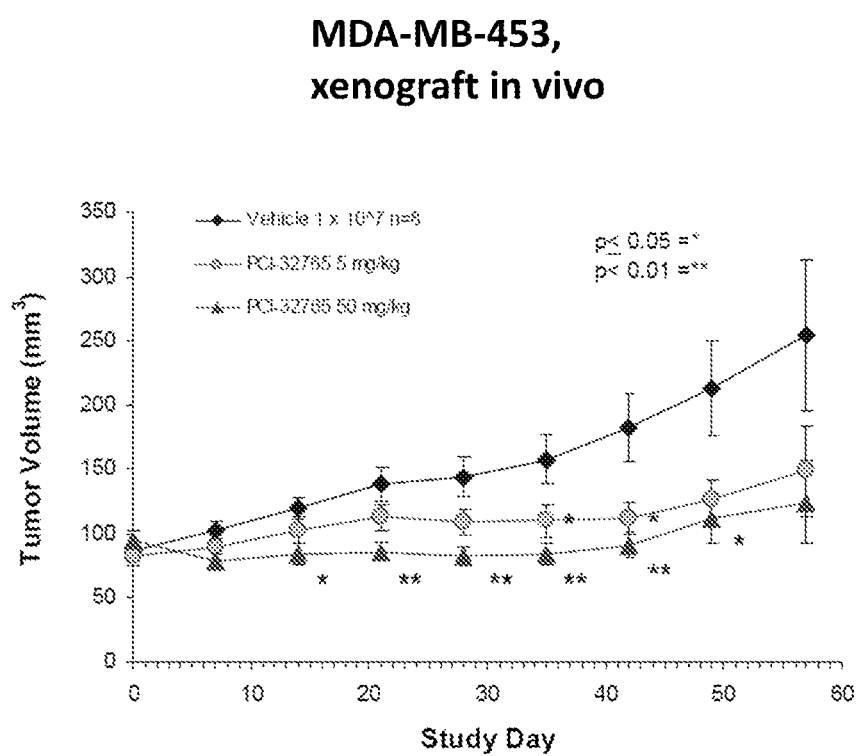
FIG. 11: exemplifies the effects of ibrutinib on tumor volume of a MDA-MB-453 mouse xenograft.

Ibrutinib inhibits tumor growth in a mouse MDA-MB-453 xenograft (see e.g. FIG. 11).

Figure 12:
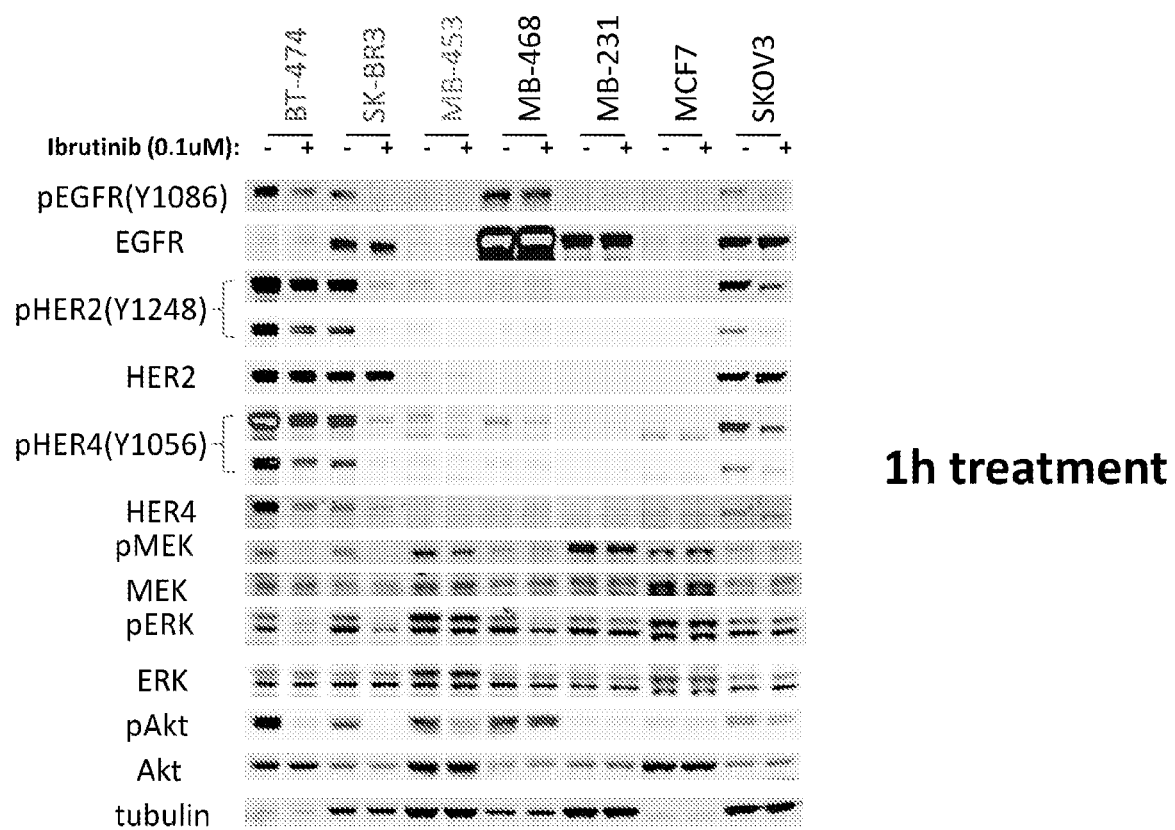
FIG. 12: exemplifies gene expression levels of multiple cancer cell lines with (+) or without (−) administration of 0.1 uM ibrutinib.
Figure 13:
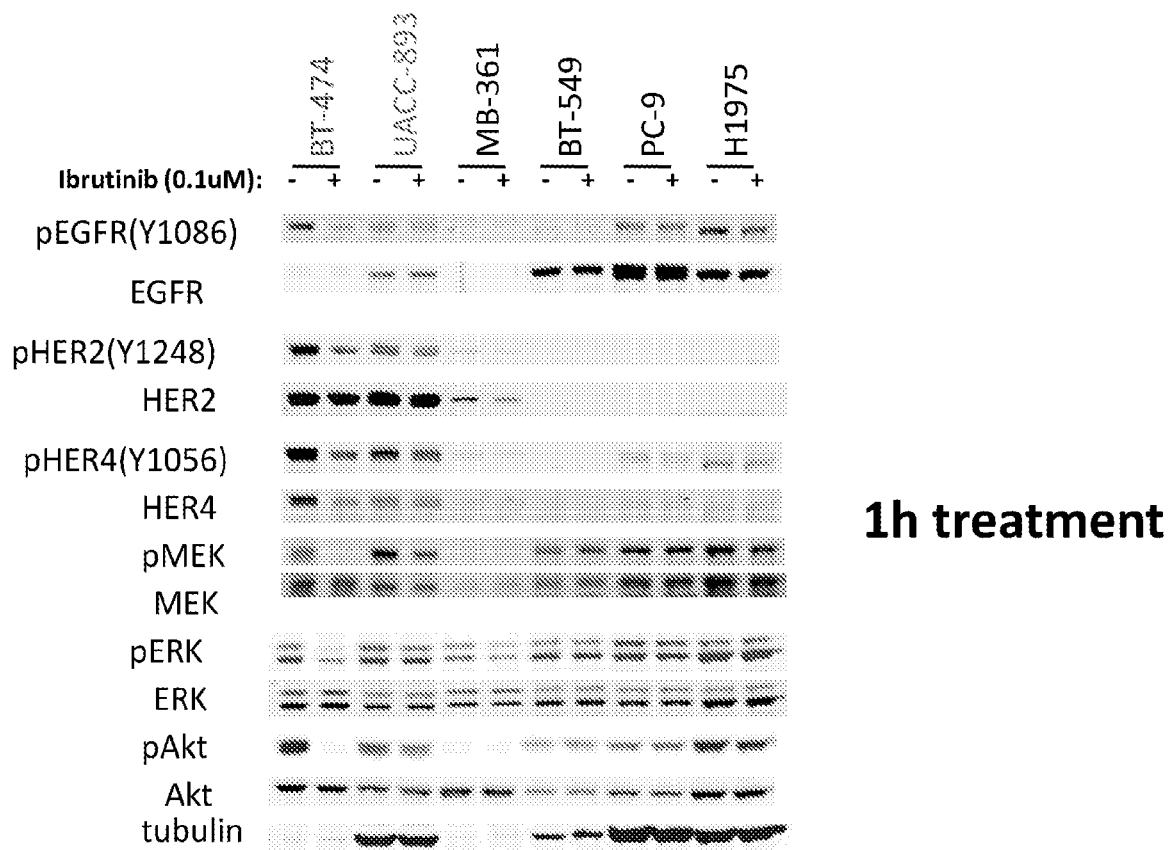
FIG. 13: exemplifies gene expression levels of multiple cancer cell lines with (+) or without (−) administration of 0.1 uM ibrutinib.

Breast cancer lines that are sensitive to ibrutinib are HER2/4-amplified (see e.g., FIGS. 12 and 13).

Figure 14:
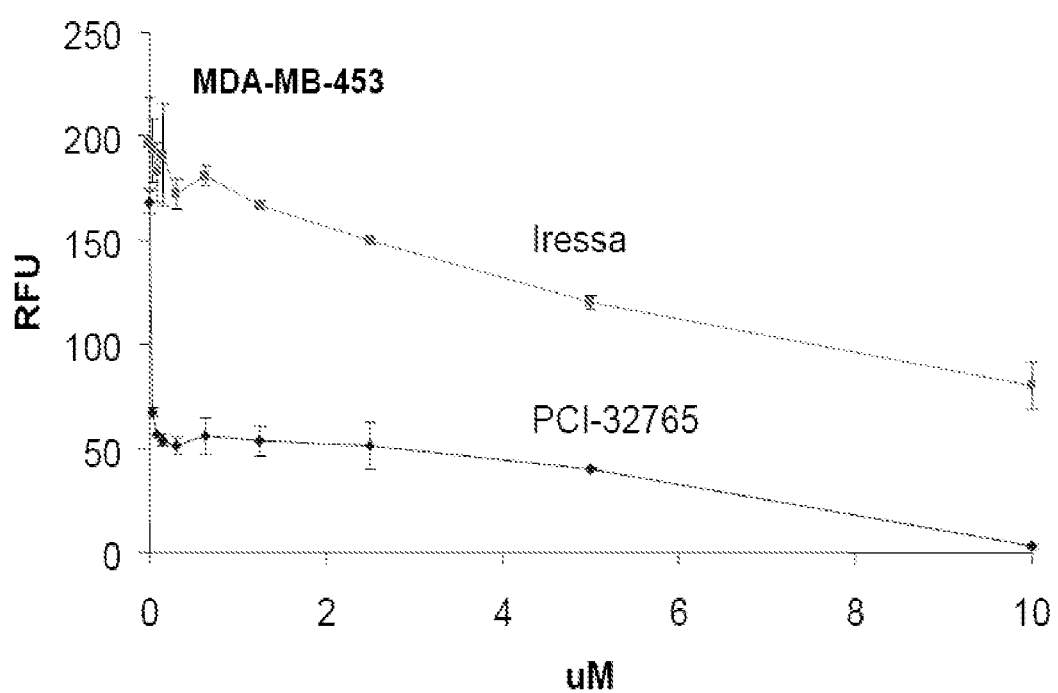
FIG. 14: is an exemplary comparison of the effects of gefitinib and ibrutinib on MDA-MB-453 cells.
Figure 15:
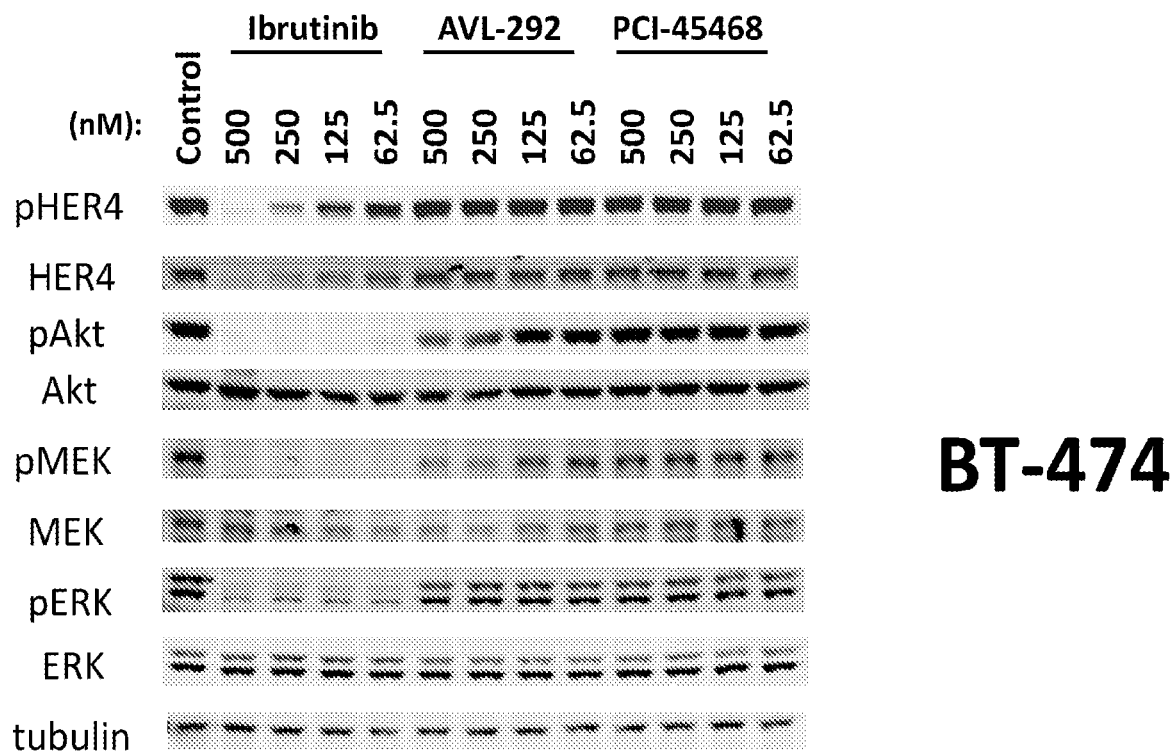
FIG. 15: exemplifies the effects of ibrutinib, AVL-292 and PCI-45468 on HER2 and HER activiation and downstream pathways in BT-474 cells.
Figure 16A:
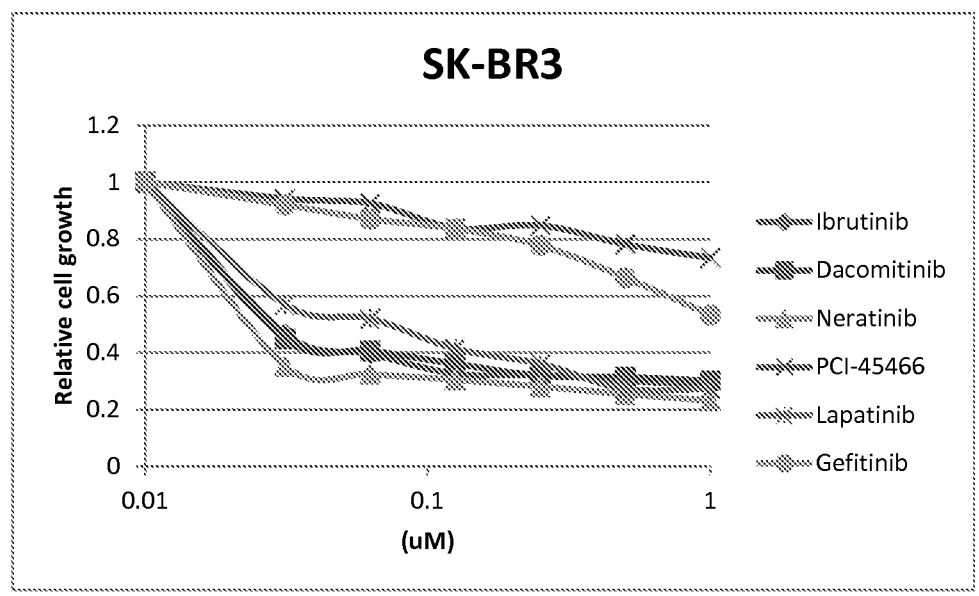
FIG. 16A-FIG. 16B: exemplifies the effects of ibrutinib, dacomitinib, neratinib, PCI-45466, lapatinib, and gefitinib on relative cell growth of SK-BR3 cells (FIG. 16A) and MDA-MB-453 cells (FIG. 16B).
Figure 16B:
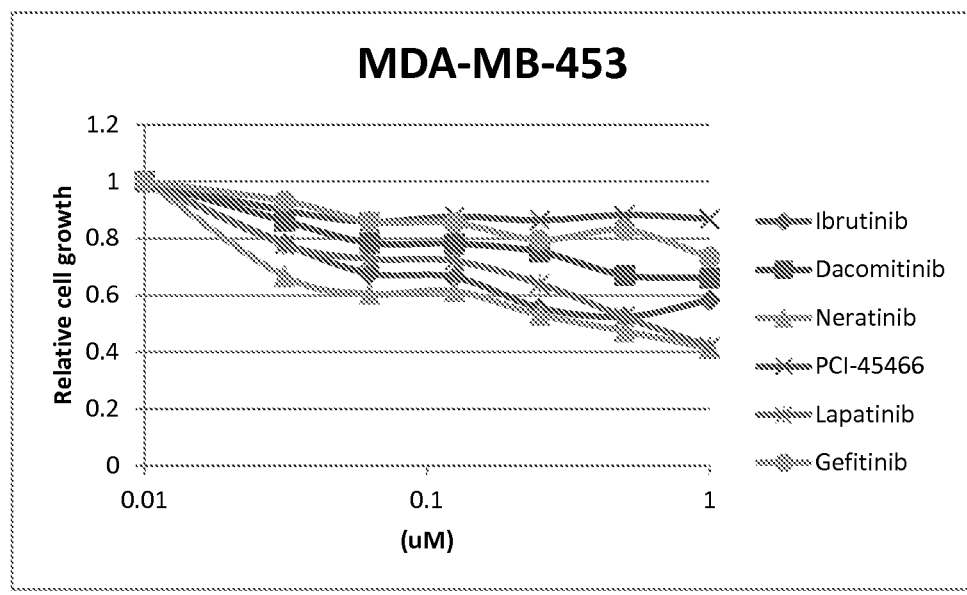
Figure 17A:
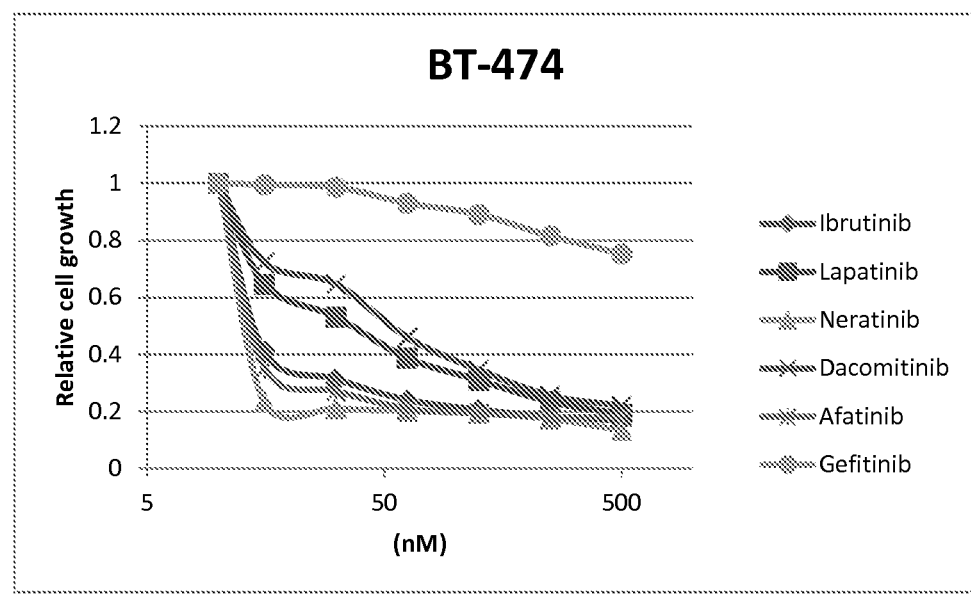
FIG. 17A-FIG. 17C: exemplifies the effects of ibrutinib, lapatinib, neratinib, dacomitinib, afatinib, and gefitinib on relative cell growth of BT-474 cells (FIG. 17A), SK-BR3 cells (FIG. 17B) and MDA-MB-453 cells (FIG. 17C).
Figure 17B:
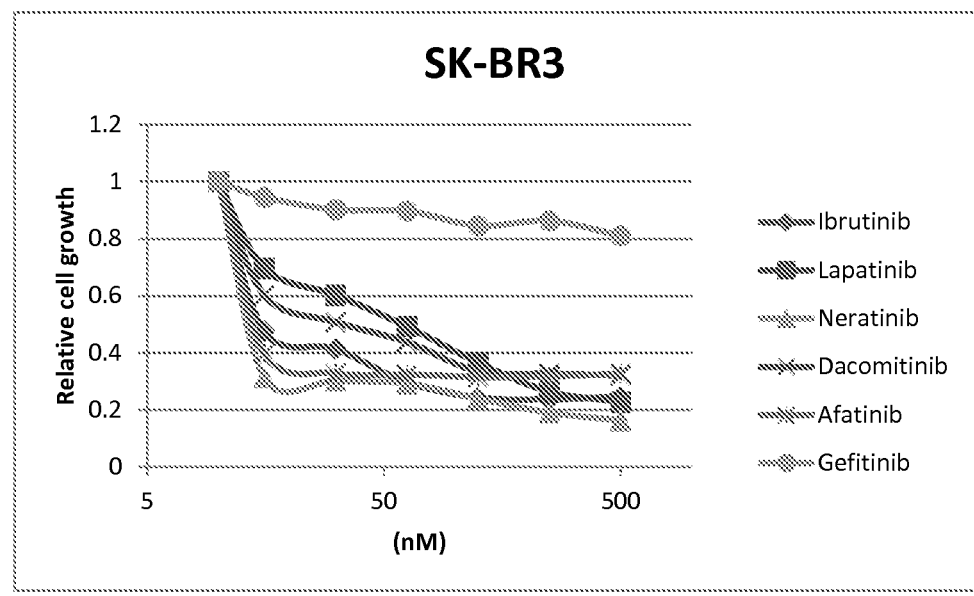
Figure 17C:
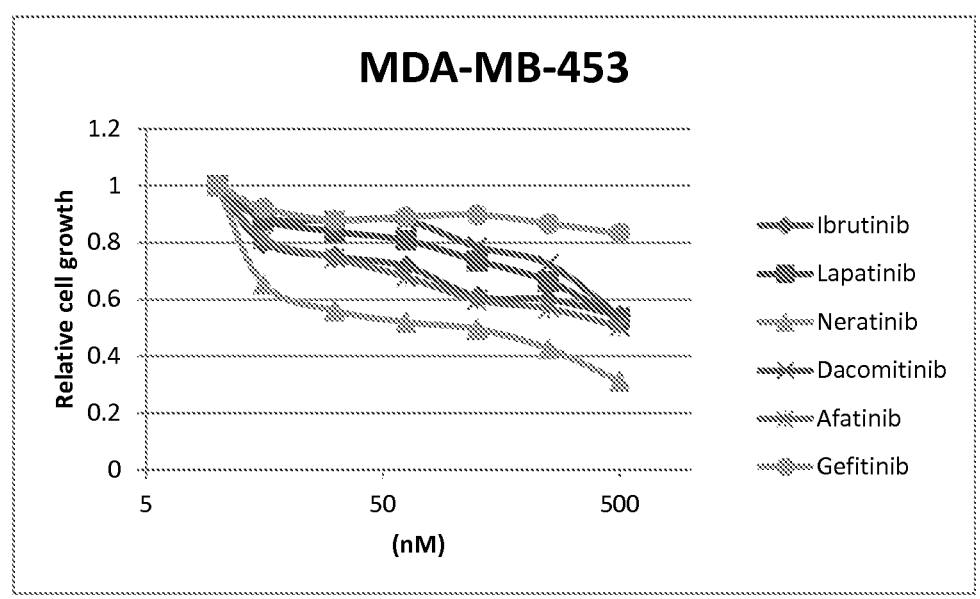

Ibrutinib is more potent than gefitinib in inhibiting MDA-MB-453 cell growth (see e.g., FIG. 14).

Ibrutinib shows similar activity with lapatinib, neratinib and dacomitinib (see e.g., FIGS. 16a, 16b, 17a, 17b, and 17c).

What is claimed is:

1. A method for treating HER2 amplified breast cancer in an individual in need thereof comprising administering to the individual in need thereof a composition comprising a therapeutically-effective amount of a compound of Formula (C1) having the structure:

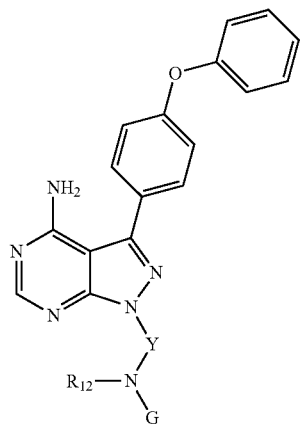

Formula (C1)

or a pharmaceutically acceptable salt thereof, wherein:
Y is selected from alkyl, heteroalkyl, aryl, heteroaryl, alkylaryl, alkylheteroaryl, and alkylheterocycloalkyl;
$R_{12}$ is H or lower alkyl; or
Y and $R_{12}$ taken together form a 4-, 5-, or 6-membered heterocyclic ring;
G is

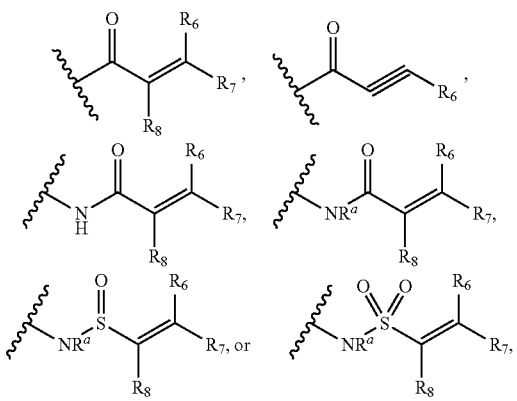

wherein $R^a$ is H, alkyl, or cycloalkyl; and either
(i) $R_7$ and $R_8$ are H; and
$R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl); or (ii) $R_6$ and $R_8$ are H; and $R_7$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl); or (iii) $R_7$ and $R_8$ taken together form a bond; and $R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

2. The method of claim 1, wherein:

Y and $R_{12}$ taken together form a 4-, 5-, or 6-membered heterocyclic ring.

3. The method of claim 2, wherein $R_6$ and $R_8$ are H; and $R_7$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

4. The method of claim 3, wherein:

Y and $R_{12}$ taken together form a 6-membered heterocyclic ring.

5. The method of claim 1, wherein the compound is selected from:

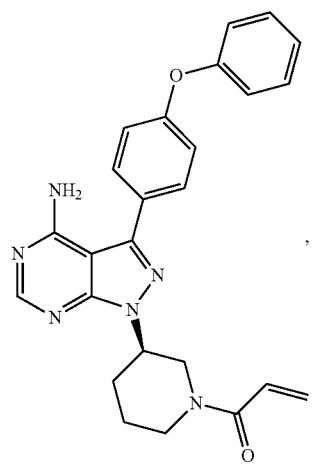

,

-continued

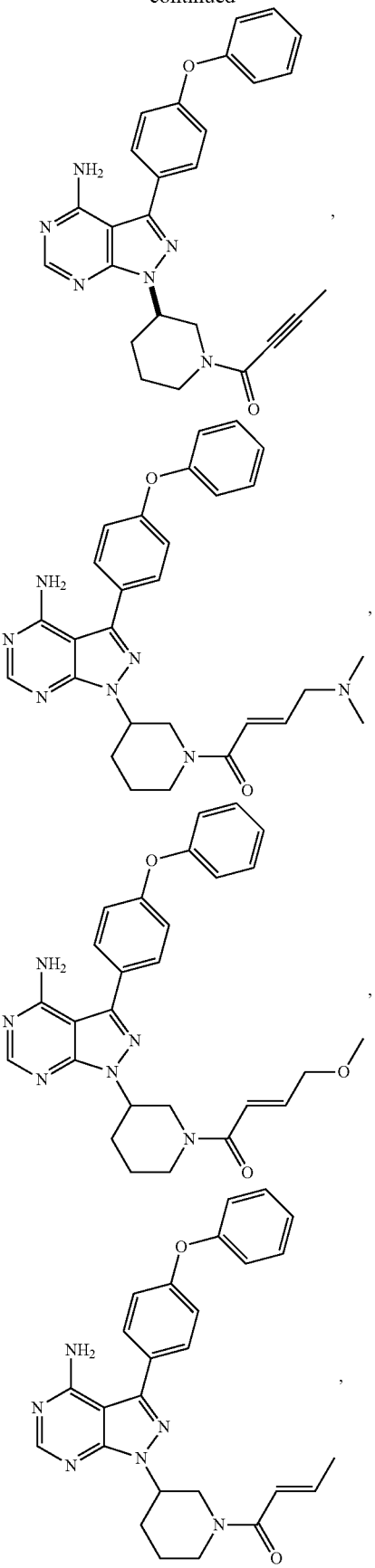

145
-continued
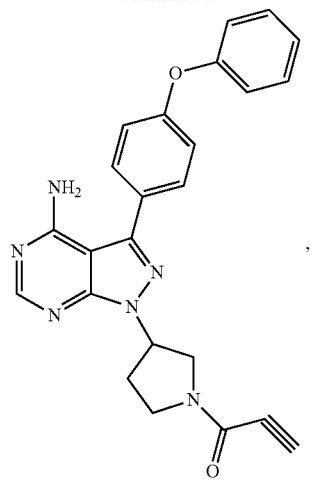
,
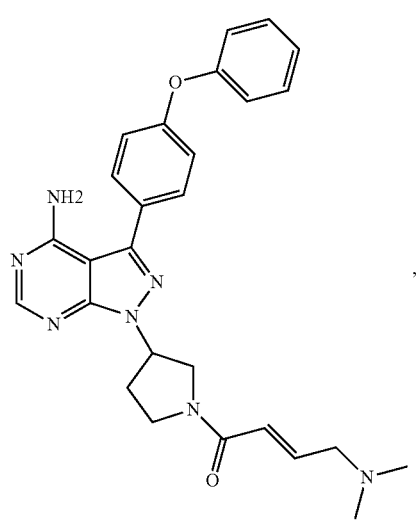
,
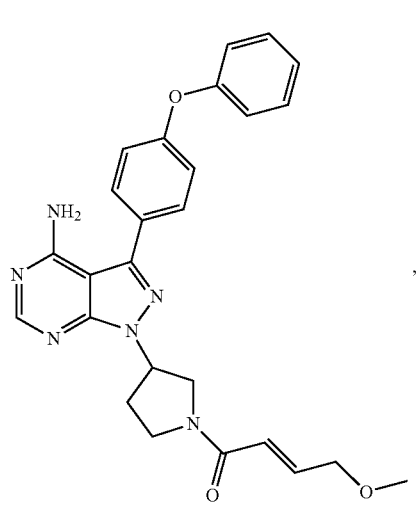
,
146
-continued
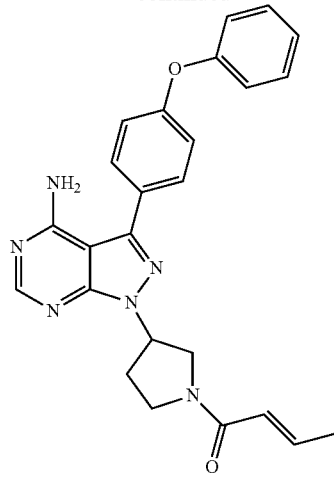
,
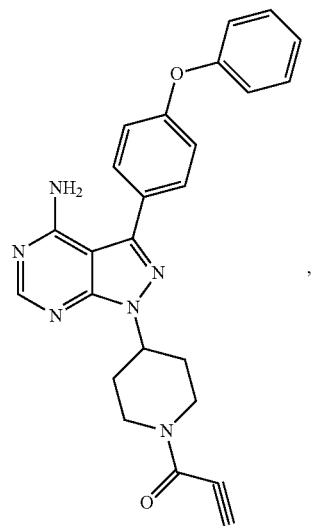
,
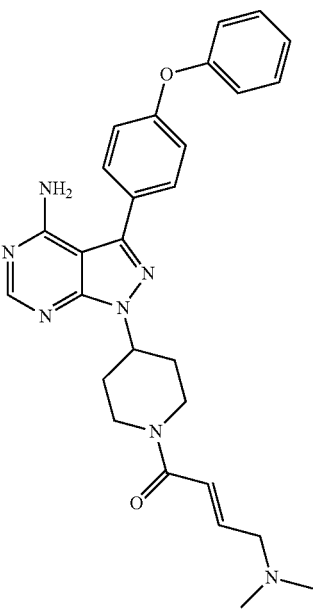
, 147
-continued
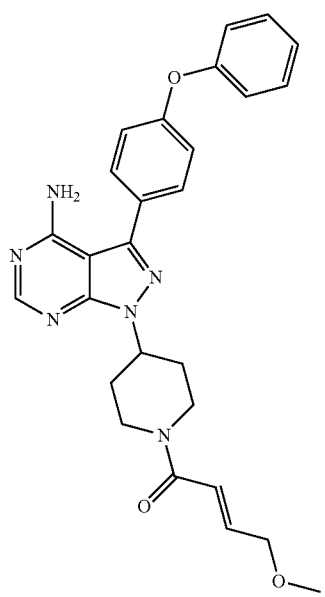
148
-continued
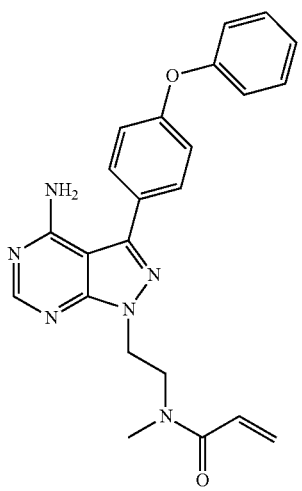
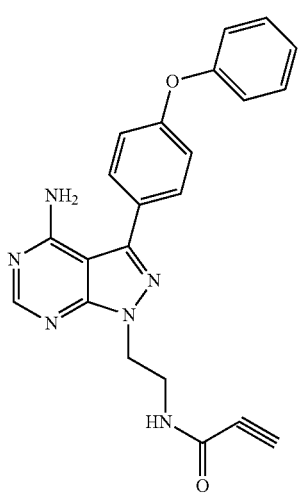
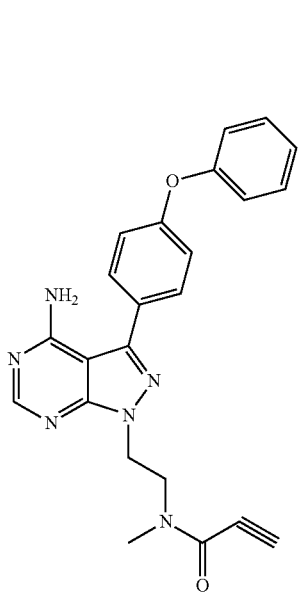

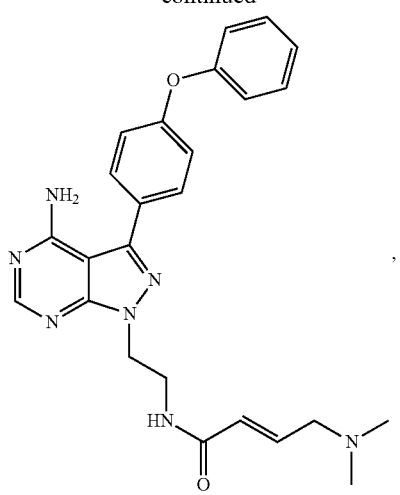

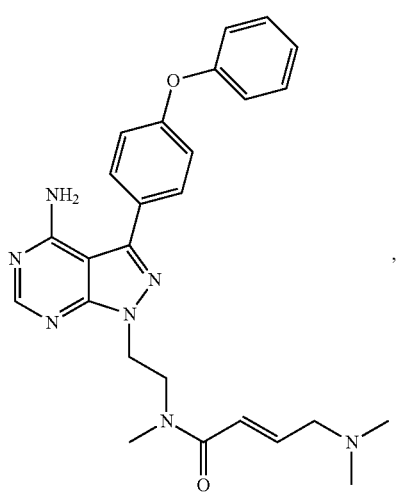

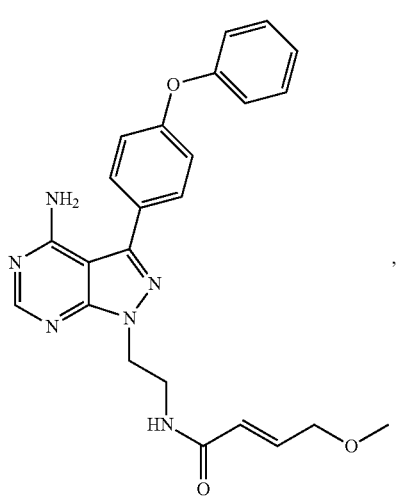

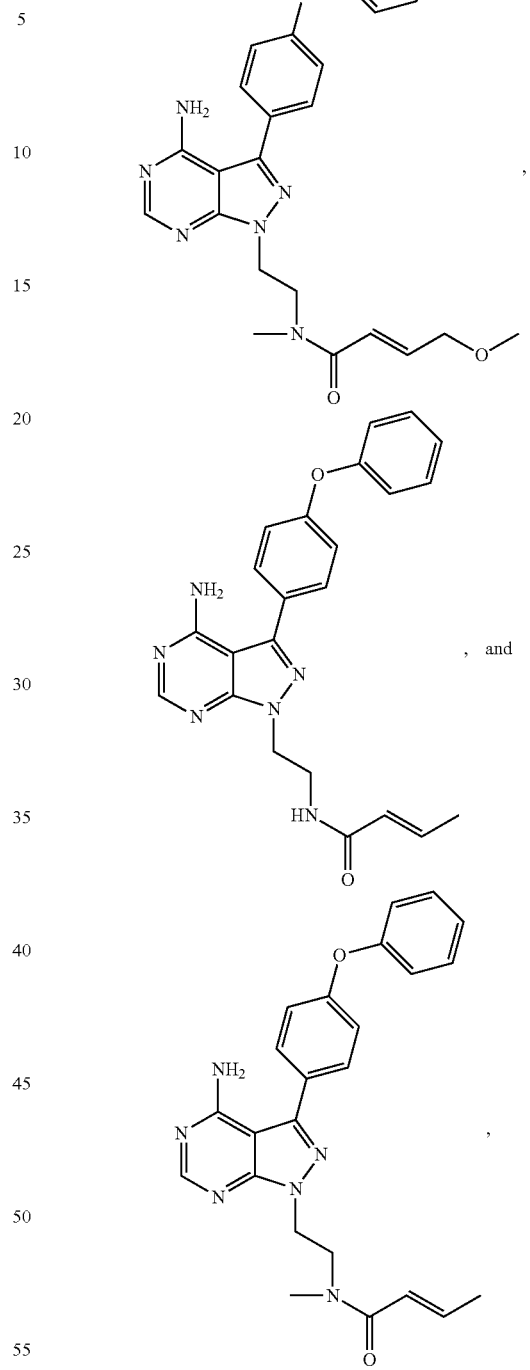

or a pharmaceutically acceptable salt thereof.

6. The method of claim 1, further comprising administering an additional therapeutic agent selected from: trastuzumab, paclitaxel, doxorubicin, cyclophosphamide, and cisplatin.

7. The method of claim 1, further comprising administering trastuzumab.

8. A method for treating HER2 amplified cancer in an individual in need thereof, wherein the HER2 amplified cancer is selected from pancreatic cancer and non-small-cell lung carcinoma, the method comprising administering to the individual in need thereof a composition comprising a therapeutically-effective amount of a compound of Formula (C1) having the structure:

Formula (C1)

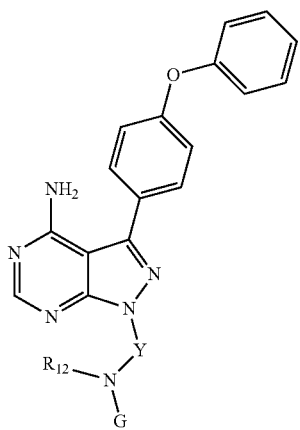

or a pharmaceutically acceptable salt thereof,
wherein:
Y is selected from alkyl, heteroalkyl, aryl, heteroaryl, alkylaryl, alkylheteroaryl, and alkylheterocycloalkyl;
$R_{12}$ is H or lower alkyl; or
Y and $R_{12}$ taken together form a 4-, 5-, or 6-membered heterocyclic ring;
G is

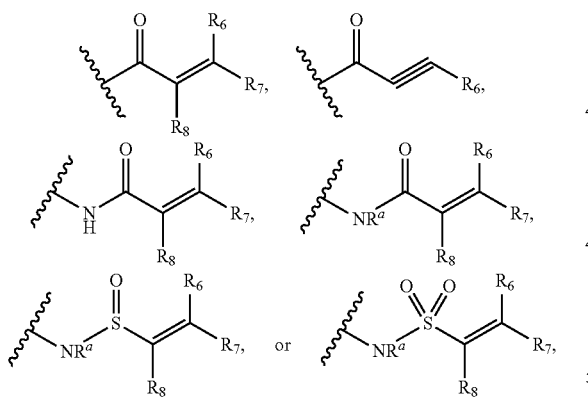

wherein $R^a$ is H, alkyl, or cycloalkyl; and either
(i) $R_7$ and $R_8$ are H; and
$R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl (aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl); or
(ii) $R_6$ and $R_8$ are H; and
$R_7$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl (aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl); or
(iii) $R_7$ and $R_8$ taken together form a bond; and
$R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl (aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

9. The method of claim 8, wherein:
Y and $R_{12}$ taken together form a 4-, 5-, or 6-membered heterocyclic ring.

10. The method of claim 9, wherein
$R_6$ and $R_8$ are H; and
$R_7$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

11. The method of claim 9, wherein:
Y and $R_{12}$ taken together form a 6-membered heterocyclic ring;
$R_6$ and $R_8$ are H; and
$R_7$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

12. The method of claim 8, wherein the compound is

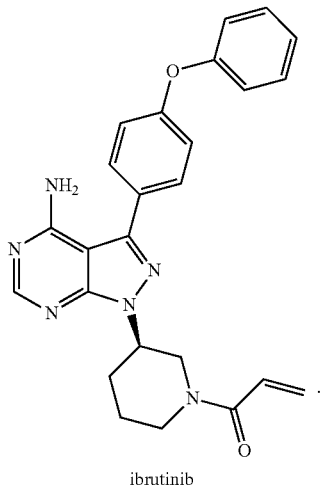 [SMILES: C=CC(=O)N1CCC[C@@H](n2nc(-c3ccc(Oc4ccccc4)cc3)c3c(N)ncnc32)C1]

ibrutinib

13. The method of claim 8, further comprising administering an additional therapeutic agent selected from: trastuzumab, paclitaxel, doxorubicin, cyclophosphamide, and cisplatin.

14. The method of claim 8, further comprising administering trastuzumab.

15. The method of claim 2, wherein $R_7$ and $R_8$ taken together form a bond; and $R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

16. The method of claim 9, wherein $R_7$ and $R_8$ taken together form a bond; and $R_6$ is H, $C_1$-$C_4$alkyl, $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, $C_3$-$C_6$cycloalkyl, $C_1$-$C_8$alkyl$C_3$-$C_6$cycloalkyl, aryl, $C_2$-$C_8$heterocycloalkyl, heteroaryl, $C_1$-$C_4$alkyl(aryl), $C_1$-$C_4$alkyl(heteroaryl), $C_1$-$C_8$alkylether, $C_1$-$C_8$alkylamide, or $C_1$-$C_4$alkyl($C_2$-$C_8$heterocycloalkyl).

17. The method of claim 8, wherein the compound is selected from

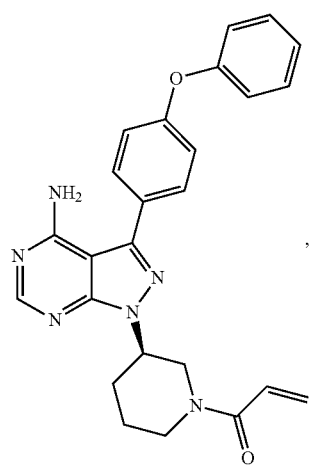

,

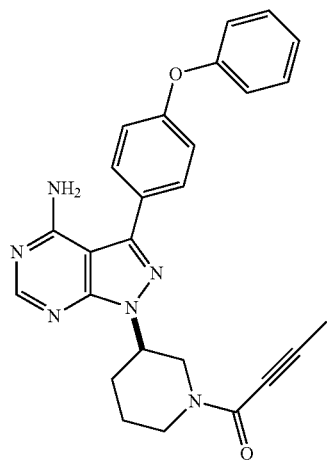

,

-continued

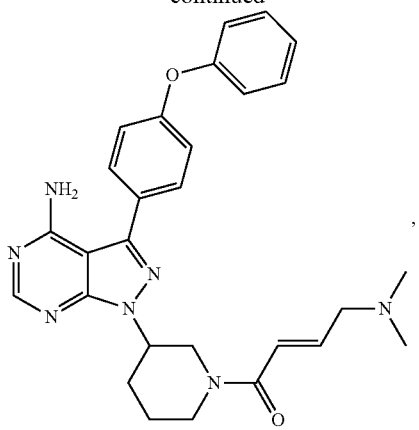

,

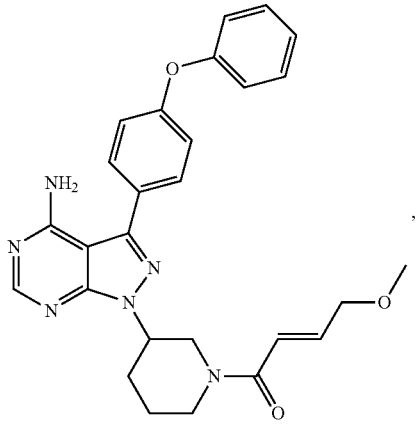

,

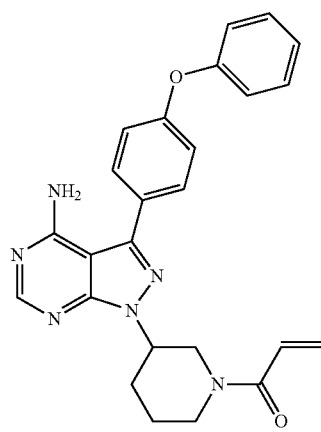

,

155
-continued
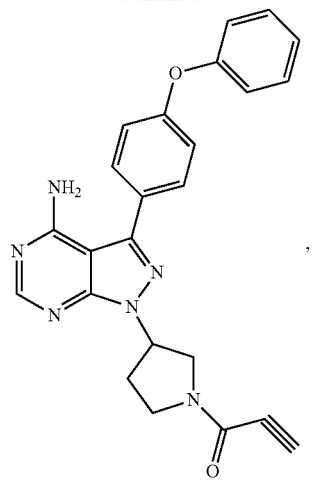
,
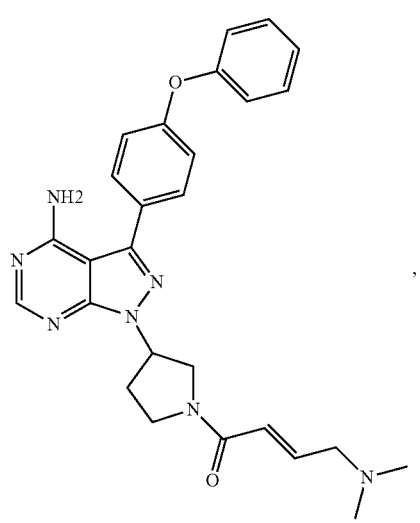
,
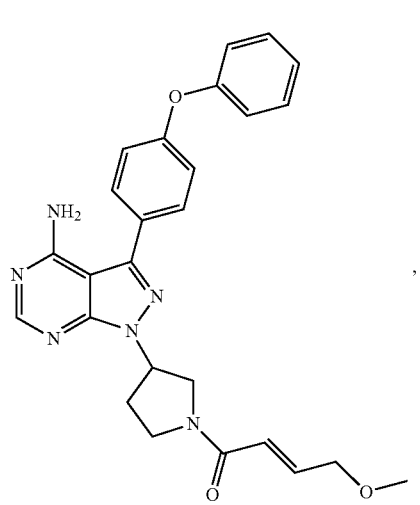
,
156
-continued
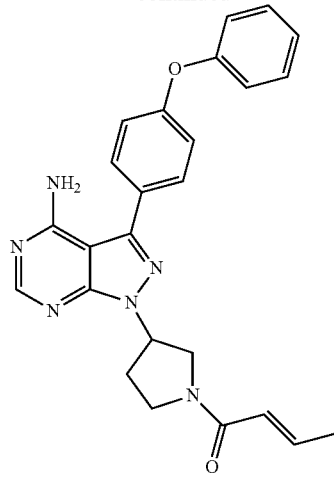
,
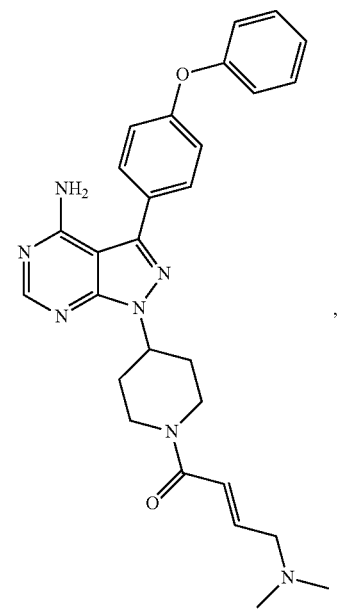
,

157
-continued
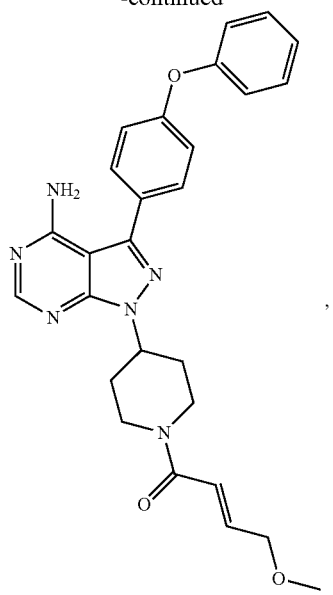
158
-continued
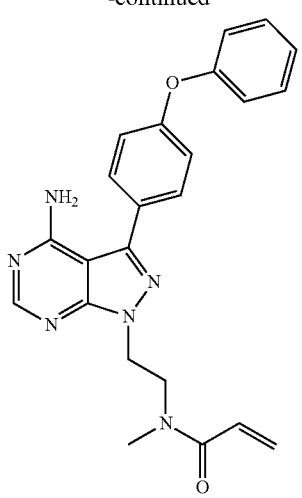
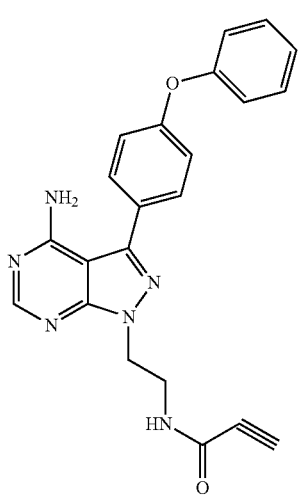
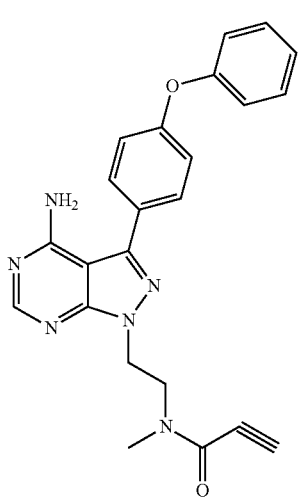

159
-continued
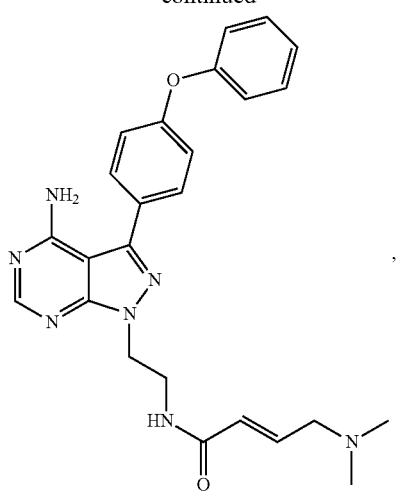
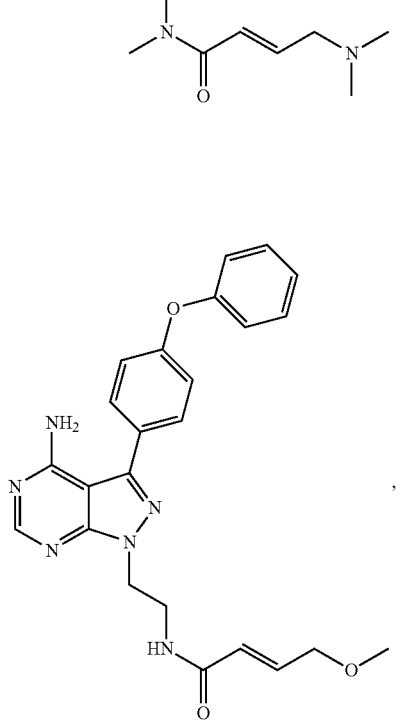
160
-continued
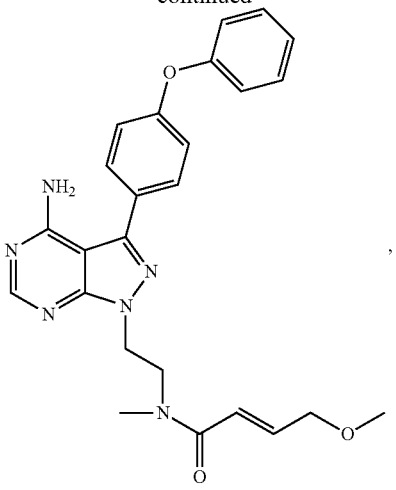
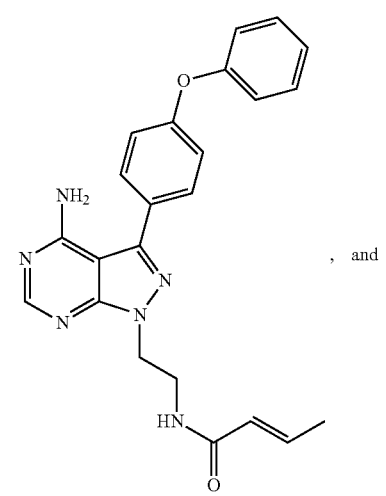
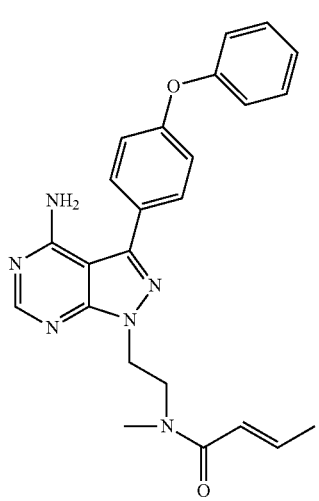
or a pharmaceutically acceptable salt thereof.
18. The method of claim 1, wherein Y is alkyl; or Y and $R_{12}$ taken together form a 4-, 5-, or 6-membered heterocyclic ring.
19. The method of claim 8, wherein Y is alkyl; or Y and $R_{12}$ taken together form a 4-, 5-, or 6-membered heterocyclic ring.

20. The method of claim 18, wherein G is
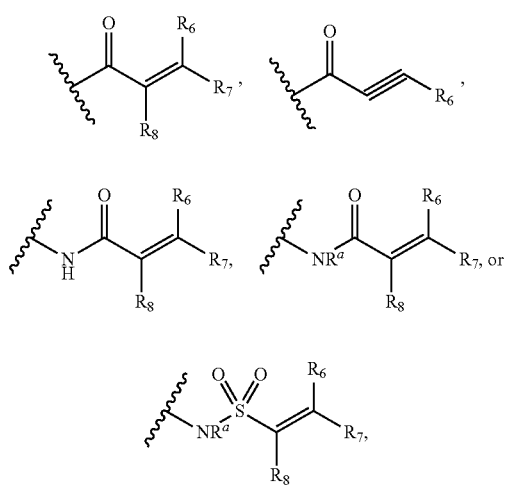
wherein $R^a$ is H or alkyl.
21. The method of claim 19, wherein G is
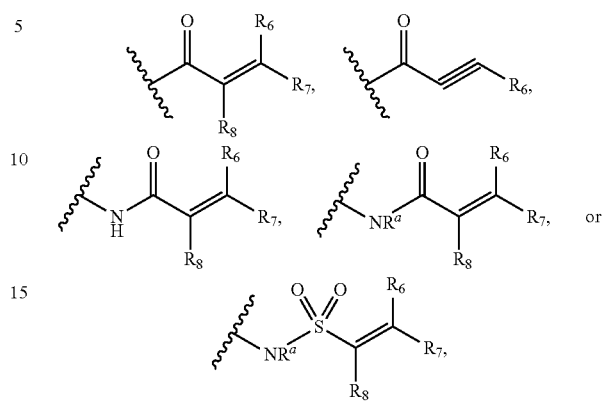
wherein $R^a$ is H or alkyl.
22. The method of claim 12, further comprising administering an additional therapeutic agent comprising paclitaxel or gemcitabine, or a combination thereof.
* * * * *

```
SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ala Val Leu Glu Ser Glu Glu Leu Tyr Ser Ser Ala Arg Gln
1               5                   10                  15

<210> SEQ ID NO 2
<211> LENGTH: 11
<212> TYPE: PRT
<213> ORGANISM: Homo sapiens

<400> SEQUENCE: 2

Ile Thr Glu Tyr Met Ala Asn Gly Cys Leu Leu
1               5                   10

<210> SEQ ID NO 3
<211> LENGTH: 11
<212> TYPE: PRT
<213> ORGANISM: Homo sapiens

<400> SEQUENCE: 3

Val Thr Glu Tyr Met Ala Arg Gly Cys Leu Leu
1               5                   10

<210> SEQ ID NO 4
<211> LENGTH: 11
```

<212> TYPE: PRT
<213> ORGANISM: Homo sapiens

<400> SEQUENCE: 4

Val Thr Glu Phe Met Glu Arg Gly Cys Leu Leu
1               5                   10

<210> SEQ ID NO 5
<211> LENGTH: 11
<212> TYPE: PRT
<213> ORGANISM: Homo sapiens

<400> SEQUENCE: 5

Val Thr Glu Phe Met Glu Asn Gly Cys Leu Leu
1               5                   10

<210> SEQ ID NO 6
<211> LENGTH: 11
<212> TYPE: PRT
<213> ORGANISM: Homo sapiens

<400> SEQUENCE: 6

Val Phe Glu Phe Met Glu His Gly Cys Leu Ser
1               5                   10

<210> SEQ ID NO 7
<211> LENGTH: 11
<212> TYPE: PRT
<213> ORGANISM: Homo sapiens

<400> SEQUENCE: 7

Ile Thr Gln Leu Met Pro Phe Gly Cys Leu Leu
1               5                   10

<210> SEQ ID NO 8
<211> LENGTH: 11
<212> TYPE: PRT
<213> ORGANISM: Homo sapiens

<400> SEQUENCE: 8

Val Thr Gln Leu Met Pro Tyr Gly Cys Leu Leu
1               5                   10

<210> SEQ ID NO 9
<211> LENGTH: 11
<212> TYPE: PRT
<213> ORGANISM: Homo sapiens

<400> SEQUENCE: 9

Val Thr Gln Leu Met Pro His Gly Cys Leu Leu
1               5                   10

<210> SEQ ID NO 10
<211> LENGTH: 11
<212> TYPE: PRT
<213> ORGANISM: Homo sapiens

<400> SEQUENCE: 10

Val Met Glu Tyr Leu Pro Ser Gly Cys Leu Arg
1               5                   10

<210> SEQ ID NO 11
<211> LENGTH: 11
<212> TYPE: PRT
<213> ORGANISM: Homo sapiens

```
<400> SEQUENCE: 11

Val Thr Glu Tyr Leu Pro Ser Gly Cys Leu Leu
1               5                   10

<210> SEQ ID NO 12
<211> LENGTH: 11
<212> TYPE: PRT
<213> ORGANISM: Homo sapiens

<400> SEQUENCE: 12

Ile Thr Glu Tyr Met Glu Asn Gly Ser Leu Val
1               5                   10

<210> SEQ ID NO 13
<211> LENGTH: 11
<212> TYPE: PRT
<213> ORGANISM: Homo sapiens

<400> SEQUENCE: 13

Ile Thr Glu Tyr Met Ala Lys Gly Ser Leu Leu
1               5                   10

<210> SEQ ID NO 14
<211> LENGTH: 11
<212> TYPE: PRT
<213> ORGANISM: Homo sapiens

<400> SEQUENCE: 14

Val Met Glu Met Ala Glu Leu Gly Pro Leu Asn
1               5                   10
```